United States Patent
Rege et al.

(10) Patent No.: US 11,317,968 B2
(45) Date of Patent: *May 3, 2022

(54) METHODS AND COMPOSITIONS FOR TISSUE ADHESIVES

(71) Applicant: Arizona Board of Regents on behalf of Arizona State University, Scottsdale, AZ (US)

(72) Inventors: Kaushal Rege, Chandler, AZ (US); Huang-Chiao Huang, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 287 days.

This patent is subject to a terminal disclaimer.

(21) Appl. No.: 16/195,121

(22) Filed: Nov. 19, 2018

(65) Prior Publication Data
US 2019/0133685 A1    May 9, 2019

Related U.S. Application Data

(63) Continuation of application No. 14/413,822, filed as application No. PCT/US2013/054390 on Aug. 9, 2013, now Pat. No. 10,154,881.
(Continued)

(51) Int. Cl.
*A61B 18/20* (2006.01)
*A61B 18/18* (2006.01)
(Continued)

(52) U.S. Cl.
CPC ............ *A61B 18/203* (2013.01); *A61B 18/18* (2013.01); *A61B 18/20* (2013.01); *A61K 38/18* (2013.01);
(Continued)

(58) Field of Classification Search
CPC ..................... A61B 18/20; A61B 2017/0065; A61K 38/19; A61K 38/39; A61K 38/1808; A61K 38/1825; A61K 38/1841; A61L 24/108; A61L 24/0005; A61L 24/0015; A61L 24/0089
See application file for complete search history.

(56) References Cited

U.S. PATENT DOCUMENTS 7,001,328 B1    2/2006    Barofsky et al.
7,501,133 B2    3/2009    McNally-Heintzelman et al.
(Continued)

OTHER PUBLICATIONS

Ågren, M, Andersen, T, Andersen, L, Schiødt, C, Surve, V, Andreassen, T, Risteli, J, Franzén, L, Delaissé, J-M, Heegaard, A-M, Jorgensen, L. Nonselective matrix metalloproteinase but not tumor necrosis factor-a inhibition effectively preserves the early critical colon anastomotic integrity. International Journal of Colorectal Disease 2011; 26 (3): 329-337.
(Continued)

*Primary Examiner* — Tuan V Nguyen
(74) *Attorney, Agent, or Firm* — Riverside Law, LLP

(57) ABSTRACT

Disclosed herein are methods of connecting disrupted tissue, tissue repair, treating colorectal disorder and tissue welding. The methods comprise using a bioadhesive composition comprising ELP and light absorbing chromophores and irradiating the bioadhesive tissue.

20 Claims, 26 Drawing Sheets

Specification includes a Sequence Listing.

Related U.S. Application Data

(60) Provisional application No. 61/682,129, filed on Aug. 10, 2012.

(51) Int. Cl.

| | | |
|---|---|---|
| *A61L 24/10* | (2006.01) | |
| *A61K 38/18* | (2006.01) | |
| *A61K 38/19* | (2006.01) | |
| *A61L 24/00* | (2006.01) | |
| *A61K 41/00* | (2020.01) | |
| *A61K 38/39* | (2006.01) | |
| *A61N 5/06* | (2006.01) | |
| *A61N 5/067* | (2006.01) | |
| *A61B 18/14* | (2006.01) | |
| *A61B 18/00* | (2006.01) | |

(52) U.S. Cl.
CPC ...... *A61K 38/1808* (2013.01); *A61K 38/1825* (2013.01); *A61K 38/1841* (2013.01); *A61K 38/19* (2013.01); *A61K 38/39* (2013.01); *A61K 41/0052* (2013.01); *A61L 24/0005* (2013.01); *A61L 24/0015* (2013.01); *A61L 24/0089* (2013.01); *A61L 24/108* (2013.01); *A61N 5/062* (2013.01); *A61B 18/14* (2013.01); *A61B 2018/0063* (2013.01); *A61B 2018/00404* (2013.01); *A61B 2018/00452* (2013.01); *A61B 2018/00494* (2013.01); *A61B 2018/00505* (2013.01); *A61B 2018/1807* (2013.01); *A61L 2300/404* (2013.01); *A61L 2300/414* (2013.01); *A61L 2400/12* (2013.01); *A61N 5/067* (2021.08)

(56) References Cited

U.S. PATENT DOCUMENTS

| | | | |
|---|---|---|---|
| 7,981,871 | B2 | 7/2011 | Prestwich et al. |
| 2002/0119572 | A1* | 8/2002 | Jacobson ............... C12N 13/00 435/466 |
| 2004/0110439 | A1 | 6/2004 | Chaikof et al. |
| 2004/0117004 | A1* | 6/2004 | Osborne ................... A61F 2/07 623/1.36 |
| 2004/0202625 | A1 | 10/2004 | Daniloff et al. |
| 2005/0113937 | A1* | 5/2005 | Binette ................... A61L 27/58 623/23.73 |
| 2005/0196427 | A1 | 9/2005 | Tirrell et al. |
| 2008/0241262 | A1 | 10/2008 | Lee et al. |
| 2010/0049296 | A1* | 2/2010 | Sarasam ............... A61L 31/148 623/1.11 |
| 2012/0035608 | A1 | 2/2012 | Marchitto et al. |

OTHER PUBLICATIONS

Alencar, H, Funovics, MA, Figueiredo, J, Sawaya, H, Weissleder, R, Mahmood, U. Colonic Adenocarcinomas: Near-Infrared Microcatheter Imaging of Smart Probes for Early Detection,ÄìStudy in Mice1. Radiology 2007; 244(1):232-238.

Anderson, RH. Endoscopic laser surgery handbook (Science and practice of surgery series, vol. 10). International journal of cardiology 1988; 20(1): 157.

Anumolu, R, Gustafson, JA, Magda, JJ, Cappello, J, Ghandehari, H, Pease, LF. Fabrication of Highly Uniform Nanoparticles from Recombinant Silk-Elastin-like Protein Polymers for Therapeutic Agent Delivery. ACS Nano 2011; 5 (7): 5374-5382.

Asencioarana, F, Garciafons, V, Torresgil, V, Molinaandreu, E, Vidalmartinez, J, Perezsarrio, R, Martinezsoriano, F. Effects of a Low-Power He—Ne-Laser on the Healing of Experimental Colon Anastomoses—Our Experience. Optical Engineering 1992; 31(7): 1452-1457.

Barua, S, Joshi, A, Banerjee, A, Matthews, D, Sharfstein, ST, Cramer, SM, Kane, RS, Rege, K. Parallel Synthesis and Screening of Polymers for Nonviral Gene Delivery. Molecular Pharmaceutics 2009; 6(1): 86-97.

Bass, LS, Moazami, N, Pocsidio, J, Oz, MC, Logerfo, P, Treat, MR. Changes in Type-I Collagen Following Laser-Welding. Lasers in Surgery and Medicine 1992; 12(5): 500-505.

Beuran, M, Chiotoroiu, AL, Chilie, A, Morteanu, S, Vartic, M, Avram, M, Rosu, O, Lica, I. Stapled vs. hand-sewn colorectal anastomosis in complicated colorectal cancer—a retrospective study. Chirurgia 2010; 105(5): 645-651.

Bregy, A et al. Electromagnetic Tissue Fusion Using Superparamagnetic Iron Oxide Nanoparticles: First Experience With Rabbit Aorta. The Open Surgery Journal. 2008, vol. 2, pp. 3-9.

Capon, A, Iarmarcovai, G, Gonnelli, D, Degardin, N, Magalon, G, Mordon, S. Scar Prevention Using Laser-Assisted Skin Healing (LASH) in Plastic Surgery. Aesthetic Plastic Surgery 2010; 34(4): 438-446.

Chen, CC, Lin, YP, Wang, CW, Tzeng, HC, Wu, CH, Chen, YC, Chen, CP, Chen, LC, Wu, YC. DNA-gold nanorod conjugates for remote control of localized gene expression by near infrared irradiation. Journal of the American Chemical Society 2006; 128(11): 3709-3715.

Chikamatsu, E, Sakurai, T, Nishikimi, N, Yano, T, Nimura, Y. Comparison of Laser Vascular Welding, Interrupted Sutures, and Continuous Sutures in Growing Vascular Anastomoses. Lasers in Surgery and Medicine 1995; 16(1):34-40.

Cilesiz, I, Springer, T, Thomsen, S, Welch, AJ. Controlled temperature tissue fusion: Argon laser welding of canine intestine in vitro. Lasers in Surgery and Medicine 1996; 18(4): 325-334.

Cilesiz, I, Thomsen, S, Welch, AJ, Chan, EK. Controlled temperature tissue fusion: Ho:YAG laser welding of rat intestine in vivo .2. Lasers in Surgery and Medicine 1997; 21(3): 278-286.

Cilesiz, I, Thomsen, S, Welch, AJ. Controlled temperature tissue fusion: Argon laser welding of rat intestine in vivo .1. Lasers in Surgery and Medicine 1997; 21(3): 269-277.

Cilesiz, I. Controlled temperature photothermal issue welding. Journal of Biomedical Optics 1999; 4(3): 327-336.

Dallas, P, Sharma, VK, Zboril, R. Silver polymeric nanocomposites as advanced antimicrobial agents: Classification, synthetic paths, applications, and perspectives. Advances in Colloid and Interface Science; 166(1,Äì2): 119-135, 2011.

Dickerson E B, Dreaden E C, Huang X et al.: Gold nanorod assisted near-infrared plasmonic photothermal therapy (PPTT) of squamous cell carcinoma in mice. Cancer Lett. 269(1), 57-66 (2008).

Eckmann, L, Jung, HC, Schurermaly, C, Panja, A, Morzyckawroblewska, E, Kagnoff, MF. Differential Cytokine Expression by Human Intestinal Epithelial-Cell Lines—Regulated Expression of Interleukin-8. Gastroenterology 1993; 105(6): 1689-1697.

Galya, T, Sedlarik, V, Kuritka, I, Novotny, R, Sedlarikova, J, Saha, P. Antibacterial Poly(vinyl Alcohol) Film Containing Silver Nanoparticles: Preparation and Characterization. Journal of Applied Polymer Science 2008;(5): 3178-3185.

Garcia, P, Mines, MJ, Bower, KS, Hill, J, Menon, J, Tremblay, E, Smith, B. Robotic Laser Tissue Welding of Sclera Using Chitosan Films. Lasers in Surgery and Medicine 2009; 41(1): 60-67.

Gazelle G S, Goldberg SN, Solbiati L, Livraghi T: Tumor ablation with radiofrequency energy. Radiology 217(3), 633-646 (2000).

Gennaro, M, Ascer, E, Mohan, C, Wang, S. A Comparison of Co-2 Laser-Assisted Venous Anastomoses and Conventional Suture Techniques—Patency, Aneurysm Formation, and Histologic Differences. Journal of Vascular Surgery 1991; 14(5): 605-613.

Gibbons N B, Watson R W, Coffey R N, Brady H P, Fitzpatrick J M: Heat-shock proteins inhibit induction of prostate cancer cell apoptosis. Prostate 45(1), 58-65 (2000).

Gobin A M, Lee M H, Halas N J, James W D, Drezek R A, West J L: Near-infrared resonant nanoshells for combined optical imaging and photothermal cancer therapy. Nano Lett. 7(7), 1929-1934 (2007).

Gobin, AM, O'Neal, DP, Watkins, DM, Halas, NJ, Drezek, RA, West, JL. Near infrared laser-tissue welding using nanoshells as an exogenous absorber. Lasers in Surgery and Medicine 2005; 37(2):123-129.

(56) References Cited

OTHER PUBLICATIONS

Gong M C, Latouche J B, Krause A, Heston W D, Bander N H, Sadelain M: Cancer patient T cells genetically targeted to prostate-specific membrane antigen specifically lyse prostate cancer cells and release cytokines in response to prostate-specific membrane antigen. Neoplasia 1(2), 123-127 (1999).
Grubbs, PE, Wang, S, Marini, C, Basu, S, Rose, DM, Cunningham, JN. Enhancement of Co2-Laser Microvascular Anastomoses by Fibrin Glue. Journal of Surgical Research 1988; 45(1): 112-119.
Guillou, PJ, Quirke, P, Thorpe, H, Walker, J, Jayne, DG, Smith, AMH, Heath, RM, Brown, JM. Short-term endpoints of conventional versus laparoscopic-assisted surgery in patients with colorectal cancer (MRC CLASICC trial): multicentre, randomised controlled trial. Lancet 2005; 365(9472): 1718-1726.
He X M, Walkers W F, Crowe J H, Swanlund D J, Bischof J C: In situ thermal denaturation of proteins in dunning at-1 prostate cancer cells: implication for hyper-thermic cell injury. Ann. Biomed. Engin. 32(10), 1384-1398 (2004).
Heath E I, Hillman D W, Vaishampayan U et al.: A Phase II trial of 17-allylamino-17-demethoxygeldana-mycin inpatients with hormone-refractory metastatic prostate cancer. Clin. Cancer Res. 14(23), 7940-7946 (2008).
Hilger I, Andra W, Bahring R, Daum A, Hergt R, Kaiser W A: Evaluation of temperature increase with different amounts of magnetite in liver tissue samples. Inves-tig. Radio!. 32(11), 705-712 (1997).
Hooper, L. V., et al., Molecular analysis of commensal host-microbial relations hips in the intestine. Science, 2001. 291(5505): p. 881-884.
Hu, M, Chen, JY, Li, ZY, Au, L, Hartland, GV, Li, XD, Marquez, M, Xia, YN. Gold nanostructures: engineering their plasmonic properties for biomedical applications. Chemical Society Reviews 2006; 35(11): 1084-1094.
Huang X H, Jain P K, El-Sayed I H, El-Sayed MA: Determination of the minimum temperature required for selective photothermal destruction of cancer cells with the use of immunotargeted gold nanoparticles. Photochem. Photobiol. 82 (2), 412-417 (2006).
Huang X, El-Sayed I H, Qian W, El-Sayed M A: Cancer cell imaging and photothermal therapy in the near-infrared region by using gold nanorods. J. Am. Chem. Soc. 128(6), 2115-2120 (2006).
Huang, H et al. InvestigatiOI) Of Phase Separation Behavior And Formation Of Plasmonic Nanocomposites From Polypeptide-Gold Nanorod Nanoassemblies. Langmuir. Mar. 6, 2012, vol. 28, pp. 6645-6655; p. 6645.
Huang, HC, Barua, S, Kay, DB, Rege, K. Simultaneous Enhancement of Photothermal Stability and Gene Delivery Efficacy of Gold Nanorods Using Polyelectrolytes. Acs Nano 2009; 3(10): 2941-2952.
Huang, HC, Koria, P, Parker, SM, Selby, L, Megeed, Z, Rege, K. Optically responsive gold nanorod-polypeptide assemblies. Langmuir 2008; 24(24): 14139-44.
Huang, HC, Rege, K, Heys, JJ. Spatiotemporal temperature distribution and cancer cell death in response to extracellular hyperthermia induced by gold nanorods. ACS Nano 2010; 4(5): 2892-900.
Huang, HC, Yang, Y, Nanda, A, Koria, P, Rege, K. Synergistic administration of photothermal therapy and chemotherapy to cancer cells using polypeptide-based degradable plasmonic matrices. Nanomedicine (Lond) 2011; 6(3): 459-73.
Huang, L, McMillan, RA, Apkarian, RP, Pourdeyhimi, B, Conticello, VP, Chaikof, EL. Generation of synthetic elastinmimetic small diameter fibers and fiber networks. Macromolecules 2000; 33(8): 2989-2997.
Huang, XH, Jain, PK, El-Sayed, IH, El-Sayed, MA. Plasmonic photothermal therapy (PPTT) using gold nanoparticles. Lasers in Medical Science 2008; 23(3): 217-228.
Husebye, E., et al., Influence of microbial species on small intestinal myoelectric activity and transit in germ free rats. American Journal of Physiology Gastrointestinal and Liver Physiology, 2001. 280(3): p. G368-G380.

Isbister, WH. Anastomotic leak in colorectal surgery: A single surgeon's experience. Anz Journal of Surgery 2001; 71(9): 516-520.
Janorkar A V, Rajagopalan P, Yarmush M L, Megeed Z: The use of elastin-like polypeptide-polyelectrolyte complexes to control hepatocyte morphology and function in vitro. Biomaterials 29(6), 625-632 (2008).
Jolesz F A, Hynynen K: Magnetic resonance image-guided focused ultrasound surgery. Cancer J. 8, S100-S112 (2002).
Jung, HC, Eckmann, L, Yang, SK, Panja, A, Fierer, J, Morzyckawroblewska, E, Kagnoff, MF. A Distinct Array of Proinflammatory Cytokines Is Expressed in Human Colon Epithelial-Cells in Response to Bacterial Invasion. Journal of Clinical Investigation 1995; 95(1): 55-65.
Karanjia, ND, Corder, AP, Bearn, P, Heald, RJ. Leakage from Stapled Low Anastomosis after Total Mesorectal Excision for Carcinoma of the Rectum. British Journal of Surgery 1994; 81(8): 1224-1226.
Kim, JC, Lee, YK, Lim, BS, Rhee, SH, Yang, HC. Comparison of tensile and knot security properties of surgical sutures. Journal of Materials Science—Materials in Medicine 2007; 18(12): 2363-2369.
Kim, W, Chaikof, EL. Recombinant elastin-mimetic biomaterials: Emerging applications in medicine. Advanced Drug Delivery Reviews 2010; 62(15): 1468-1478.
Kirsch, AJ, Miller, MI, Hensle, TW, Chang, DT, Shabsigh, R, Olsson, CA, Connor, JP. Laser-Tissue Soldering in Urinary-Tract Reconstruction—First Human-Experience. Urology 1995; 46(2): 261-266.
Klioze, SD, Poppas, DP, Rooke, CT, Choma, TJ, Schlossberg, SM. Development and Initial Application of a Real-Time Thermal Control-System for Laser-Tissue Welding. Journal of Urology 1994; 152(2): 744-748.
Koria, P, Yagi, H, Kitagawa, Y, Megeed, Z, Nahmias, Y, Sheridan, R, Yarmush, ML. Self-assembling elastin-like peptides growth factor chimeric nanoparticles for the treatment of chronic wounds. Proc Natl Acad Sci U S A 2011; 108 (3): 1034-9.
LaJoie, EN, Barofsky, AD, Gregory, KW, Prahl, SA. Patch welding with a pulsed diode laser and indocyanine green. Lasers in Medical Science 1997; 12(1): 49-54.
Lauto, A, Foster, LJR, Ferris, L, Avolio, A, Zwaneveld, N, Poole-Warren, LA. Albumin-genipin solder for laser tissue repair. Lasers in Surgery and Medicine 2004; 35(2): 140-145.
Leduc, M. and J. Vanheijenoort, Autolysis of *Escherichia coli*. Journal of Bacteriology, 1980. 142(1):p. 52-59.
Leduc, M., R. Kasra, and J. Vanheijenoort, Induction and Control of the Autolytic System of *Escherichia coli*. Journal of Bacteriology, 1982. 152(1): p. 26-34.
Lepock J R: Cellular effects of hyperthermia: Relevance to the minimum dose for thermal damage. Int. J. Hypertherm. 19(3), 252-266 (2003).
Liang, CC, Park, AY, Guan, JL. In vitro scratch assay: a convenient and inexpensive method for analysis of cell migration in vitro. Nature Protocols 2007; 2(2): 329-333.
Lippert, E, Klebl, F, Schweller, F, Ott, C, Gelbmann, C, Schölmerich, J, Endlicher, E, Kullmann, F. Fibrin glue in the endoscopic treatment of fistulae and anastomotic leakages of the gastrointestinal tract. International Journal of Colorectal Disease 2011; 26(3): 303-311.
Lipska, M. A., et al., Anastomotic leakage after lower gastrointestinal anastomosis: Men are at a higher risk Anz Journal of Surgery, 2006. 76(7): p. 579-585.
Lowery A R, Gobin A M, Day E S, Halas N J, West J L: Immunonanoshells for targeted photothermal ablation of tumor cells. Int. J. Nanomed. 1(2), 149-154 (2006).
Ma L L, Feldman M D, Tam J M et al.: Small multifunctional nanoclusters (nanoroses) for targeted cel-lular imaging and therapy. ACS Nano 3(9), 2686-2696 (2009).
MacEwan, SR, Chilkoti, A. Elastin-like polypeptides: Biomedical applications of tunable biopolymers. Peptide Science 2010; 94(1): 60-77.
Mackay, JA, Chilkoti, A. Temperature sensitive peptides: Engineering hyperthermia-directed therapeutics. International Journal of Hyperthermia 2008; 24(6): 483-495.

(56) References Cited

OTHER PUBLICATIONS

MacRae, HM, McLeod, RS. Handsewn vs. stapled anastomoses in colon and rectal surgery—A meta-analysis. Diseases of the Colon & Rectum 1998; 41(2): 180-189.

Matteini, P, Ratto, F, Rossi, F, Centi, S, Dei, L, Pini, R. Chitosan Films Doped with Gold Nanorods as Laser-Activatable Hybrid Bioadhesives. Advanced Materials 2010; 22(38): 4313-4316.

Matteini, P, Ratto, F, Rossi, F, Cicchi, R, Stringari, C, Kapsokalyvas, D, Pavone, FS, Pini, R. Photothermally-induced disordered patterns of corneal collagen revealed by SHG imaging. Optics Express 2009; 17(6): 4868-4878.

Matteini, P, Ratto, F, Rossi, F, Rossi, G, Esposito, G, Puca, A, Albanese, A, Maira, G, Pini, R. In vivo carotid artery closure by laser activation of hyaluronan-embedded gold nanorods. Journal of Biomedical Optics 2010; 15(4):0415081-0415086.

Matteini, P, Rossi, F, Menabuoni, L, Pini, R. Microscopic characterization of collagen modifications induced by lowtemperature diode-laser welding of corneal tissue. Lasers in Surgery and Medicine 2007; 39(7): 597-604.

McDaniel, JR, Callahan, DJ, Chilkoti, A. Drug delivery to solid tumors by elastin-like polypeptides. Advanced Drug Delivery Reviews 2010; 62(15): 1456-1467.

Mchale, MK, Setton, LA, Chilkoti, A. Synthesis and in vitro evaluation of enzymatically cross-linked elastin-like polypeptide gels for cartilaginous tissue repair. Tissue Engineering 2005; 11(11-12): 1768-1779.

McKenna, KA, Hinds, MT, Sarao, RC, Wu, P-C, Maslen, CL, Glanville, RW, Babcock, D, Gregory, KW. Mechanical property characterization of electrospun recombinant human tropoelastin for vascular graft biomaterials. Acta Biomaterialia 2012; 8(1): 225-233.

Meyer D E, Chilkoti A: Genetically encoded synthesis of protein-based polymers with precisely specified molecular weight and sequence by recursive directional ligation: examples from the elastin-like polypeptide system. Biomacromolecules 3(2), 357-367 (2002).

Moyer, MP, Manzano, LA, Merriman, RL, Stauffer, JS, Tanzer, LR. NCM460, a normal human colon mucosal epithelial cell line. In Vitro Cellular & Developmental Biology—Animal 1996; 32(6): 315-317.

Murray, LW, Su, L, Kopchok, GE, White, RA. Crosslinking of Extracellular-Matrix Proteins—a Preliminary-Report on a Possible Mechanism of Argon-Laser Welding. Lasers in Surgery and Medicine 1989; 9(5): 490-496.

Nelson, H, Sargent, D, Wieand, HS, Fleshman, J, Anvari, M, Stryker, SJ, Beart, RW, Hellinger, M, Flanagan, R, Peters, W, Ota, D, Hellinger, M. A comparison of laparoscopically assisted and open colectomy for colon cancer. New England Journal of Medicine 2004; 350(20): 2050-2059.

Nettles, DL, Chilkoti, A, Setton, LA. Applications of elastin-like polypeptides in tissue engineering. Advanced Drug Delivery Reviews 2010; 62(15): 1479-1485.

Nikoobakht B, El-Sayed M A: Preparation and growth mechanism of gold nanorods (NRs) using seed-mediated growth method. Chem. Mater. 15(10), 1957-1962 (2003).

Ott,B., etal., Comparative in vitro study of tissue welding using a 808nm diode laser and a Ho:YAG laser. LasersinMedicalScience,2001. 16(4):p. 260-266.

Overgaard J: The current and potential role of hyperthermia in radiotherapy. Int. J. Radiat. Oneal. Biol. Phys. 16(3), 535-549 (1989).

Park, H., et al., Effect of Swelling Ratio of Injectable Hydrogel Composites on Chondrogenic Differentiation of Encapsulated Rabbit Marrow Mesenchymal Stem Cells In Vitro. Biomacromolecules, 2009. 10(3): p. 541-546.

Park, IJ. Influence of anastomotic leakage on oncological outcome in patients with rectal cancer. J Gastrointest Surg 2010; 14(7): 1190-6.

Pasternak, B, Matthiessen, P, Jansson, K, Andersson, M, Aspenberg, P. Elevated intraperitoneal matrix metalloproteinases-8 and -9 in patients who develop anastomotic leakage after rectal cancer surgery: a pilot study. Colorectal Disease 2010; 12(7Online): e93-e98.

Pasternak, B, Rehn, M, Andersen, L, Ågren, M, Heegaard, A-M, Tengvall, P, Aspenberg, P. Doxycycline-coated sutures improve mechanical strength of intestinal anastomoses. International Journal of Colorectal Disease 2008; 23 (3): 271-276.

Pickleman, J., et al., The failed gastrointestinal anastomosis: An inevitable catastrophe? Journal of the American College of Surgeons, 1999. 188(5): p. 473-482.

Poppas, D, Sutaria, P, Sosa, RE, Mininberg, D, Schlossberg, S. Chromophore Enhanced Laser-Welding of Canine Ureters in-Vitro Using a Human Protein Solder—a Preliminary Step for Laparoscopic Tissue Welding. Journal of Urology 1993; 150(3): 1052-1055.

Poppas, DP, Massicotte, JM, Stewart, RB, Roberts, AB, Atala, A, Retik, AB, Freeman, MR. Human albumin solder supplemented with TGF-beta(1) accelerates healing following laser welded wound closure. Lasers in Surgery and Medicine 1996; 19(3): 360-368.

Poppas, DP, Stewart, RB, Massicotte, M, Wolga, AE, Kung, RTV, Retik, AB, Freeman, MR. Temperature-controlled laser photocoagulation of soft tissue: In vivo evaluation using a tissue welding model. Lasers in Surgery and Medicine 1996; 18(4): 335-344.

Post, S., et al., Risks of Intestinal Anastomoses in Crohns-Disease. Annals of Surgery, 1991. 213(1): p. 37-42.

Qiu, WG, Teng, WB, Cappello, JY, Wu, X. Wet-Spinning of Recombinant Silk-Elastin-Like Protein Polymer Fibers with High Tensile Strength and High Deformability. Biomacromolecules 2009; 10(3):602-608.

Rai, M, Yadav, A, Gade, A. Silver nanoparticles as a new generation of antimicrobials. Biotechnology Advances 2009; 27(1): 76-83.

Ratto, F, Matteini, P, Cini, A, Centi, S, Rossi, F, Fusi, F, Pini, R. CW laser-induced photothermal conversion and shape transformation of gold nanodogbones in hydrated chitosan films. Journal of Nanoparticle Research 2011; 13(9):4337-4348.

Raub, CB, Putnam, AJ, Tromberg, BJ, George, SC. Predicting bulk mechanical properties of cellularized collagen gels using multiphoton microscopy. Acta Biomaterialia 2010; 6(12): 4657-4665.

Rege K, Patel S J, Megeed Z, Yarmush M L: Amphipathic peptide-based fusion peptides and immuno- conjugates for the targeted ablation of prostate cancer cells. Cancer Res. 67(13), 6368-6375 (2007).

Rnjak-Kovacina, J, Wise, SG, Li, Z, Maitz, PKM, Young, CJ, Wang, Y, Weiss, AS. Tailoring the porosity and pore size of electrospun synthetic human elastin scaffolds for dermal tissue engineering. Biomaterials 2011; 32(28): 6729-6736.

Rubert Pérez, CM, Panitch, A, Chmielewski, J. A Collagen Peptide-Based Physical Hydrogel for Cell Encapsulation. Macromolecular Bioscience 2011; 11(10): 1426-1431.

Rylander M N, Feng Y, Bass J, Diller K R: Thermally induced injury and heat-shock protein expression in cells and tissues.Ann. NYAcad. Sci. 1066, 222-242 (2005).

Schober, R, Ulrich, F, Sander, T, Durselen, H, Hessel, S. Laser-Induced Alteration of Collagen Substructure AllowsMicrosurgical Tissue Welding. Science 1986; 232(4756): 1421-1422.

Seki T, Wakabayashi M, Nakagawa T et al.: Per-cutaneous microwave coagulation therapy for solitary metastatic liver tumors from colorectal cancer: a pilot clini-cal study. Am. J. Gastroenterol. 94(2), 322-327 (1999).

Shao, X, Zheng, W, Huang, Z. Near-infrared autofluorescence spectroscopy for in vivo identification of hyperplastic and adenomatous polyps in the colon. Biosensors and Bioelectronics 2011; 30(1): 118-122.

Skardal, A, Zhang, J, McCoard, L, Oottamasathien, S, Prestwich, GD. Dynamically Crosslinked Gold Nanoparticle—Hyaluronan Hydrogels. Advanced Materials 2010; 22(42): 4736-4740.

Skrabalak S E, Chen J, Sun Y et al.: Gold nano-cages: synthesis, properties, and applications. Accounts Chem. Res. 41(12), 1587-1595 (2008).

Smith, RL, Bohl, JK, McElearney, ST, Friel, CM, Barclay, MM, Sawyer, RG, Foley, EF. Wound infection after elective colorectal resection. Annals of Surgery 2004; 239(5): 605.

(56) References Cited

OTHER PUBLICATIONS

Solit D B, Osman I, Polsky D et al.: Phase II trial of 17-allylamino-17-demethoxygeldanamycin in patients with metastatic melanoma. Clin. Cancer Res. 14(24), 8302-8307 (2008).

Spector, D, Rabi, Y, Vasserman, I, Hardy, A, Klausner, J, Rabau, M, Katzir, A., In Vitro Large Diameter Bowel Anastomosis Using a Temperature Controlled Laser Tissue Soldering System and Albumin Stent, Lasers in Surgery and Medicine 41:504-508 (2009).

Stechmiller, J et al. The Role Of Doxycycline As A Matrix Metalloproteinase Inhibitor For The Treatment Of Chronic Wounds. Biological Research For Nursing. Dec. 22, 2009, Yol. 11, No. 4, pp. 336-344.

Teng, W, Cappello, J, Wu, X. Recombinant Silk-Elastinlike Protein Polymer Displays Elasticity Comparable to Elastin. Biomacromolecules 2009; 10(11): 3028-3036.

Thomsen, S, Morris, JR, Neblett, CR, Mueller, J. Tissue Welding Using a Low-Energy Microsurgical Co2-Laser. Medical Instrumentation 1987; 21(4): 231-237.

Thomson, GA. An investigation of leakage tracts along stressed suture lines in phantom tissue. Medical Engineering & Physics 2007; 29(9): 1030-1034.

Tong L, Wei Q, Wei A, Cheng J-X: Gold nanorods as contrast agents for biological imaging: optical properties, surface conjugation and photothermal effects. Photo-chem. Photobiol. 85(1), 21-32 (2009).

Urry D W: Physical chemistry of biological free energy transduction as demonstrated by elastic protein-based polymers. J. Phys. Chem. B 101(51), 11007-11028 (1997).

Vimala, K, Mohan, YM, Sivudu, KS, Varaprasad, K, Ravindra, S, Reddy, NN, Padma, Y, Sreedhar, B, MohanaRaju, K. Fabrication of porous chitosan films impregnated with silver nanoparticles: A facile approach for superior antibacterial application. Colloids and Surfaces B-Biointerfaces 2010; 76(1):248-258.

Von Maltzahn G, Park J H, Agrawal A et al.:Computationally guided photothermal tumor therapy using longcirculating gold nanorod antennas. Cancer Res. 69(9), 3892-3900 (2009).

Wadia, Y, Xie, H, Kajitani, M. Liver repair and hemorrhage control by using laser soldering of liquid albumin in a porcine model. Lasers in Surgery and Medicine 2000; 27(4): 319-328.

Watters, DAK, Smith, AN, Eastwood, MA, Anderson, KC, Elton, RA, Mugerwa, JW. Mechanical-Properties of the Colon—Comparison of the Features of the African and European Colon Invitro. Gut 1985; 26(4): 384-392.

Wei, DW, Sun, WY, Qian, WP, Ye, YZ, Ma, XY. The synthesis of chitosan-based silver nanoparticles and their antibacterial activity. Carbohydrate Research 2009; 344(17): 2375-2382.

Weissleder, R. A clearer vision for in vivo imaging. Nature Biotechnology 2001; 19(4): 316-317.

Werner, S, Grose, R. Regulation of wound healing by growth factors and cytokines. Physiological Reviews 2003; 83(3): 835-870.

Wise, L., W. McAlister, and T. Stein, Studies on the healing of anastomoses of small and large intestines. Surg Gynecol Obstet, 1975. 141(190).

Wolf-de Jonge, ICD, Beek, JF, Balm, R. 25 years of laser assisted vascular anastomosis (LAVA): What have we learned? European Journal of Vascular and Endovascular Surgery 2004; 27(5): 466-476.

Wu, Y, MacKay, JA, McDaniel, JR, Chilkoti, A, Clark, RL. Fabrication of Elastin-Like polypeptide Nanoparticles for Drug Delivery by Electrospraying. Biomacromolecules 2009; 10(1): 19-24.

Xie,H., et al.,Laser assisted vascular end to end anastomosis of elastin heterograft to carotid artery with an albumin stent:A preliminary in vivo study. Lasers in Surgery and Medicine,2004. 35(3):p. 201-205.

Zuger, BJ, Ott, B, Mainil-Varlet, P, Schaffner, T, Clemence, JF, Weber, HP, Frenz, M. Laser solder welding of articular cartilage: Tensile strength and chondrocyte viability. Lasers in Surgery and Medicine 2001; 28(5): 427-434.

* cited by examiner

METHODS AND COMPOSITIONS FOR TISSUE ADHESIVES

CROSS-REFERENCE TO RELATED APPLICATIONS

This Application claims the benefit of U.S. Provisional Application No. 61/682,129, filed on Aug. 10, 2012, which is incorporated herein by reference in its entirety.

STATEMENT REGARDING FEDERALLY SPONSORED RESEARCH

This invention was made with government support under HDTRA1-10-1-0109 awarded by the Defense Threat Reduction Agency (DTRA). The United States government has certain rights in the invention.

BACKGROUND

Surgical procedures that excise tissue or repair of tissues that are separated or disrupted often require suturing or staples to join the free ends of the tissue again to form a close seal for healing of the tissues. In some instances, the tissues must be connected tightly enough to prevent fluids or materials contained on one side of the attached tissue from leaking through to the other side of the tissue or from entering a surrounding body cavity. Maintaining the structural integrity of the original tissue at the repair site is a goal in creating the repair site. Surgical repair of gastrointestinal tissues, particularly after excision of tissue or growths, often results in repair sites that do not sufficiently seal the tissues to prevent leakage of intestinal materials into the surrounding peritoneal cavity.

Treatment of colorectal diseases may require surgical intervention include such diseases as colorectal cancer and inflammatory bowel disease (IBD) among others. In the United States, approximately 143,000 and 1.4 million people suffer from colorectal cancer and inflammatory bowel disease (IBD), respectively (National Cancer Institute and Centers for Disease Control and Prevention). Thus, every year, over 600,000 people in the United States will undergo surgical procedures to treat a number of colorectal diseases such as colorectal cancer, inflammatory bowel disease (IBD), and diverticulitis (inflammation of pouches formed on the other side of the colon) ([19, 20]. Patients undergo either conventional open surgery or laparoscopic surgeries to remove diseased tissue[21]. These patients require end-to-end anastomoses of the healthy sections following removal of diseased segments (FIG. 1). Surgical suturing and stapling are still the most common and important procedures in colorectal anastomoses[22, 23]. However, both methods rely on piercing healthy tissue and can cause anastomosis leakage. Leakage of intestinal bacteria from the bacteria-rich colorectal system into abdominal lumen can cause serious infection leading to potentially deadly peritonitis[3, 4, 6, 24]. It is reported that one-third of the mortality after colorectal surgery is due to anastomosis leakage[25]. Alternative or supportive anastomosis methods are urgently required in order to decrease leakage rate and promote tissue regeneration after colorectal surgery.

Laser tissue welding (LTW) has emerged as a "sutureless" surgical method for the anastomosis of ruptured tissues (e.g. vessels, bowel, urinary tract, skin and others)[17-15]. In LTW, laser light is absorbed by the tissue, which converts it into heat energy, resulting in the alteration of tissue proteins[14, 16]. Fusing of the photothermally altered tissue proteins via covalent and electrostatic interactions[11, 17, 18] is thought to be the primary mechanism responsible for welding (fusing) tissues. However, the efficacy of LTW is severely restricted due to lack of effective bioadhesives that fuse tissues. Specifically, laser irradiation of tissues can result in photothermal conversion of light to heat, resulting in denaturation/structural change of proteins, which fuse at the weld site. This process results in improved tensile strength of the closure and minimized peripheral tissue destruction. The advantages of laser-assisted tissue welding (LTW) over conventional suturing and stapling include short operation times, immediate fluid-tight sealing, reduced foreign-body reactions (e.g. inflammatory response) and scar formation and accelerated healing[10, 26-30]. Concerns associated with LTW include insufficient anastomoses strengths due to suboptimal bioadhesive performance, limited light penetration depth, and peripheral tissue thermal damage.

Accordingly, there is a need for materials and methods that can connect disrupted tissue using a light source. Such materials and methods are disclosed herein.

SUMMARY

In accordance with the purpose(s), as embodied and broadly described herein, in one aspect, relates to connection of tissue, welding tissue, tissue repair and treating colorectal disorders.

Disclosed herein is a method of connecting disrupted tissue, comprising, a) applying an effective amount of a photothermally responsive bioadhesive composition comprising an ELP and a light absorbing chromophore to disrupted tissue in need of being connected; and b) applying an effective amount of a directed light beam to the photothermally responsive bioadhesive composition and/or the tissue.

In one aspect, instead of using light absorbing chromophore, in the methods described herein, energy absorbing materials, such as magnetic particles can be used. The particles can be nanoparticles. Suitable magnetic particles include, but are not limited to iron nanoparticles (iron oxide). The magnetic particles can be magnetothermal particles. When such particles are used directed magnetic or radio frequency methods are used rather than a directed light beam as described in the methods herein.

Also disclosed herein is a method of laser tissue welding, comprising, a) applying an effective amount of a photothermally responsive bioadhesive composition comprising an ELP and a light absorbing chromophore to disrupted tissue in need of being welded; and b) applying an effective amount of a directed light beam to the photothermally responsive bioadhesive composition and/or the tissue.

Also disclosed herein is a method of tissue repair, comprising, a) suturing a tissue with fibers comprising a photothermally responsive composition comprising an ELP and a light absorbing chromophore; and b) optionally, applying an effective amount of a photothermally responsive bioadhesive composition comprising an ELP and a light absorbing chromophore to the sutured site; and c) applying an effective amount of a directed light beam to the sutures and/or to the tissue, and optionally to the photothermally responsive bioadhesive composition.

Also disclosed herein is a method of treating colorectal disease, comprising, a) applying an effective amount of a photothermally responsive bioadhesive composition comprising an ELP and a light absorbing chromophore to disrupted colorectal tissue; and b) applying an effective amount of a directed light beam to the photothermally responsive bioadhesive composition and/or the tissue.

In one aspect, the bioadhesive composition can comprise at least 0.5%, 1%, 2%, 4%, 5% or 8% of a light absorbing chromophore. The preferred loading is approximately 5% of light absorbing chromophores. The chromophores may be physically entrapped within the ELP or chemically conjugated to the ELP.

In one aspect, the heat generated from the light absorbing chromophore produces a bulk temperature, such as a tissue temperature and/or bioadhesive temperature, of at least 55° C., 60° C., 65° C., 70° C., 75° C., 80° C., 85° C. or 90° C.

In one aspect, the light absorbing chromophore crosslink the ELP through the heat generated from the absorption of energy through the directed light beam. In one aspect, the crosslinking connects disrupted tissue and can help the healing of wounds or cuts.

In one aspect, the light absorbing chromophore can comprise silver nanoparticles, gold nanorods, or gold nanoparticles, or mixtures thereof.

In one aspect, an ELP comprises cysteine residues. An ELP can, for example, comprise at least 2, 4, 6, 8, 10, 12 or 14 cysteine residues. In one aspect, the ELP can comprise at least 8 or 12 cysteine residues. In one aspect, the ELP comprises 8 or 12 cysteine residues in the sequence: MVSACRGPG-[VG VPGVG VPGVG VPGVG VPGVG VPG]$_8$-[VG VPGVG VPGVG VPGCG VPGVG VPG]$_8$-WP (SEQ ID NO:1) or MVSACRGPG-[VG VPGVG VPGVG VPGVG VPGVG VPG]$_8$-[VG VPGVG VPGVG VPGCG VPGVG VPG]$_{12}$-WP (SEQ ID NO:2).

In one aspect, the bioadhesive composition can reproducibly produce tissue temperature of at least 65° C. upon irradiation from a light source.

In one aspect, the bioadhesive composition can have anti-microbial properties, such as anti-bacterial properties. For example, the bioadhesive composition can comprise an anti-bacterial agent. Suitable antibacterial agents include, but are not limited to, MMP inhibitors, small-molecule drugs, peptides, and silver nanoparticles.

In one aspect, the directed light beam can be a laser, such as a Titanium-Sapphire laser, Krypton laser, Ruby laser, Chromium doped chrysoberyl (alexandrite) laser, Divalent samarium doped calcium fluoride (Sm:CaF$_2$) laser, AlGaInP laser, AlGaAs laser, Vertical cavity surface emitting laser (VCSEL). In one aspect, the tissue in need of being welded is from a cut or soar. In another aspect, the in need of being welded is from surgery.

In one aspect, the bioadhesive composition is suitable for suturing. For example, the bioadhesive tissue can be in the form a sting or other suitable for suturing. For example, the bioadhesive composition is in the form of a fiber.

In one aspect, the directed light beam is a laser, such as a Titanium-Sapphire laser. In one aspect, the wavelength of the light from the directed light source is in the near infrared region of the light absorption spectrum.

In another aspect, the bioadhesive composition further comprises cells. Suitable cells include but are not limited to, NCM460, fibroblasts, stem cells or mixtures thereof.

In one aspect, the disrupted tissue in need of being welded is from sore or cut. For example, the disrupted tissue in need of being welded is from a surgical cut.

In one aspect, the disrupted colorectal tissue is from a section of the colon that has been removed during surgery.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 16 at (B)) and release of the heat-shock inhibitor drug 17-AAG (FIG. 16 at (A)). This pattern of uniform cell death throughout the well is higher than what was seen with the single agent (i.e., mild hyperthermia alone and 17-AAG release alone) treatments. Approximate locations of the images are on the matrix are shown. Representative images from three independent experiments (n=3). Scale bar: 500 µm.

Figure 1A:
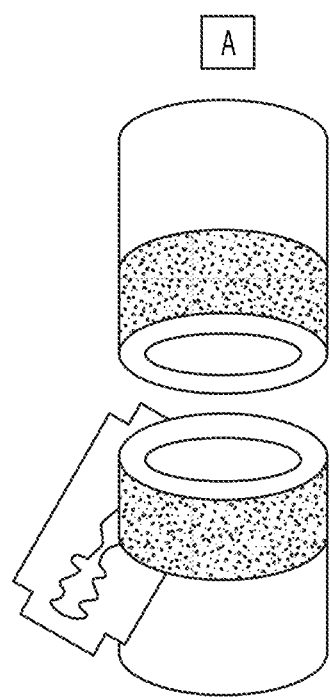
FIGS. 1A-1C show a schematic of laser tissue welding (LTW) using Plasmonic Nanoparticle (PNP)-ELP nanocomposites for end-to-end colorectal anastomosis after surgical resection. (A) Removal of diseased colon. (B) LTW or combined suturing and LTW using acellular or cellularized PNP-ELP nanocomposite. (C) Fluid-tight sealing with reduced leakage and accelerated healing.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

1. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the term "bulk temperature" or the like terms refer to the temperature that is produced in a material, i.e., bioadhesive composition, from the heat generated from a light absorbing chromophore once irradiated with light. For example, a "bulk temperature" can be the temperature in a bioadhesive composition that was generated from gold nanorods upon exposure to a laser. The temperature of the bioadhesive composition or a portion thereof can have a bulk temperature. Also the temperature in the tissue surrounding the bioadhesive composition can have a bulk temperature.

As used herein, the terms "optional" or "optionally" means that the subsequently described event or circumstance can or cannot occur, and that the description includes instances where said event or circumstance occurs and instances where it does not.

As used herein, the term "photothermally responsive bioadhesive composition" or the like terms refer to a bioadhesive composition that can be heated once irradiated with a directed light beam. For example, a composition of ELP and a light absorbing chromophore that heats up once irradiated with a laser is a photothermally responsive bioadhesive composition.

As used herein, the term "encapsulated in" or the like terms refer to when individual particles/cells are incorporated within a network, such a as a ELP network, which forms the nanocomposite. This can be accomplished by mixing cells with soluble polypeptide (liquid) and then inducing a phase change from the liquid phase to solid phase in order to physically entrap cells within the interconnected ELP matrix Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible nonexpress basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

2. Methods

The present invention comprises methods and compositions for repair of tissues and organs, such as tissues or organs that have undergone disruption of the tissue or organ such as tears, removal of sections of the tissue or organ, or addition of cellular or acellular materials to the tissue or organ. Disclosed herein are methods for repair of disrupted gastrointestinal organs, such as the colon, large bowel, or small bowel, but the present invention is not limited to only the disclosed applications of the methods, but it is contemplated other tissues and organs could benefit from the same repair methods. As used herein, a "disrupted" tissue or organ is a tissue or organ that has undergone a tear or cut, whether by intention, such as in surgery, or by accident, such as in a traumatic event, such that free ends or free surfaces are created in what was once a whole tissue or organ. For example, two free ends in the colon are created when a section of the colon is removed surgically. In general surgical methods, the two free ends may be joined to each other with sutures to form a repair site. Methods disclosed herein may be used to join the two free ends to each other to form a repair site. In some instances, one free end may be created by a surgical or accidental event, and the one free end may be closed by methods disclosed herein.

Laser-assisted colorectal anastomoses can provide immediate fluid-tight sealing upon treatment, and may reduce the frequency of colonic anastomosis leakage[35]. Cilesiz et al. reported that Ho:YAG and argon laser welding of rat intestine resulted in a comparable bursting pressure and healing rate to suture anastomoses[36, 37]. In a canine jejunum study, strong tissue fusion was not possible at or below a surface temperature of 70° C., but was accomplished above 80° C.[26]. Lauto et al. reported genipin-crosslinked albumin can significantly increase the tensile strength of adhesive-tissue bonds after laser welding[35]. TGF-β, a key component in the fibrogenic process and inflammatory response, was incorporated into human albumin solder to accelerate wound healing process after laser welding[38]. Overall, it is recognized that temperatures above 60° C. are necessary to provide robust closure[39]. The ability to precisely deliver laser energy is important in LTW[26, 39-41]. Additionally, matrix metalloproteinase (MMP) over expression is common and causes tissue degradation during early stages of colon repair[42, 43].

The light dosage required to induce similar thermal response using gold nanostructures is 10- to 25-fold lower than with photoabsorbing dyes[45]. GNRs, possess among the highest near infrared (NIR) absorption efficiencies[46] and can convert light into heat most efficiently compared to other gold nanoparticles. Moreover, light in NIR region demonstrates maximal tissue penetration, due to minimal light absorption by water and bloody[47]. Silver nanoparticles are also excellent photothermal convertors.

Although PNP-ELP based LTW may occur on exposed tissue during surgery, administration of NIR light is possible in the colon in vivo[48] including using endoscopes or catheters[49]. NIR light enables deeper penetration and localization of heat in the tissue. Further, use of plasmonic nanoparticles can mean high localization of heat energy leading to greater welding efficacies, and reduction in unwanted peripheral thermal damage[33, 34]. Silver (Ag), including Ag nanoparticles (AgNP)[67-69], demonstrates antibacterial properties[70].

ELPs are reported to be biocompatible with low immunogenicities[50] and have been explored for diverse applications[51-53], including treatment of chronic wounds in vivo[54]. However, low dynamic shear stiffness associated with ELP coacervates can limit their application in regenerative medicine, specifically, in cases where significant load support may be required[55]. Crosslinking ELPs with metallic nanoparticles can provide improved dynamic shear stiffness as well as stretch/recoil properties with minimal immunogenicity, all of which are significant in colon anastamoses.

Disclosed herein is a method of connecting disrupted tissue, comprising, a) applying an effective amount of a photothermally responsive bioadhesive composition comprising an ELP and a light absorbing chromophore to disrupted tissue in need of being connected; and b) applying an effective amount of a directed light beam to the photothermally responsive bioadhesive composition and/or the tissue.

Also disclosed herein is a method of laser tissue welding, comprising, a) applying an effective amount of a photothermally responsive bioadhesive composition comprising an ELP and a light absorbing chromophore to disrupted tissue in need of being welded; and b) applying an effective amount of a directed light beam to the photothermally responsive bioadhesive composition and/or the tissue.

Also disclosed herein is a method of tissue repair, comprising, a) suturing a tissue with fibers comprising a photothermally responsive composition comprising an ELP and a light absorbing chromophore; and b) optionally, applying an effective amount of a photothermally responsive bioadhesive composition comprising an ELP and a light absorbing chromophore to the sutured site; and c) applying an effective amount of a directed light beam to the sutures and/or to the tissue, and optionally to the photothermally responsive bioadhesive composition.

Also disclosed herein is a method of treating colorectal disease, comprising, a) applying an effective amount of a photothermally responsive bioadhesive composition comprising an ELP and a light absorbing chromophore to disrupted colorectal tissue; and b) applying an effective amount of a directed light beam to the photothermally responsive bioadhesive composition and/or the tissue.

In one aspect, instead of using light absorbing chromophore, in the methods described herein, energy absorbing materials, such as magnetic particles can be used. The particles can be nanoparticles. Suitable magnetic particles include, but are not limited to iron nanoparticles (iron oxide). The magnetic particles can be magnetothermal particles. When such particles are used directed magnetic or radio frequency methods are used rather than a directed light beam as described in the methods herein.

In one aspect, the bioadhesive composition can comprise at least 0.5%, 1%1 3%, 5%, 10%, 15%, 20%, 25% or 30% of a light absorbing chromophore. For example, the bioadhesive composition can comprise at least 0.5%, 1%, 2%, 4%, 5% or 8% of a light absorbing chromophore. The preferred loading was suggested at approximately 5% of light absorbing chromophores.

In another aspect, the bioadhesive composition can comprise between about 0.5%, 1%, 2%, 4%, 5%, or 8% of a light absorbing chromophore. For example, the bioadhesive composition can comprise between about 2%-8% and 3%-6% of a light absorbing chromophore.

In one aspect, the light absorbing chromophore generates heat once it absorbs light of an appropriate wavelength. For example, gold nanorods generate heat once they absorb light from a laser, such as a argon laser. In one aspect, the heat generated from the light absorbing chromophore produces a bulk temperature, such as a tissue temperature and/or bioadhesive temperature, of at least 55° C., 60° C., 65° C., 70° C., 75° C., 80° C., 85° C. or 90° C. Preferably, the heat generated from the light absorbing chromophore produces a tissue temperature or bioadhesive temperature of at least 65° C. In one aspect, the bulk temperature can be reproducibly produced.

In one aspect, the light absorbing chromophores crosslink the ELP through the heat generated from the absorption of energy through the directed light beam. In one aspect, the crosslinking connects disrupted tissue and can help the healing of wounds or cuts.

In one aspect, the light absorbing chromophore can comprise silver nanoparticles, gold nanorods, or gold nanoparticles, or mixtures thereof. For example, the light absorbing chromophore can comprise gold nanorods. In another example, the light absorbing chromophore can comprise gold nanorods, gold nanospheres, gold nanoshells, gold nanocubes, and silver nanoparticles.

In one aspect, the light absorbing chromophore has antimicrobial properties, such as anti-bacterial properties. For example, the light absorbing chromophore can be silver nanoparticles. The light absorbing chromophore can have effective antibacterial activities, for example, against *E. coli* and *Staphylococcus aureus*, shown by using the agar Kirby-Bauer disk-diffusion method.

In one aspect, an ELP comprises cysteine residues. An ELP can, for example, comprise at least 2, 4, 6, 8, 10, 12 or 14 cysteine residues. Thus, an ELP can, for example, comprise at least 2, 3, 4, 5, 6, 7, 8, 9, 10, 11, or 12 cysteine residues. In one aspect, an ELP can, for example, comprise 2, 3, 4, 5, 6, 7, 8, 9, 10, 11, or 12 cysteine residues. For example, the ELP can comprise at least 8 or 12 cysteine residues. An ELP having 8 cysteine residues can be referred to as $C_8$ELP. An ELP having 12 cysteine residues can be referred to as $C_{12}$ ELP. In one aspect, the ELP comprises 8 or 12 cysteine residues in the sequence: MVSACRGPG-[VG VPGVG VPGVG VPGVG VPGVG VPG]$_8$-[VG VPGVG VPGVG VPGCG VPGVG VPG]$_8$-WP (SEQ ID NO:1) or MVSACRGPG-[VG VPGVG VPGVG VPGVG VPGVG VPG]$_8$-[VG VPGVG VPGVG VPGCG VPGVG VPG]$_{12}$-WP (SEQ ID NO:2).

For example, cetyltrimethyl ammonium bromide (CTAB) surfactant-templated gold nanorods (GNRs) can be used to facilitate the irreversible crosslinking of cysteine-containing ELPs leading to the formation of ELP-GNR nanocomposites. These ELP-GNR nanocomposites not only retained the photothermal properties of gold nanorods, are also able to act as 'depots' for drug release.

In one aspect, the bioadhesive composition, such as a PNP-ELP nanocomposite, can reproducibly produce tissue temperature of at least 55° C. upon irradiation from a light source, for example a laser. For example, the bioadhesive composition can reproducibly produce tissue temperature of at least 55° C., 60° C., 65° C., 70° C., 75° C., 80° C., 85° C. or 90° C. upon irradiation from a light source, for example a laser. In one aspect, the bioadhesive composition can reproducibly produce tissue temperature of at least 65° C. upon irradiation from a light source.

In one aspect the bioadhesive composition can have anti-microbial properties, such as anti-bacterial properties. For example, a bioadhesive composition can comprise an anti-bacterial agent. Suitable antibacterial agents include, but are not limited to, amikacin, gentamicin, kanamycin, neomycin, netilmicin, tobramycin, paromomycin, geldanamycin, herbimycin, loracarbef, ertapenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spectinomycin, spiramycin, aztreonam, furazolidone, nitrofurantoin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, amoxicillin, ampicillin, piperacillin, ticarcillin, bacitracin, colistin, polymyxin B, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfamethizole, sulfamethoxazole, sulfanilimide, sulfasalazine, sulfisoxazole, trimethoprim, trimethoprim-sulfamethoxazole (co-trimoxazole) (TMP-SMX), demeclocycline, doxycycline, minocycline, oxytetracycline, tetracycline, clofazimine, dapsone, capreomycin, cycloserine, ethambutol, ethionamide, isoniazid, pyrazinamide, rifampicin rifabutin, rifapentine, streptomycin, arsphenamine, chloramphenicol, fosfomycin, fusidic acid, linezolid, mtronidazole, mupirocin, platensimycin, quinupristin, dalfopristin, rifaximin, thiamphenicol, tigecycline, tinidazole, and anti-microbial peptides and proteins.

In one aspect the bioadhesive composition may comprise active agents. For example, an active agent may be an MMP inhibitor. For example, an MMP inhibitor can be doxycycline. MMP inhibitors include tissue inhibitor of metalloproteinases (TIMPs), TIMP-1, TIMP-2, TIMP-3, and TIMP-4; zinc chelating groups including hydroxamates, carboxylates, thiols, and phosphinyls, Minocycline, marimastat (BB-2516), a broad-spectrum MMP inhibitor, and cipemastat (Ro 32-3555), an MMP-1 selective inhibitor.

MMP overexpression breaks down early tissue formed during anastomoses in the colon, which compromises healing[42, 56]. Thus, the bioadhesive compositions disclosed herein can be employed for diffusion-based as well as laser-triggered localized delivery of MMP inhibitors (e.g. doxycycline). Other suitable active agents include, but are not limited to a soluble factors, such as cytokines or growth factors. For example, a soluble factor can comprises FGF (fibroblast growth factor), TGF-beta, EGF, VEGE, or other factors known as growth factors or cytokines, or known to be involved in wound healing and repair. In another aspect, the active agent can be encapsulated. In another example, the active agent is not encapsulated. In one aspect, the active agent is located within the bioadhesive composition.

In one aspect, the bioadhesive composition can comprise extracellular matrix material(s). Non-limiting examples of extracellular matrix material(s) include collagen and/or silk proteins. Thus, the bioadhesive composition can comprise collagen and/or silk proteins.

In one aspect, the bioadhesive composition can comprise ELP-collagen, ELP-silk, ELP-fibrin, or ELP-polymer, and conjugates and blends thereof. For example, the bioadhesive composition can comprise ELP-collagen. In another example, the bioadhesive composition can comprise ELP-silk. In yet another example, the bioadhesive composition can comprise ELP-fibrin. In yet another example, the bioadhesive composition can comprise ELP-polymer.

In one aspect, the directed light beam can be a laser, such as an argon laser. The directed light beam preferably has a wavelength that is compatible with the light absorbing chromophore. The light absorbing chromophore absorbs the energy from the directed light beam and reliably heats up to desired temperature. The intensity of the direct light beam can be adjust to achieve suitable temperatures in the tissue and bioadhesive material, such as 65° C., 70° C., 75° C., 80° C., 85° C., or 90° C. It is possible to tailor the directed light beam so absorption of multiple chromophore in the bioadhesive material is achieved. For example, a laser can be tailored to the absorption of both silver and gold nanoparticles in a bioadhesive composition.

In one aspect, the tissue in need of being welded is from a cut or sore. In another aspect, the tissue in need of being welded is from surgery. In an aspect, the tissue in need of welding is from a traumatic disruption of the tissue.

In one aspect, the bioadhesive composition is suitable for suturing. For example, the bioadhesive tissue can be in the form a string or other suitable suture material for suturing. For example, the bioadhesive composition is in the form of a fiber. One singular advantage of the nanocomposites is that it is possible to generate fibers from ELP-based materials using electrospinning, electrospraying and wet-spinning techniques[81,85]. PNP-ELP plasmonic fibers (up to 60 μm dia.), for example which may be generated using wet spinning or 0.2-3 μm using electrospinning, may be used for simultaneously suturing the wound and subsequent LTW for added strength. The bioadhesive composition suture material may be used alone or in addition to bioadhesive compositions disclosed herein. For example, a bioadhesive suture material may be used to attach the free ends of the disrupted tissue, and a liquid bioadhesive composition may be used to coat the repair site, or a sheet of bioadhesive composition material may be wrapped around the exterior of the repair site. The area may then undergo tissue welding to form a tight seal at the repair site.

In one aspect, the bioadhesive material can comprise cells. The cells in the bioadhesive material can promote the connection of tissue upon being applied to a site to be welded. Cellularized and non-cellularized PNP-ELP nanocomposite compositions of the present invention can be employed for LTW of intestinal tissue alone and in combination with suturing using known suture material. Fibers of PNP-ELP nanocomposite compositions may be used for simultaneous suturing and laser tissue welding of tissue, such as colorectal tissue.

In one aspect, the directed light beam is a laser, such as a Titanium-Sapphire laser, Krypton laser, Ruby laser, Chromium doped chrysoberyl (alexandrite) laser, Divalent samarium doped calcium fluoride (Sm:CaF2) laser, AlGaInP laser, AlGaAs laser, Vertical cavity surface emitting laser (VCSEL). In one aspect, the wavelength of the light from the directed light source is in the near infrared. In another aspect, the directed light source is manipulated to match the absorption wavelength of the light absorbing chromophore. For example, the directed light beam can comprise a wavelength of light that matches the absorption of gold nanorods. In one aspect, the disrupted tissue is colorectal tissue. In another aspect, the disrupted tissue can be a blood or lymphatic vessel in the body. For example, the disrupted tissue can be bowel. In another example, the disrupted tissue can be uniary tract tissue. In another example, the disrupted tissue can be skin. In another example, the disrupted tissue can be from a cut, such as a surgical cut.

In one aspect, the directed light beam can be in continuous wavelength mode. In another aspect, the directed light beam can be in pulse wavelength mode.

In an aspect, the bioadhesive composition further comprises cells. Suitable cells include but are not limited to, NCM460, fibroblasts, stem cells, or mixtures thereof.

In one aspect, the disrupted tissue in need of being welded is from sore or cut. For example, the disrupted tissue in need of being welded is from a surgical cut or from a traumatic disruption of a tissue or organ. In one aspect, the disrupted colorectal tissue results from removal of a section of the colon during surgery.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

Figure 1B:
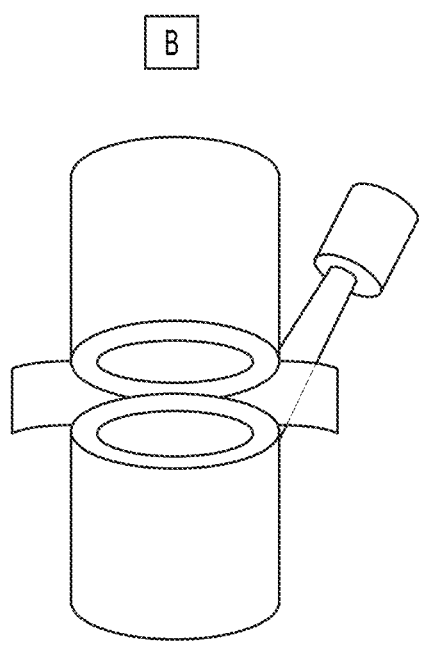
Figure 1C:
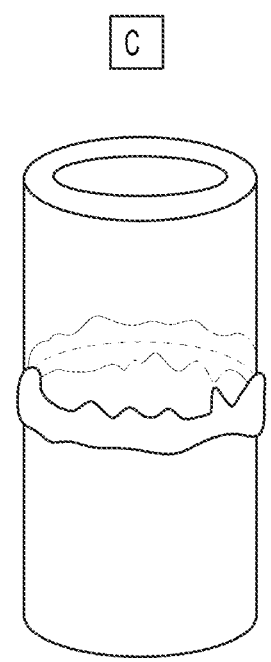

The following exemplary compounds of the invention were synthesized. The Examples are provided herein to illustrate the invention, and should not be construed as limiting the invention in any way. The Examples are typically depicted in free base form, according to the IUPAC naming convention A. General Methods The examples below demonstrate the production of PNP-ELPs suitable for LTW as shown in FIGS. 1A-1C. The PNP-ELP bioadhesive materials with plasmonic nanoparticles, for example gold nanorods and silver nanoparticles, can maximize the efficacy and control of the photothermal effect. As shown below, the ELP, cross-linked with PNPs, can improve the anastomoses strength and the elasticity of the PNP-ELP nanocomposite will allow for recovery of tissue, such as colon function.

Huang et al. previously generated GNR-ELP nanoassemblies[2] and plasmonic nanocomposites[1], described in references, each of which is hereby incorporated herein by reference in its entirety. Huang et al. showed that such nanocomposites possess photothermal properties, support cell culture, and can be employed for light triggered administration of hyperthermia and small-molecule drugs[1]. Additionally, phase separation and formation of nanocomposites have been studied. (Langmuir, manuscript accepted for publication, Feburary 2012).

Dallas et al. previously produced silver nanoparticle-ELP nanocomposites. In addition to their plasmonic properties, the known antibacterial properties[44] of silver make them attractive in wound healing, Dallas et al. is hereby incorporated herein by reference in its entirety.

The examples below indicate that PNP-ELP nanocomposites can be used simultaneously for laser tissue welding, drug (e.g. doxycycline) delivery, and tissue healing in a multifunctional manner. Thus, one can engineer the ELP sequence and modulate nanoparticle type (e.g. GNR or silver nanoparticle) and composition in order to obtain desired physicochemical, mechanical, and photothermal properties.

B. Example 1

Generation of Bioadhesive Compositions

Huang et al. previously generated $C_n$ELPs ($C_n$ indicates n number of cysteines in the ELP repeat sequence) using recursive directional ligation, expressed, and purified as described previously[2], which is hereby incorporated by reference in its entirety. . C2ELPs were self-assembled on gold nanorods by means of stable gold-thiol bonds, leading to formation of photothermally responsive GNR-C2ELP nanoassemblies or liquid-phase dispersions[2]. Engineering additional cysteines (n=8, 12) resulted in phase separation and formation of GNR-ELP viscoelastic nanocomposites. Briefly, GNR-$C_{12}$ELP nanoassemblies were first generated at 4° C. Incubation of these nanoassemblies at 37° C., i.e. above the transition temperature ($T_t$) of $C_{12}$ELP ($T_t$ of $C_{12}$ELP=30.4° C.), resulted in temperature-triggered, entropy-dominated phase transition of the polypeptide, which, in concert with GNR-thiol, and intra- and intermolecular cysteine-cysteine cross-linking, resulted in the irreversible formation of maroon-colored, plasmonic nanocomposites[1] (see, FIG. 2). The nanocomposites were characterized using UV-Vis spectroscopy, FTIR, response to NIR laser irradiation, and dark-field imaging in order to investigate their optical and photothermal properties (FIGS. 3A-3E)[1,2].

The nanocomposites demonstrated a robust photothermal response in response to NIR laser due to uniform distribution of GNRs throughout the ELP matrix. Small-molecule drugs could be encapsulated in the GNR-ELP nanocomposite. Laser irradiation resulted in release of the drug from the nanocomposite, though not wishing to be bound by any particular theory, it was thought due to structural changes in the ELP at the higher temperatures brought about by the GNR photothermal effect, indicating that the nanocomposites can be used for laser-triggered drug delivery.

(1) Mechanical Properties

Figure 4A:
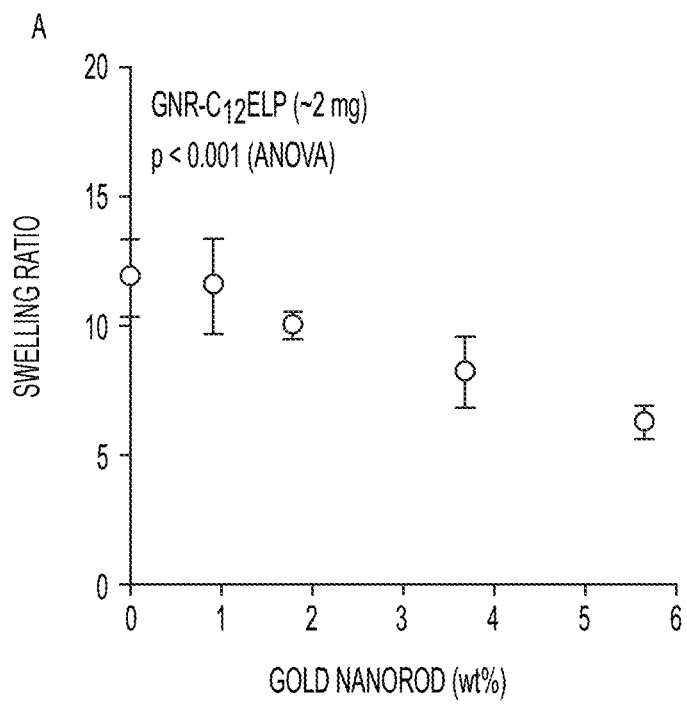
FIGS. 4A-4C show the mechanical properties of nanocomposites at various GNR weight ratios. (A) Swelling ratio. (B) Absolute shear modulus. (C) Loss angle.
Figure 4B:
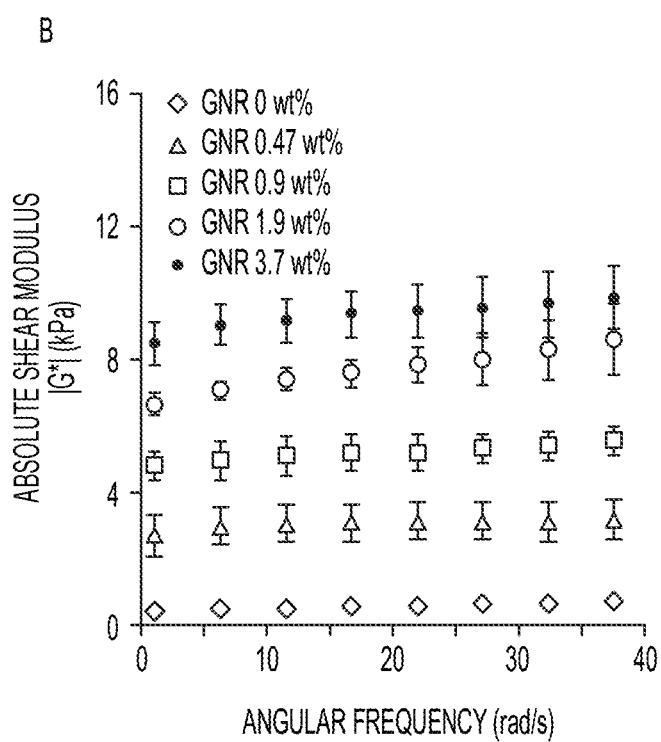
Figure 4C:
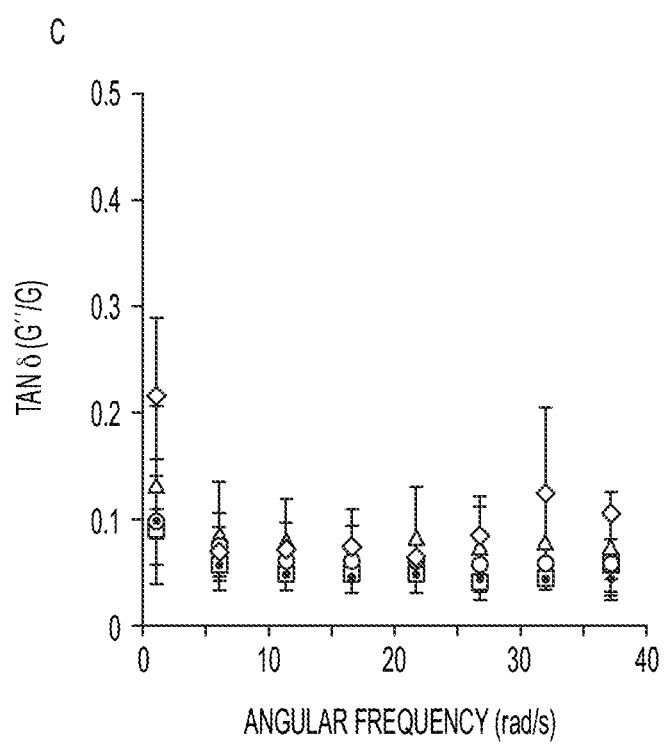

The PNP content in the bioadhesive compositions can be varied in order to modulate the mechanical properties, leading to different swelling ratios and stiffness of the nanocomposite. Suture materials typically posses a tensile strength of ~130 N/mm$^{2[57]}$ which is much higher than the human colon tissue (~0.4-2 N/mm$^2$)[58]. Although much stronger, sutures cannot recover the mechanical strength of the ruptured tissue to its original intact value. The mismatch in mechanical strength may be partly responsible for sub-optimal performance. On the other hand, tensile strength of aortic elastin (~1 N/mm$^{2[59]}$), synthetic elastin (~0.2 N/mm$^{2[60]}$), glutaraldehyde cross-linked elastin films (0.3-0.8 N/mm$^{2[59]}$) and electrospun tropoelastin fibers (~0.36 N/mm$^{2[61]}$), are similar to that of the colon. For example, FIG. 4A shows the swelling results for the disclosed bioadhesive materials. A statistically significant (p<0.001) reduction of swelling ratio (defined: swollen mass ($M_s$) over dry mass ($M_d$)) from 12 to 6 was observed as the GNR weight percentage increased from 0 to 5.4 wt % at 25° C. This is likely due to the cross-linking facilitated by GNRs leading to the formation of rigid network to prevent swelling. The absolute shear modulus (|G*|) and loss angle (δ), representing stiffness and internal energy dissipation of the nanocomposite under dynamic loading, respectively, are investigated as a function of GNR concentration (see FIGS. 4B and 4C). Both, swelling ratio and stiffness can be modulated by altering the composition of PNPs in the nanocomposites. In addition, tensile strength, elastic modulus, strain at failure, and resilience are determined, in order to identify those compositions whose mechanical properties match those of the colon.

(2) Proposed Characterization and Photothermal Property Characterization of PNP-ELP Nanocomposites.

Figure 5A:
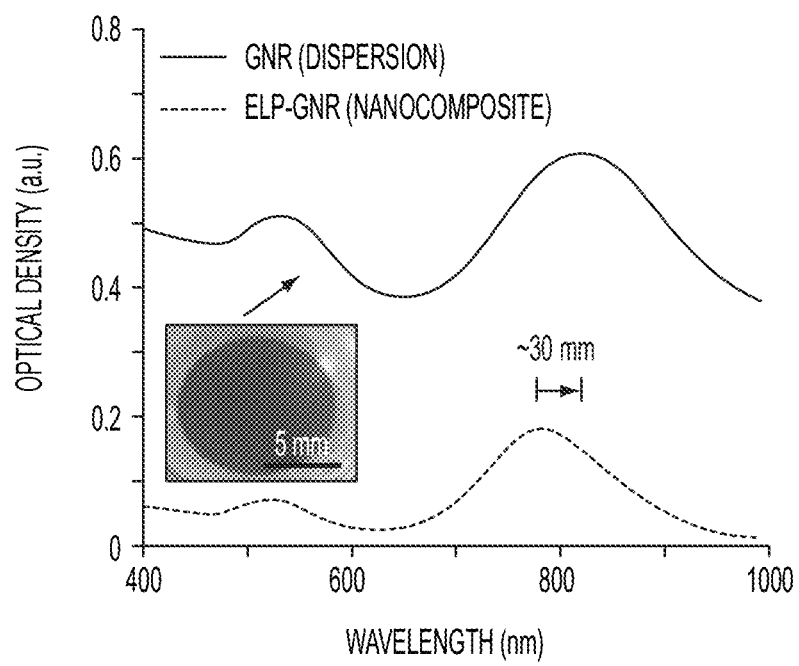
FIGS. 5A-5C show the light absorption spectra of GNR (30 μg)-ELP (1.5 mg) (maroon (shown as dark in figure) inset; left), silver nanoparticle or AgNP (15 μg-ELP (2 mg) (silvery white (shown as bright in figure)inset; middle), and hybrid GNR (30 μg)-AgNP (15 μg-ELP (2 mg) (light red inset (shown as dark in figure); right) nanocomposites. Nanocomposites retain the plasmonic properties of the nanoparticles. GNRs (~15 nm diameter, ~50 nm length) and spherical AgNP (~60 nm radius).
Figure 5B:
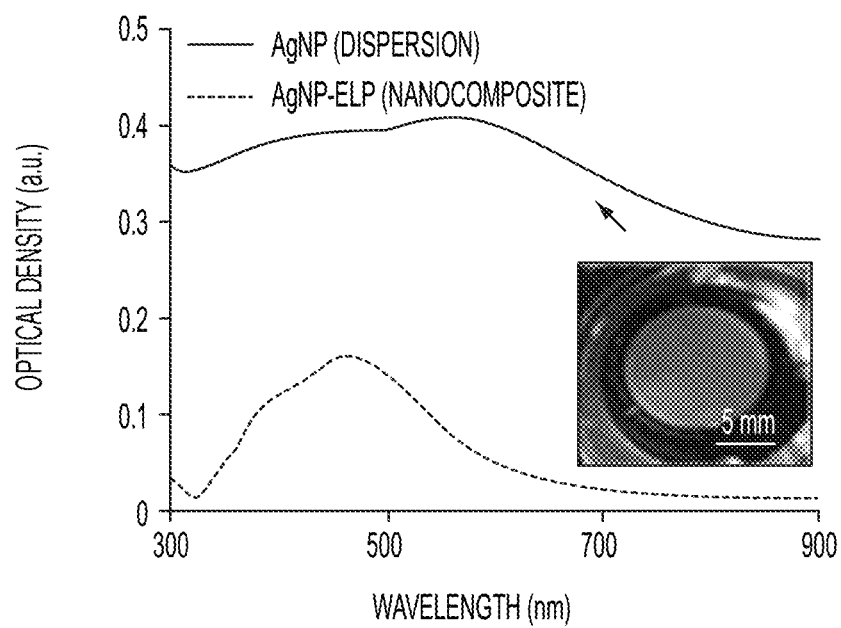
Figure 5C:
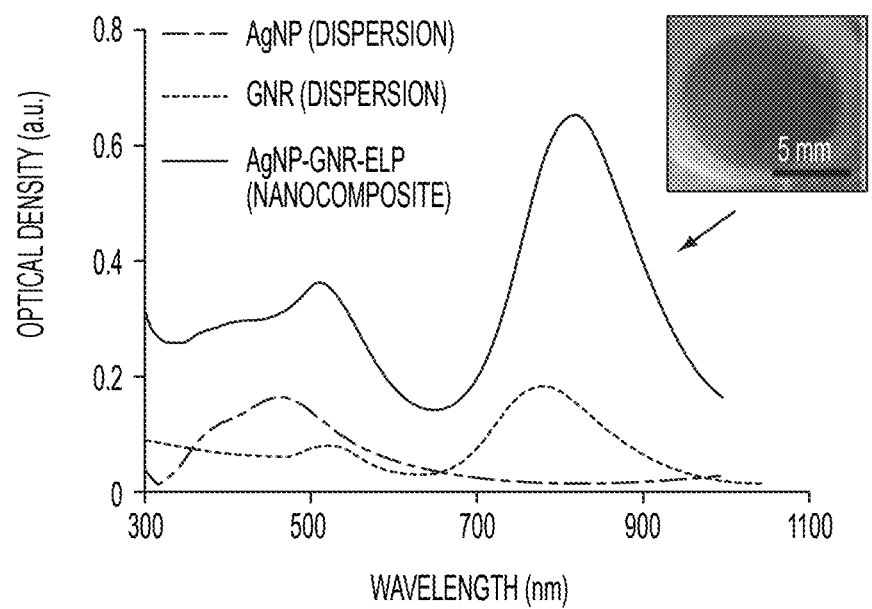

It is typically necessary to heat tissues from 60° C. to 95° C. in order to achieve maximal anastomosis strength[26, 39-41, 62] GNR-ELP nanocomposites was modulated in order to obtain a bulk temperature of ~45° C. following laser irradiation, although the temperature directly in the path of the laser may be higher. In order to identify materials that result in weld temperatures of 65-75° C., the (i.e. GNR or silver), nanoparticle weight % (range: 1-20%) within the ELP matrix, laser power density, and laser irradiation time, can be altered. For example, GNR-ELP, AgNP-ELP, and hybrid GNR-AgNP-ELP nanocomposites were generated and these nanocomposites absorb light at different wavelengths (see FIGS. 5A-5C) The temperature can be monitored using a J-thermocouple and an IR camera. An evaluation of mechanical properties (e.g. swelling ratio, absolute shear modulus and loss angle) of nanocomposites will be carried out at different temperatures (25-75° C.), in order to investigate the integrity of these materials. Any potential deformation[63, 64] of the plasmonic nanoparticles following laser irradiation can be investigated using Field Emission Scanning Electron Microscopy (FE-SEM), TEM and UV-Vis spectroscopy. Optimization of PNP content, laser energy and type can be employed to identify conditions where the localized temperature is controlled below a shape transformation threshold, and the temperature near the laser area is ~65-75° C. to avoid tissue shrinkage and discoloration[65]. The spatiotemporal temperature distribution following photothermal response of the nanocomposites can be modeled based on the Pennes bioheat equation using an approach described in Hunag et al. ACS Nano 2010. Stability of PNP-ELP nanocomposites in PBS are evaluated for at least six months by monitoring release of nanoparticles (e.g. using NIR absorbance for gold), and polypeptide fragments (e.g. using gel-permeation chromatography or GPC) in the supernatant. Different amounts of doxycycline (100-1000 µg) will be encapsulated and diffusion-based and laser triggered release of the drug from the nanocomposites are determined as describer[1].

C. Example 2

Laser Tissue Welding

Figure 6A:
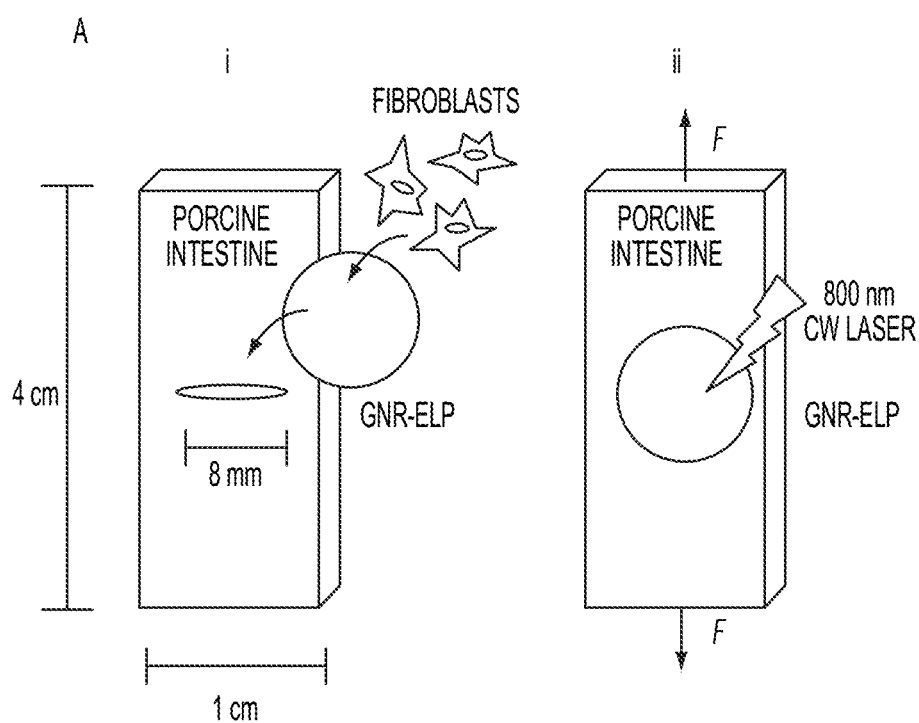
FIGS. 6A-6C show the determination of breaking force after nanocomposite-assisted laser tissue welding of porcine intestine. (A). Full thickness incision (~8 mm in width) was applied at the center of the rectangular intestine sections (~0.1 cm thick, 4×1 cm). The GNR-ELP nanocomposite was applied on top of the serosa layer and across the full thickness incision with full contact. Laser light (20 W/cm$^2$, 1 mm/second) was applied vertically. (B) The maximum force (N) achieved prior to sample breaking was recorded and reported as ultimate tensile strength (UTS, kPa). n=1-12. (C) Ultimate tensile strength of tissues before and after laser tissue welding using cellularized nanocomposites. Fibroblasts were cultured on top of nanocomposites for 1, 4 and 7 days.
Figure 6B:
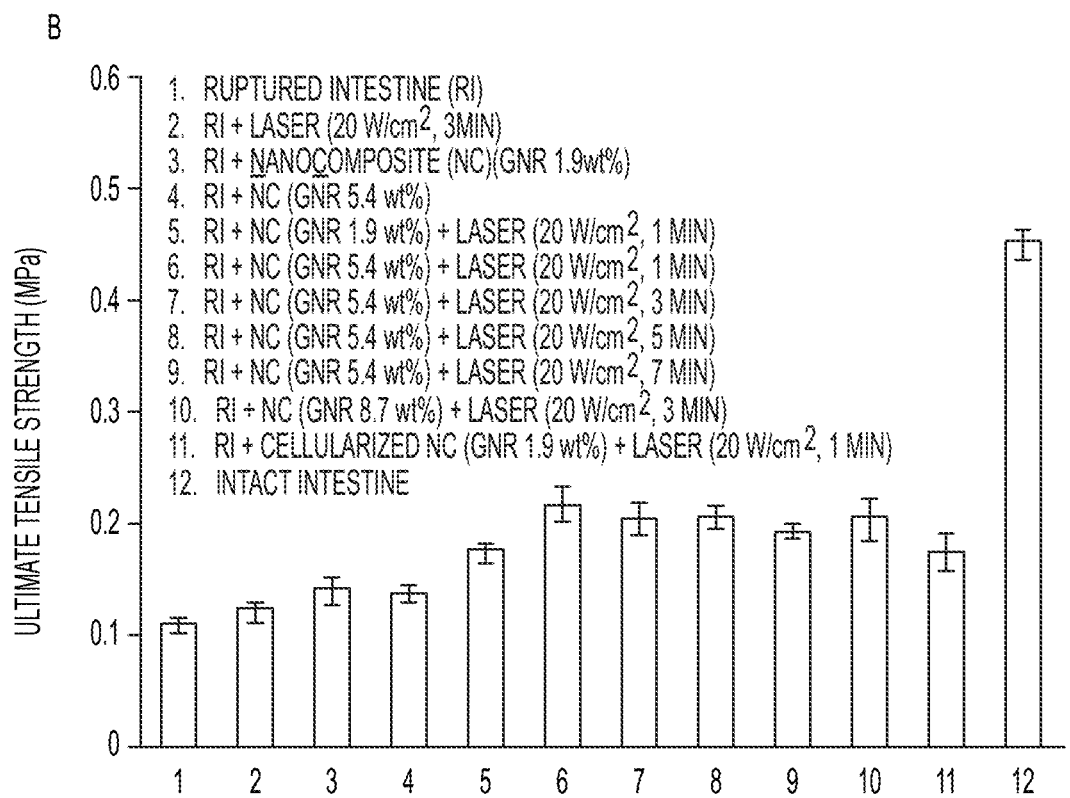

GNR-ELP nanocomposites were employed for the ex-vivo laser tissue welding of porcine intestines. GNR-ELP nanocomposites (10 mm diameter, thickness=247±65 µm) were irradiated fully across with 800 nm CW laser at a rate of 1 mm/sec. This treatment resulted in enhancing the mechanical strength (breaking force) of ruptured intestinal tissue to up to 47% of its original intact form (see FIGS. 6A-6C). The results, with a limited parameter set (laser irradiation time, GNR amount, etc.), show the potential of GNR-ELP nanocomposites for LTW of intestinal/colorectal tissues.

(1) Cellularized PNP-ELP Nanocomposites for Laser Tissue Welding.

Figure 7A:
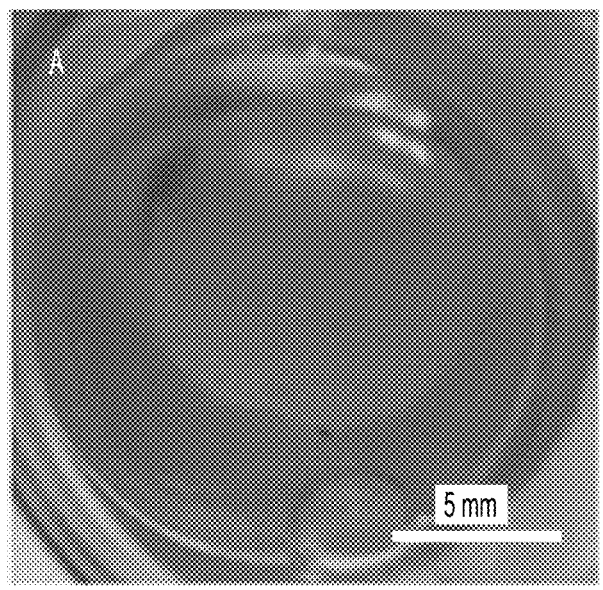
FIGS. 7A-7C show GNR-ELP nanocomposite cellularized with 3T3 murine fibroblasts. Fluorescence (Live-Dead stain) and confocal microscopy show the viability of encapsulated cells at 72 h (live cells: brighter).
Figure 7B:
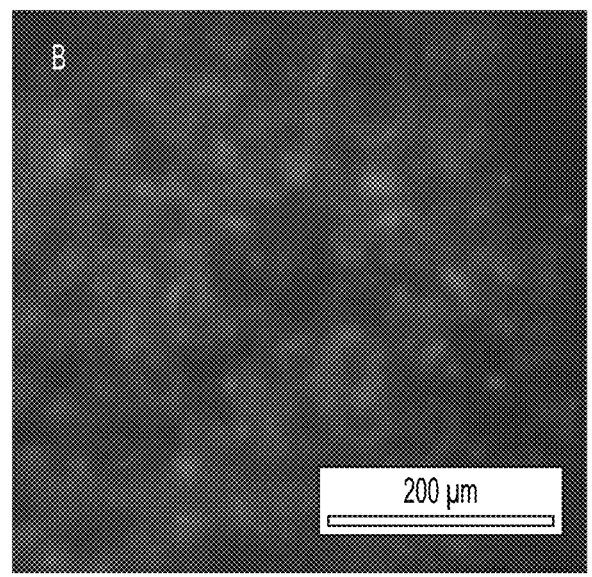
Figure 7C:
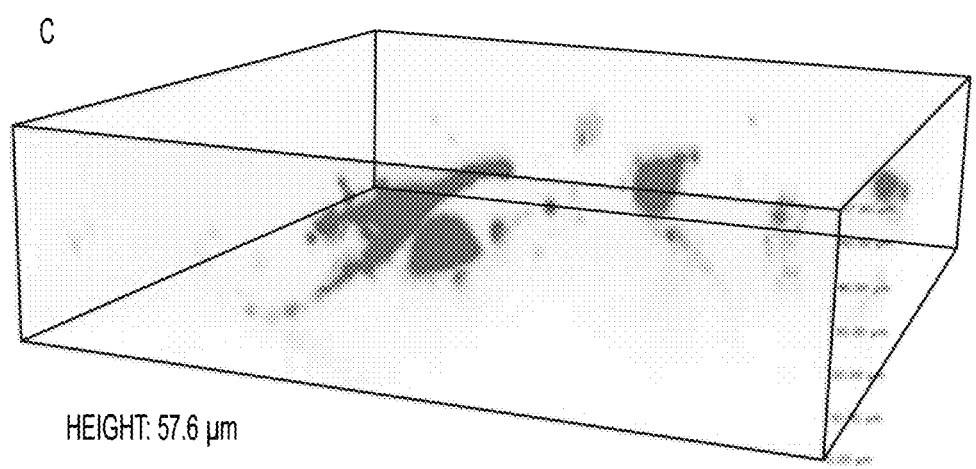

Fibroblast-cellularized hydrogels demonstrate collagen deposition[72] which increases mechanical stiffness[73] of the hydrogel compared to the acellular material. Cellularized nanocomposites facilitate rapid collagen deposition that imparts mechanical strength to the weld promoting tissue regeneration. To show this, fibroblast proliferation was sustained for up to 2 weeks with minimal loss of viability. PEGylated-GNR based nanocomposites showed 55-77% attachment of fibroblasts at 24 h compared to tissue culture well plates (control). Encapsulation of 3T3 fibroblasts (see FIGS. 7A-7C) and their proliferation (see FIGS. 8A-8D) within GNR-ELP nanocomposites was confirmed by confocal fluorescence microscopy. It is therefore possible to cellularize PNP-ELP nanocomposites to promote tissue repair.

(2) Other Experiments

The normal colon epithelial cell line, NCM460[74], available from INCELL Corporation, LLC, are employed for encapsulation within PNP-ELP nanocomposites; fibroblasts and 50-50% co-cultures of the two cell types are used. Cell viability and proliferation of NCM46 cells from the nanocomposite towards the peripheral areas of the nanocomposites are characterized using fluorescence microscopy. If necessary, PNPs are functionalized with cationic polymers (e.g. 1,4C-1,4Bis) which were previously synthesized[75, 76] to promote cell attachment. As discussed above, it was demonstrated that the ability to culture murine fibroblast (NIH 3T3) cells both, on top of as well as inside nanocomposites (prepared using both PEG-modified and unmodified GNRs) with negligible cytotoxicity (see FIGS. 7A-7C).

Cellularized nanocomposites are employed in concert with a scratch wound healing assay to assess cell migration and proliferation as a healing model[77]. The cellularized PNP-ELP nanocomposite are used as not only a bioadhesive solder for laser tissue welding of colorectal tissue for enhanced mechanical strength, but also to facilitate tissue regeneration, mediated by soluble factores[78, 79] (FIGS. 8A-8D). Given the role of fibroblast growth factor (FGF), TGF-(3, and EGF in wound healing and repair, ELISA will be used to determine the expression of growth factors/cytokines[80] from the nanocomposites.

Figure 8A:
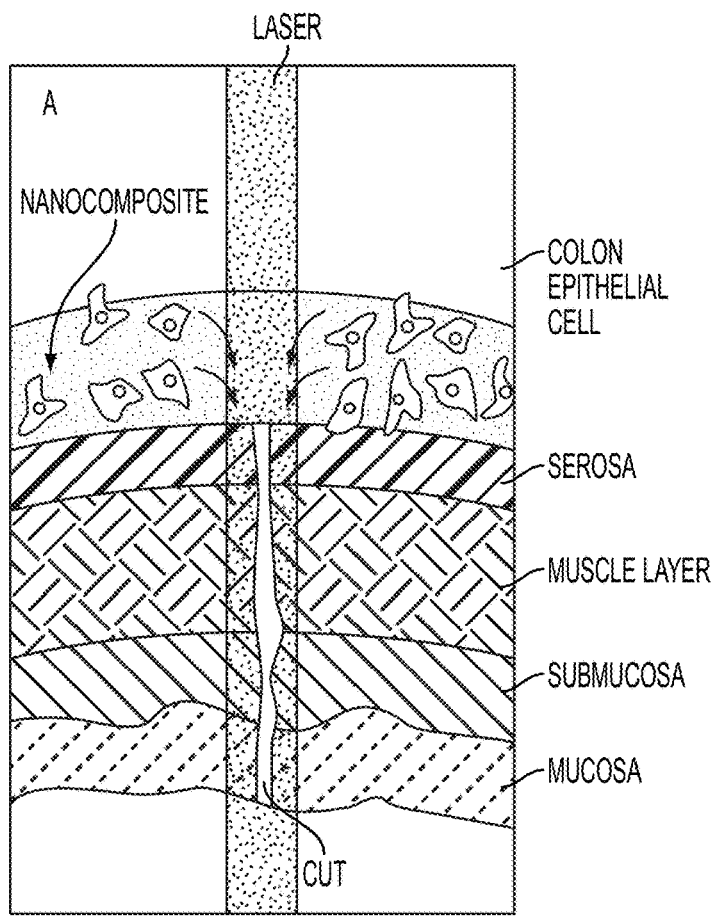
FIGS. 8A-8D show (A) Schematic of cellularized PNP-ELP nanocomposite-mediated LTW after colorectal surgery. Viable cells outside the laser path can promote regeneration after anastomosis. (B) PC3-PSMA cells in the laser path (dotted line) on GNRELP nanocomposite die (red) due to hyperthermia; peripheral cells are alive (green). (C) Cell proliferation (mm) from nanocomposite. C1 and C2 show cell migration on day 2 and day 3 (phase contrast microscopy). (D) Proliferation distance in mm versus time in days is shown in C3.
Figure 8B:
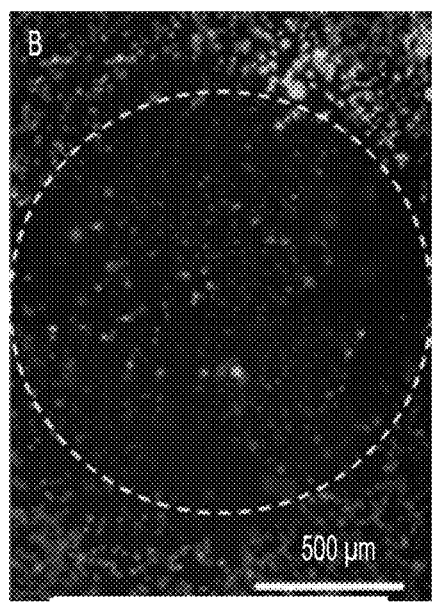
Figure 8C:
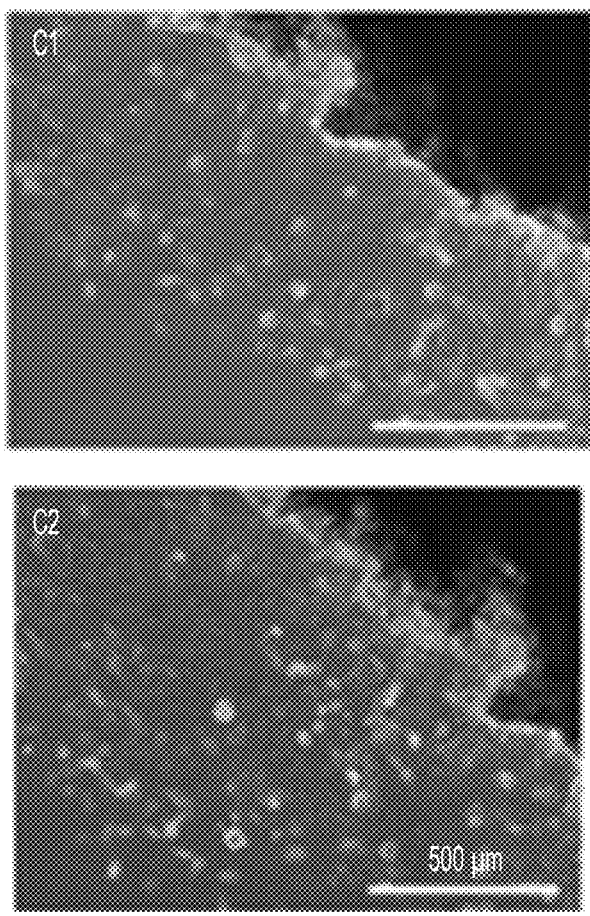
Figure 8D:
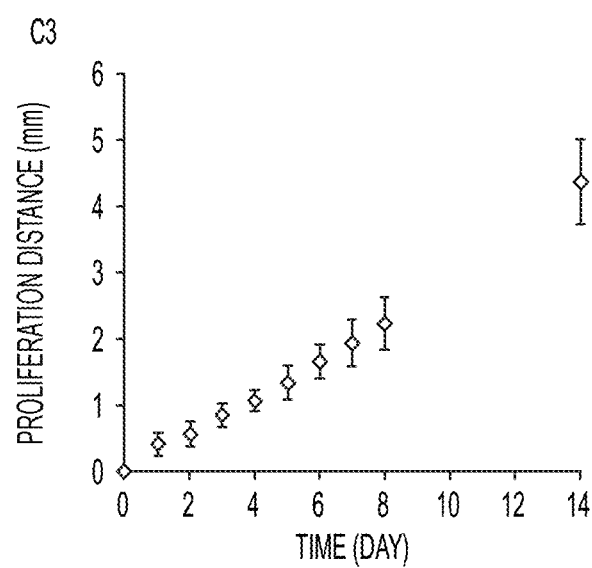

Laser irradiation of nanocomposites placed on top of the tissue incision results in a fluid-tight seal and enhances the mechanical integrity of anastomosis. Live cells outside the laser path migrated towards anastomosis site and growth factors can facilitate tissue regeneration. Both, cell viability outside the direct laser path (green-fluorescent cells) and active migration have been demonstrated using PC3-PSMA human prostate cancer cells and NIH 3T3 murine fibroblasts, respectively (FIG. 8B). In all cases, the bursting pressure, tensile strength of cellularized scaffolds upon laser tissue welding are compared to non-cellularized scaffolds, sutured tissue, and the original non-damaged tissue. Collagen and histology staining are carried out as described previously.

Optimized nanocomposites are employed to maximize laser anastomosis strength of porcine colorectal tissues. Ex vivo fresh tissues are purchased from Animal Technologies Inc., Texas. Laser-welded tissues undergo (i) breaking force (tensile strength) measurement using TA XT plus Texture Analyser (Texture Technology Corp., NY) (see FIG. 6A) and (ii) leaking and bursting pressure tests[29] to evaluate the mechanical integrity and weld strength of the anastomosis site. Specifically, full-thickness incisions (fully/partially across the tissue) are applied on rectangular intestinal sections (1×4 cm) and tubular intestinal sections (~7 cm in length). The tissues undergo breaking force and bursting pressure testing following LTW. Changes in tensile strength, at various time points after LTW, are correlated to histologic findings. Histologic analyses are performed on the cross sections of repaired tissues, using hematoxylin and eosin (H&E) staining, to evaluate the morphology of collagen, nanocomposite and wound edge[39]. Conventional suture anastomoses and fibrin glue[71] will be used as controls.

D. Example 3

Bioadhesive Materials and Properties (1) Materials

Sodium borohydride, powder, reagent grade, no less than 98.5%, cetyltrimethylammonium bromide (CTAB), 95%, gold (III) chloride trihydrate ($HAuCl_4 \cdot 3H_2O$), +99.9%, L-ascorbic acid, reagent grade were purchased from Sigma. Crystalline silver nitrate was purchased from Spectrum and dithiothreitol (DTT) was purchased from EMD. All materials were used as received without further purification.

(2) GNR Synthesis

Gold nanorods were synthesized using the seed-mediated method as described by El-Sayed et al.[22]. Briefly, the seed solution was prepared by adding 0.6 ml of iced-water-cooled sodium borohydride (0.01 M) to reduce a solution of 5 ml (0.2 M) of CTAB in 5 ml (0.0005 M) auric acid with vigorous stirring. The growth solution was prepared by reducing 5 ml (0.2 M) CTAB in 5 ml (0.001 M) auric acid containing 280 µl (0.004 M) silver nitrate with 70 µl (0.0788 M) L-ascorbic acid solution. Seed solution (12 µl) was introduced to 10 ml of growth solution, which resulted in the generation of GNRs after 4 h of continuous stirring. The nanorods were centrifuged once, the supernatant was removed, and re-suspended in deionized (DI) water to remove extra free CTAB molecules. This method was employed for generating GNRs that possessed absorbance maxima ($\lambda_{max}$) in the near-infrared region of the light absorption spectrum.

(3) Synthesis, Expression & Purification of Cysteine-Containing ELPs

Cysteine-containing ELPs, $C_8ELP$ and $C_{12}ELP$, were generated via the recursive directional ligation method described previously[23]. $C_8ELP$ and $C_{12}ELP$, respectively, contain 8 and 12 cysteine residues in the sequence: MVSACRGPG-[VG VPGVG VPGVG VPGVG VPGVG VPG]$_8$-[VG VPGVG VPGVG VPGCG VPGVG VPG]$_{8(or\ 12)}$-WP (SEQ ID NO:1 and SEQ ID NO:2, respectively). Briefly, oligonucleotides encoding the ELPs were cloned into pUC19 vector, followed by cloning into a modified version of the pET25b$^+$ expression vector at the sfiI site. *Escherichia coli* BLR(DE3) (Novagen) was used as a bacterial host. Both $C_8ELP$ and $C_{12}ELP$ were expressed, purification lyophilized and stored at room temperature, as described previously[23].

(4) Determination of Transition Temperature

The transition temperatures ($T_t$) of $C_8ELP$ and $C_{12}ELP$ were characterized by monitoring the absorbance at 610 nm as a function of temperature with an UV-visible spectrophotometer (Beckman DU530) in 0.5× phosphate-buffered solution (PBS). Briefly, 1 ml of $C_8ELP$ (0.5 mg/ml in 0.5×PBS) and 1 ml of $C_{12}ELP$ (1 mg/ml in 0.5×PBS) were prepared and placed in 1.5-ml disposable cuvettes. The temperature of $C_nELP$ (n: the number of cysteines in the ELP repeat sequence; n=8/12) was tuned by placing the $C_nELP$-contained cuvette into a Precision 288 Digital Water Bath (Thermo Scientific) and was recalibrated by FLUKE 54 II (Type K) thermometer before absorbance measurement. The absorbance of $C_nELP$ was monitored at 610 nm with an UV-visible spectrophotometer (Beckman DU530) immediately after withdrawing the cuvette out of the water bath. The $T_t$ is defined as the temperature at which the absorbance of $C_nELP$ solution reaches 50% of the maximum value. The temperature response of the $C_8ELP$ and $C_{12}ELP$ indicated $T_t$ values of 31.3 and 30.5° C., respectively.

(5) Generation of $C_nELP$-GNR Nanoassemblies

Two different ELPs, $C_8ELP$ and $C_{12}ELP$, containing 8 and 12 cysteines in the ELP repeat sequence, respectively, were employed in the current study. Cysteine-containing ELPs were self-assembled on GNRs (CTAB-GNRs) whose peak absorbance ($\lambda_{max}$) was at 800 nm. ELPs were self-assembled on GNRs overnight at 4° C., leading to formation of the nanoassemblies ($C_nELP$-GNR assemblies) via gold-thiol bonds. Briefly, 1 ml of $C_nELP$ (2 mg/ml in 1×PBS) was mixed overnight with 1 ml of GNR (optical density at 800 nm=0.5) dispersion in DI water at 4° C. to form a 2-ml $C_nELP$-GNR dispersion (1 mg/ml in 0.5×PBS). Prior to self-assembly, 20 mg of reductacryl resin (EMD Biosciences, Inc.) was added to ELP (1 ml) solution for 15 min in order to reduce the cysteines in the polypeptide[24]. Reduced ELP was separated from the resin by centrifugation at 13,000 rpm for 10 min, and immediately added to GNRs at a volumetric ratio of 1:1 and stirred overnight at room temperature. Equivalent concentrations of GNRs (without self-assembled $C_nELP$) and $C_nELP$ (without GNRs) were used as controls in the experiments. $C_nELP$ (2 mg/ml in 1×PBS) was added into DI water at a 1:1 volume ratio, to form $C_nELP$ solution (1 mg/ml in 0.5×PBS; $C_nELP$ alone). GNRs in DI water (1 ml; $\lambda_{max}$=800 nm; optical density at 800 nm=0.5) were added to an equal volume (1 ml) of 1×PBS in order to bring the final concentration to 0.5×PBS (GNR alone).

(6) Formation of $C_n$ELP-GNR Matrices

A volume of 1 ml $C_8$ELP-GNR, and $C_{12}$ELP-GNR solutions (1 mg/ml, 0.5×PBS, optical density: 0.25), in 1.5-ml microcentrifuge tubes, was incubated in a 37° C. water bath for 6 h in order to allow the phase separation of GNR-$C_n$ELP, resulting in the formation of the matrix at the bottom of the tubes. The matrices were subsequently cooled and stored at room temperature. GNRs (without self-assembled $C_n$ELP) and $C_n$ELP (without GNR) solutions were used as controls in the experiment. To study the kinetics of matrix formation, the absorption spectra of the supernatant of both $C_8$ELP-GNR and $C_{12}$ELP-GNR dispersions were determined at different times using a temperature-controlled plate reader (Biotek Synergy 2) during water heating (bath incubation) and cooling. The spectra were typically measured between 300 and 999 nm. The $C_8$ELP-GNR and $C_{12}$ELP-GNR matrices are stable at room temperature for at least 1 month.

(7) Dissolution of $C_8$ELP-GNR Matrices

For dissolution experiments, the PBS supernatants were removed from individual $C_n$ELP-GNP matrices and replaced with equivalent volumes of 10 mM dithiothreitol solution for 30 min at 4° C., following which, absorbance spectra were determined as a function of time in order to investigate dissolution kinetics.

(8) Fourier-Transform Infrared Spectroscopy

Gold nanorods and $C_8$ELP- and $C_{12}$ELP-based matrices were loaded on a germanium-attenuated total reflectance crystal, such that they covered the central area of the crystal. The sample chamber was equilibrated to approximately 4 mb pressure in order to minimize the interference of atmospheric moisture and $CO_2$. The absorption spectrum was measured between 650 and 4,000 cm$^{-1}$ using a Bruker IFS 66 v/S FT-IR spectrometer and the background spectrum was subtracted from all sample spectra, as described previously[25].

(9) Field-Emission Scanning Electron Microscopy

Scanning electron microscopy (SEM) samples were prepared by placing $C_n$ELP-GNR matrices on a flat alumina substrate. The matrix on the substrate was allowed to dry out in open laboratory atmosphere. SEM images were obtained with an environmental field-emission SEM (PHILIPS FEI XL-30 SEM) operating an accelerating voltage of 25 kV, and several magnifications between 2500 and 20,000×.

(10) Photothermal Properties of a $C_{12}$ELP-GNR Matrix Film $C_{12}$ELP-GNR dispersion (750 µl of 1 mg/ml in 0.5×PBS; optical density: 0.25; 4° C.) in 1-mm diameter acrylic cell (homemade) was immediately incubated in 37° C., 5% $CO_2$ environment for 3 h, in order to allow matrix formation on top of a tissue culture-treated 1.5-mm diameter cover slip originally placed at the bottom of the acrylic cell. The supernatant was removed from the acrylic cell after incubation and the absorption spectrum of the $C_{12}$ELP-GNR film was determined using a plate reader (Biotek Synergy 2) at room temperature. The spectrum was measured between 300 and 999 nm at five individual times.

The photothermal properties of the matrix were determined using irradiation with a titanium CW sapphire laser (Spectra-Physics, Tsunami) pumped by a solid-state laser (Spectra-Physics, Millennia). Briefly, the excitation source was tuned to 850 nm in order to coincide with the longitudinal absorption maximum of the $C_{12}$ELP-GNR matrix. The $C_{12}$ELP-GNR matrix was placed at the bottom of a 24-well plate (Corning) with 500 µl of 1×PBS as the supernatant over the matrix. The well was irradiated with laser light at 850 nm at power densities of 20 or 25 W/cm$^2$ for 15 min, and the dispersion temperature was monitored by FLUKE 54 II (Type K) thermocouple during laser exposure. Controls with only 500 µl of 1×PBS solution in 24-well plates (i.e., without $C_{12}$ELP-GNR film) were carried out; temperature remained invariant at 24±0.5° C. after 15 min laser exposure in this case.

(11) Formation of 17-AAG-Loaded $C_{12}$ELP-GNR Matrix Film (24-Well Plate)

$C_{12}$ELP-GNR dispersion (750 µl of 1 mg/ml, 0.5×PBS, optical density: 0.25 at 4° C.), containing 750 µg of 17-AAG (LC Laboratories, MA, USA) was placed in the 1-mm diameter acrylic cell, and immediately transferred to an incubator (37° C., 5% CO2) for 3 h, allowing phase separation and formation of 17-AAGloaded $C_{12}$ELP-GNR (17-AAG-$C_{12}$ELP-GNR) matrix on top of a tissue culture-treated 1.5-mm diameter cover slip. While 6 h were previously employed for generating $C_{12}$ELP-GNR matrices (without 17-AAG), analysis of matrix formation kinetics indicated that 3 h were sufficient to generate the matrix. As a result a 3-h incubation period was used for generating 17-AAG-$C_{12}$ELP-GNR matrices in order to reduce processing times. Following incubation, the supernatant, containing free 17-AAG molecules, was removed from the acrylic cell after 3 h, and assayed for concentration using absorbance analysis. The amount of 17-AAG encapsulated in the matrix was determined from a mass balance on the drug. Briefly, absorbance values of known concentrations of 17-AAG at 335 nm were employed to generate a standard calibration curve. Following matrix formation, the concentration of 17-AAG in the supernatant was then back-calculated based on the absorbance and the calibration curve. Since the initial amount of 17-AAG is known, the amount encapsulated in the matrix was calculated as the difference of 17-AAG before and after encapsulation. The absorption spectrum of the 17-AAG encapsulated $C_{12}$ELP-GNR film was determined at room temperature using a plate reader (Biotek Synergy 2) with five individual measurements. A peak at 335 nm was used to detect encapsulation of the drug.

(12) Release of 17-AAG from 17-AAG-$C_{12}$ELP-GNR Matrices

Drug (17-AAG)-loaded $C_{12}$ELP-GNR matrices were prepared as described above and placed in a 24-well plate with 500 µl of 1×PBS. The diffusional release of 17-AAG from the matrix was monitored for 24 h. The laser beam was tuned to 2 mm in diameter for all near-infrared irradiation-triggered drug-release studies. The first laser irradiation lasted for 5 min (850 nm, 25 W/cm$^2$). Five subsequent laser irradiations (850 nm, 25 W/cm$^2$) lasted for 10 min, followed by a 20-min period without laser irradiation each. The temperature profile during the 10-min laser exposure was monitored using a K-type thermocouple.

(13) Cell Culture

The PC3-PSMA human prostate cancer cell line[26] came from the Memorial Sloan Cancer Center (NY, USA). RPMI 1640 with L-glutamine and HEPES (RPMI-1640 medium), pen-strep solution: 10,000 units/ml penicillin and 10,000 µg/ml streptomycin in 0.85% NaCl, and fetal bovine serum (FBS) were purchased from Hyclone. Serum-free medium is RPMI-1640 medium plus 1% antibiotics. Serum-containing medium is serum-free medium plus 10% FBS. Cells were cultured in a 5% CO2 incubator at 37° C. using RPMI-1640 medium containing 10% heat-inactivated FBS and 1% antibiotics (10,000 units/ml penicillin G and 10,000 µg/ml streptomycin).

(14) Cell Culture & Laser Irradiation on $C_{12}$ELP-GNR Matrices $C_{12}$ELP-GNR and 17-AAG-$C_{12}$ELP-GNR matrices on tissue culture cover slips were prepared as described previously. Prior to cell culture, the matrices were pretreated with 500-μl serum containing media in a 24-cell culture well plate (Corning) overnight in order to promote cell attachment. The serum-containing media was removed after incubation and the matrixcoated cover slips were washed twice with fresh serum-containing media. PC3-PSMA human prostate cancer cells were seeded on top of the matrices in several wells with a density of 150,000 cells/well and allowed to attach for 24 h at 37° C., in a 5% $CO_2$ incubator. For the laser irradiation experiment, the excitation source was tuned to 850 nm in order to coincide with the longitudinal absorption maximum of the $C_{12}$ELP-GNR film. Matrices with PC3-PSMA cells were exposed to laser irradiation at 850 nm at a power density of 25 W/cm$^2$ for 7 min (no laser exposure for the control samples). The solution temperature was monitored by a FLUKE 54 II (Type K) thermocouple during laser exposure. Fluorescence-based Live/Dead® assay was employed to investigate cancer cell viability 24 h after laser irradiation. Briefly, cells were treated with 4 μM ethidium homodimer-1 (Invitrogen) and 2 μM calcein AM (Invitrogen) for 30 min, and imaged using Zeiss AxioObserver D1 inverted microscope (10×X/0.3 numerical aperture objective; Carl Zeiss MicroImaging Inc., Germany). Dead/dying cells with compromised nuclei stained positive (red) for EthD-1, viable/live cells stained green for calcein AM.

(15) Results and Discussion

Cysteine-containing ELPs (CnELPs; n=8 or 12, indicating 8 or 12 cysteines in the ELP repeat sequence) were synthesized via recursive directional ligation, expressed in *E. coli*, and purified, as described previously[23]. The transition temperatures $(T_t)$[27] of $C_8$ELP and $C_{12}$ELP were determined to be 31.3 and 30.5° C., respectively. CTAB-GNRs, with maximum peak absorbance at 800 nm in the near-infrared region of the absorption spectrum, were generated using the seed-mediated growth method[22]. The cysteines in CnELPs were first reduced using Reductacryl®[24], following which they were employed to facilitate the self-assembly of polypeptide molecules on GNRs at 4° C. A red-shift of approximately 20 nm (from 800 to 820 nm) was observed in the maximal absorbance peak, which indicated the formation of CnELP-GNR nanoassemblies[23].

Figure 2:
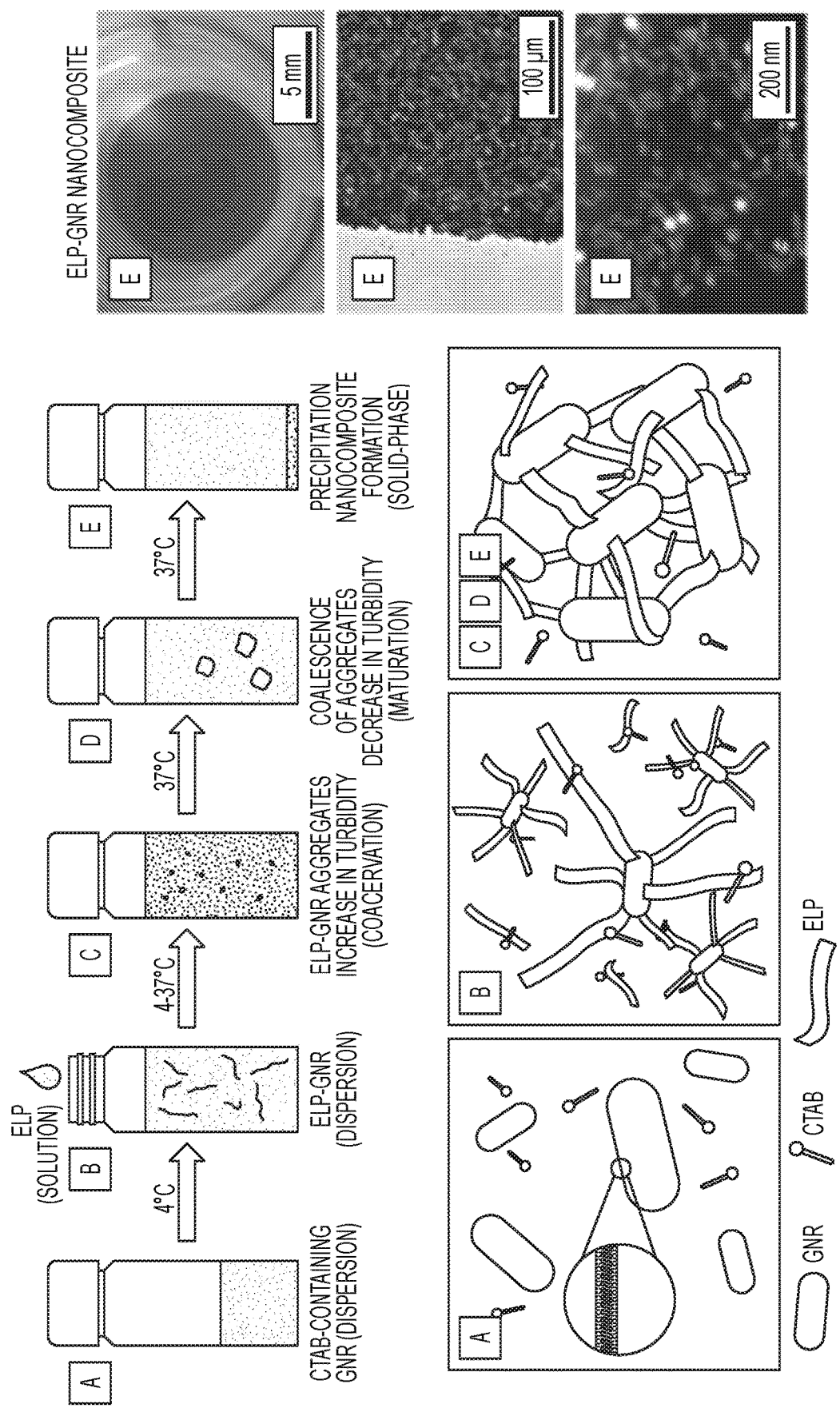
FIG. 2 shows a schematic of GNR-ELP nanocomposite formation. (A) liquid-phase GNR dispersion (B) $C_{12}$ELPs (ELPs with 12 cysteines within the polypeptide sequence) were self-assembled on gold nano rods (GNRs) resulting in GNR-ELP nanoassemblies. (C) Increasing the dispersion temperature of nanoassemblies above $C_{12}$ELP $T_t$ resulted in the formation of ELP-GNR aggregates (coacervation). (D, E) Coalescence of the aggregates and precipitation resulted in nanocomposite formation as shown in E. Environmental field-emission scanning electron microscopy confirmed uniform GNR distribution within the nanocomposite.
Figure 3A:
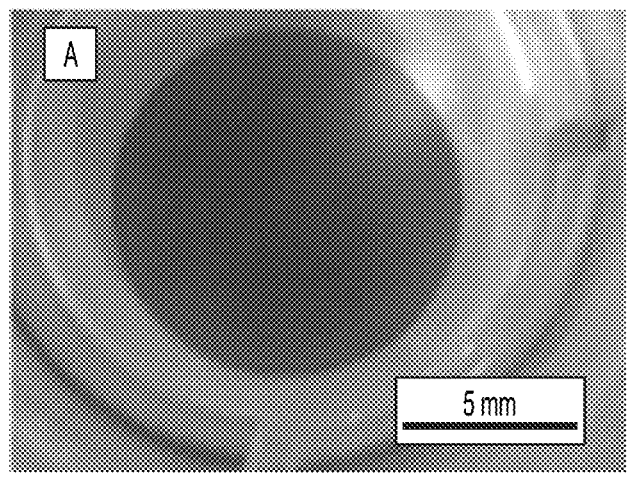
FIGS. 3A-3E show nanocomposite characterization. (A) Digital image, (B) phase contrast image (C) dark-field mage of GNR-ELP nanocomposites. (D) Photothermal response of nanocomposite upon laser exposure; temperatures of up to 43° C. were reached in ~10 min. The nanocomposites contained NIR-absorbing GNRs (E) Diffusion (left) and laser-triggered (right) release of drug (17AAG) from the nanocomposite.
Figure 3B:
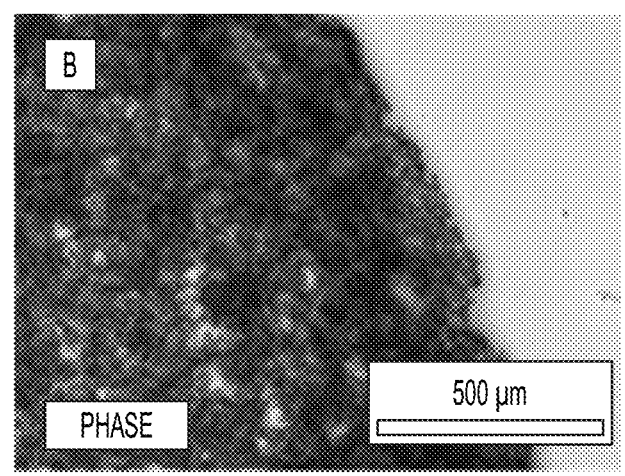
Figure 3C:
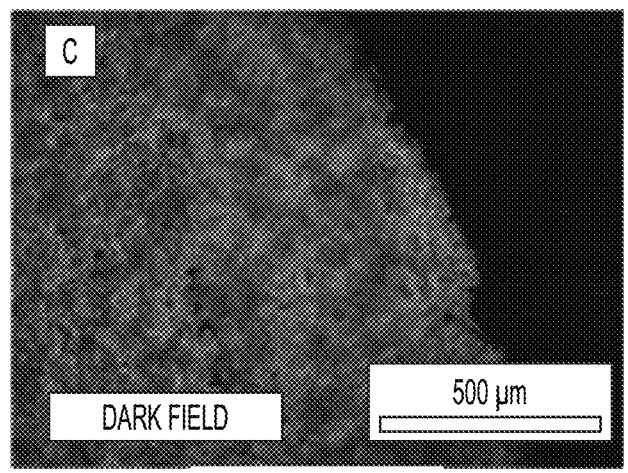
Figure 3D:
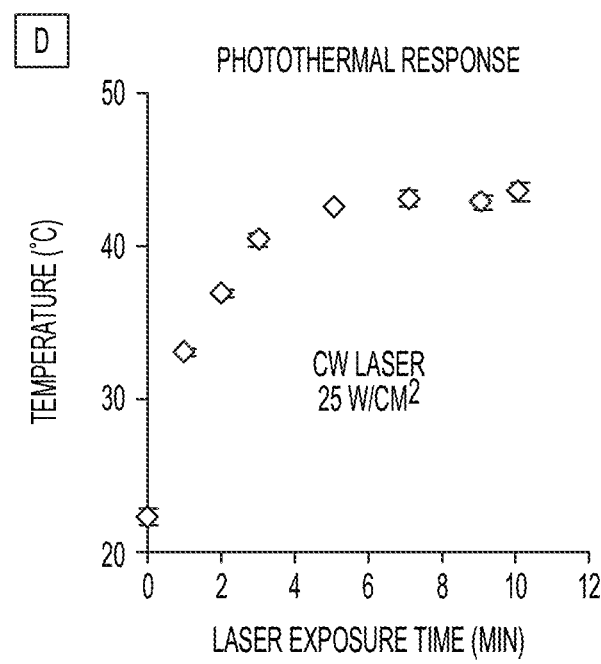
Figure 3E:
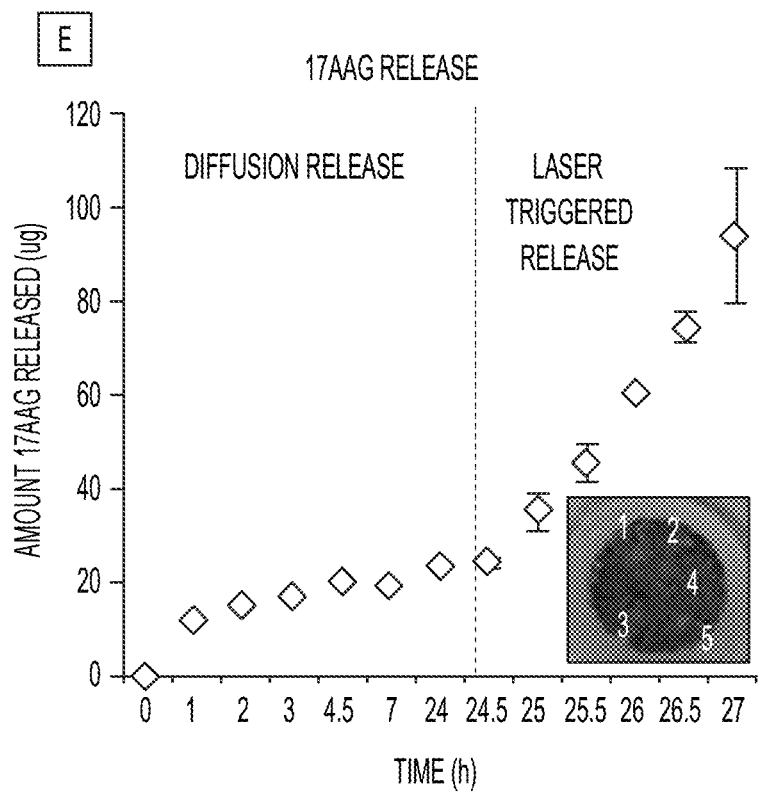
Figures 9A, 9B, 9C, 9D:
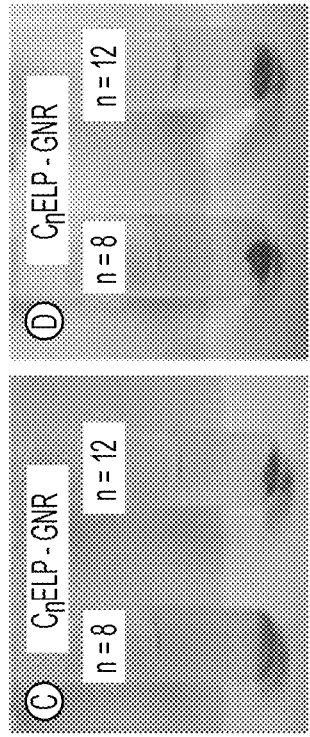
FIGS. 9A-9H show the formation of C8 elastin-like polypeptide-gold nanorod and $C_{12}$ elastin-like polypeptide-gold nanorod matrices. $C_8$ELP-GNR, $C_{12}$ELP-GNR, $C_8$ELP alone and GNR alone were incubated in a water bath (37° C.) for 6 h, followed by cooling and storage at room temperature. The transition temperature of $C_8$ELP was 31.3° C. and that of $C_{12}$ELP was 30.5° C. Digital snapshots of $C_8$ELP-GNR, and $C_{12}$ELP-GNR formation were taken at (A) 0 min, (B) 15 min (0.25 h), (C) 6 h and (D) 24 h. Images (E) and (F) show the $C_8$ELP-GNR and $C_{12}$ELP-GNR matrices. Two controls, $C_8$ELP alone and GNR alone, are shown in (G) 0 min and (H) 6 h; no matrices were formed in these cases; as expected, an increase in $C_8$ELP turbidity was observed following an increase in temperature (H). ELP: Elastin-like polypeptide; GNR: gold nanorod
Figures 9E, 9F, 9G, 9H:
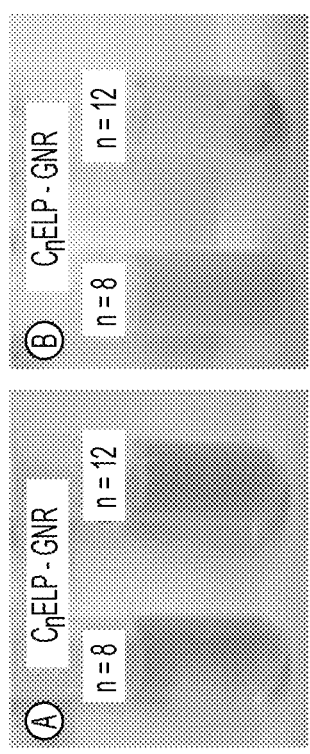
Figure 10:
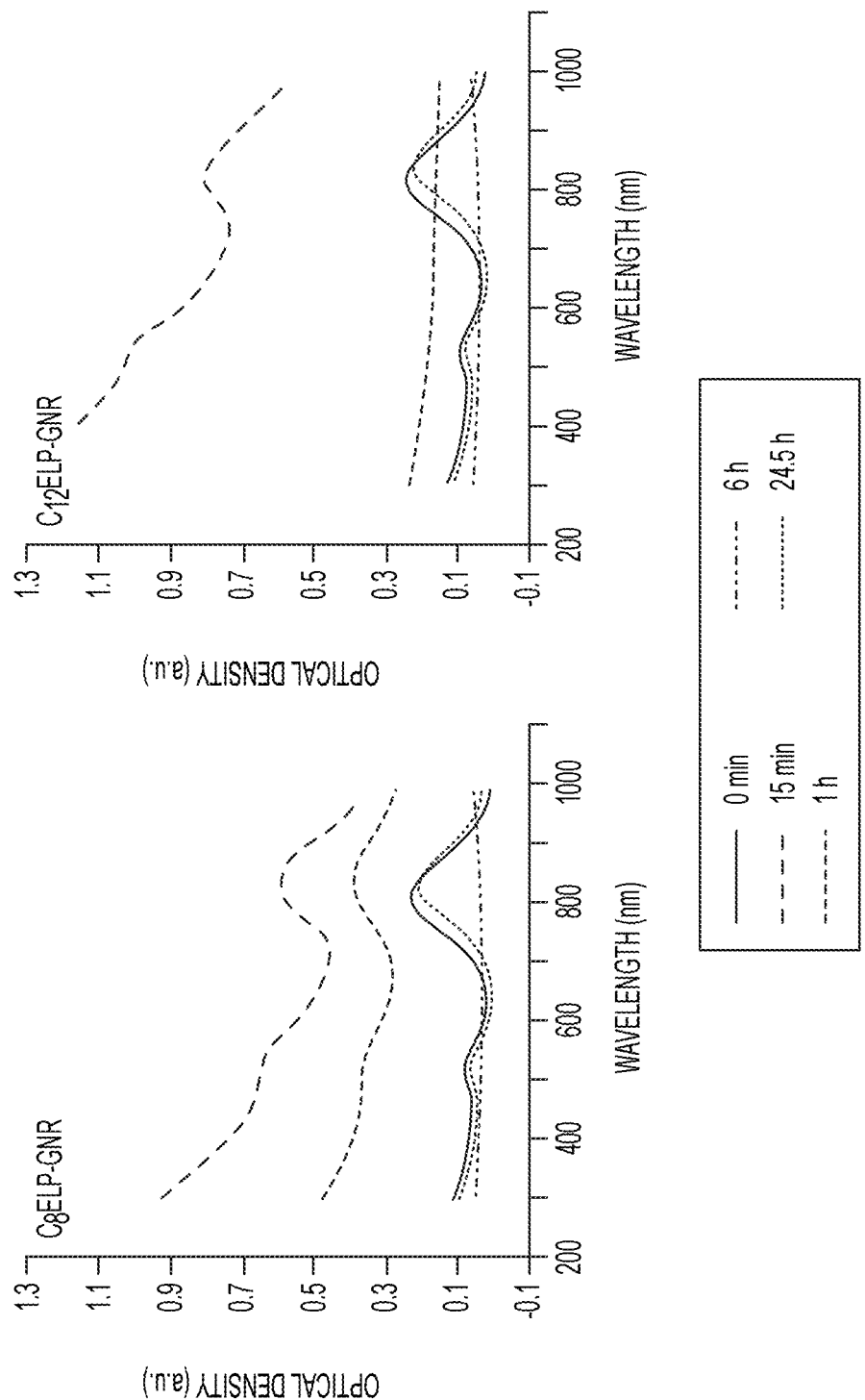
FIG. 10 shows the formation and dissolution kinetics of $C_8$ elastin-like polypeptide-gold nanorod and $C_{12}$ elastin-like polypeptide-gold nanorod matrices. The UV-vis absorbance spectra of the supernatant of CsELP-GNR and $C_{12}$ELP-GNR were monitored during the 37° C. water bath incubation stage (0-6 h), cooling/storage (6-24 h), and 30 min after adding dithiothreitol solution (24.5 h). Increase in optical density of GNR spectrum in the first hour indicates turbidity due to ELP aggregation above the transition temperature. The flat absorbance spectrum at 6 h indicates completion of the matrix formation and the absence of GNRs in the supernatant. Full recovery of the GNR spectrum at 24.5 h indicates degradability of the matrix in the presence of reducing agents.
Figure 11:
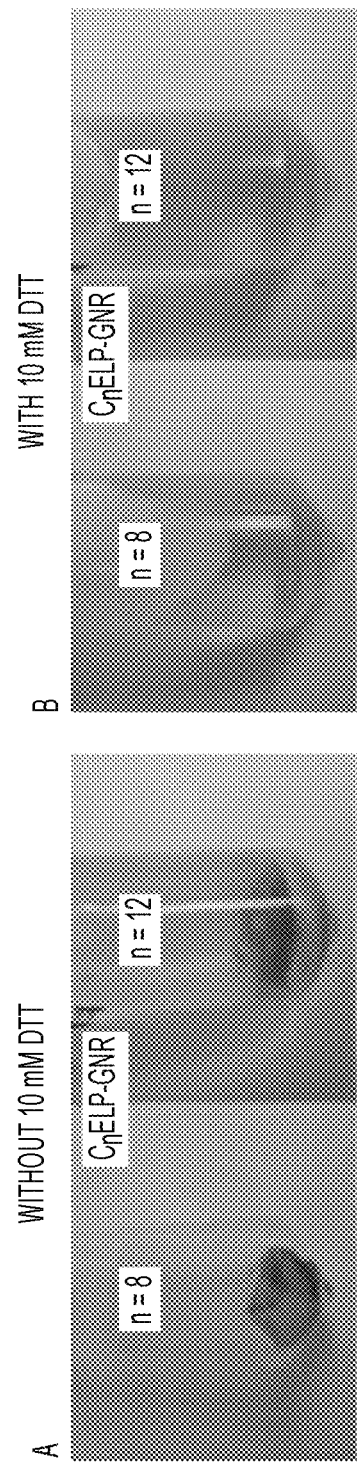
FIG. 11 shows $C_8$ elastin-like polypeptide-gold nanorod and $C_{12}$ elastin-like polypeptide-gold nanorod matrices in the presence and absence of dithiothreitol (DTT). $C_8$ELP-GNR, $C_{12}$ELP-GNR matrices were formed by incubation at 37° C. for 6 h as described above, followed by cooling and storage at room temperature (6-24 h). The supernatant was replaced with an equal volume of 10 mM DTT for 30 min at 4° C. (24-24.5 h). (A & B) $C_8$ELP-GNR and $C_{12}$ELP-GNR matrices with (A) and without (B) the presence of DTT.

The temperature transition property of $C_n$ELPs was exploited for generating $C_8$ELP-GNR and $C_{12}$ELP-GNR matrices from $C_n$ELP-GNR nanoassemblies. $C_8$ELP-GNR and $C_{12}$ELP-GNR nanoassemblies were kept at 37° C. (>$T_t$ for both ELPs) for 6 h. Incubating GNRs and $C_n$ELPs below the transition temperature results in the formation of well-dispersed 'assemblies'. However, incubation at temperatures above $T_t$ results in temperature-triggered, entropy-dominated phase transition of ELP[27, 28], in addition to GNR-thiol (from ELP cysteines), and intra- and inter-molecular cysteine-cysteine crosslinking resulting in the formation of reddish-colored plasmonic matrices (FIGS. 9A-9F). Lowering the temperature below $T_t$ did not result in dissolution of the $C_8$ELP-GNR and $C_{12}$ELP-GNR matrices (FIG. 9D), which indicated that matrix formation was not reversible with temperature, owing to extensive crosslinking. Unlike $C_n$ELP-GNR matrices, $C_n$ELP in the absence of GNRs (FIG. 9G) demonstrated a reversible phase transition process (change in optical density), but no matrix formation. GNRs in the absence of $C_n$ELP, showed no visible differences following the temperature changes (FIG. 9H). Kinetics of matrix formation were followed using the light absorption spectrum of the $C_n$ELP-GNR supernatant. Matrix formation was not observed immediately after taking the GNR-$C_8$ELP and GNR-$C_{12}$ELP nanoassemblies out of the 4° C. cooler; the light absorption spectrum at time=0 min in FIG. 2 shows a profile characteristic of the GNRs in the dispersion. The maximum optical density was 0.25 for both $C_8$ELP-GNR and $C_{12}$ELP-GNR dispersions under these conditions. Incubation of the $C_8$ELP-GNR and $C_{12}$ELP-GNR assemblies at 37° C. first resulted in an increase in optical density indicating aggregation of the GNR-CnELP nanoassemblies above the $T_t$ of the respective $C_n$ELPs; the optical densities of $C_8$ELP-GNR and $C_{12}$ELP-GNR assemblies were highest 15 min after incubation. Further incubation led to crosslinking and phase separation of the $C_8$ELP-GNR and $C_{12}$ELP-GNR matrices, leading to precipitation of the solid-phase matrix. Precipitation from the liquid dispersion resulted in the sequestration of both GNRs and the ELP in the solid phase matrix. This, in turn, is manifested as a decrease in optical density or absorbance of the supernatant (FIG. 10).

Figure 12:
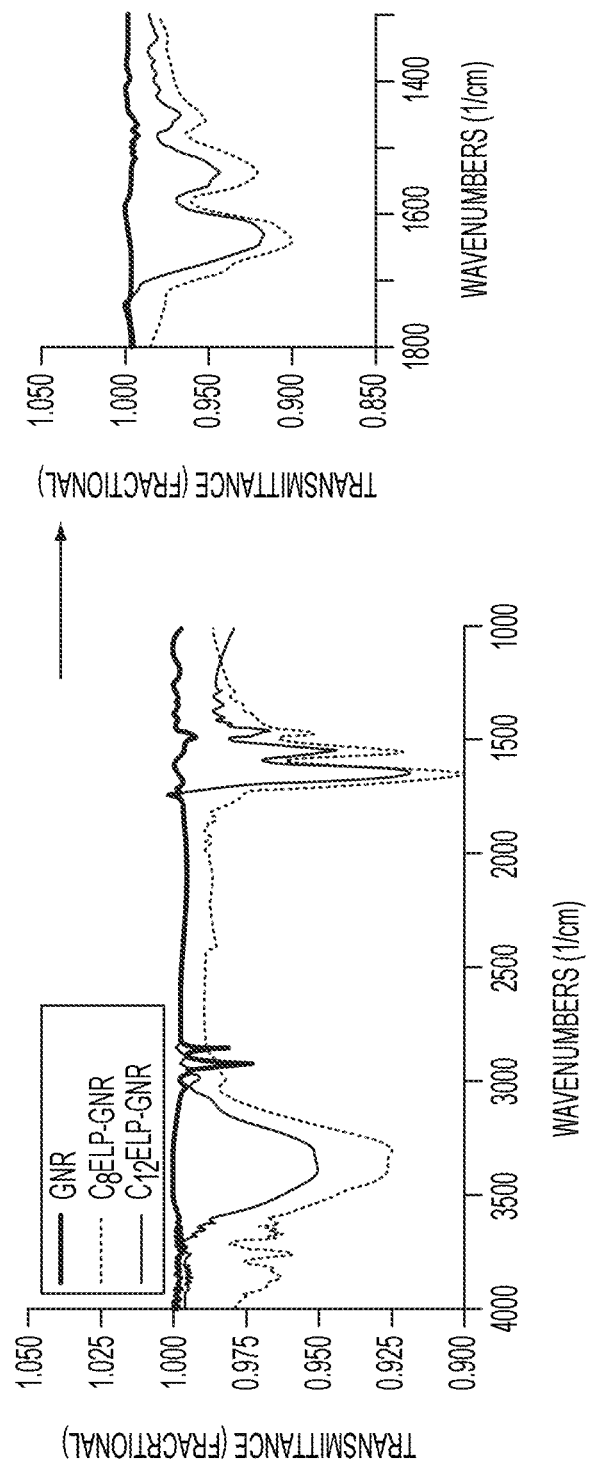
FIG. 12 shows the Fourier-transform infrared (FT-IR) spectrum of gold nanorod, $C_8$ elastin-like polypeptide-gold nanorod and $C_{12}$ elastin-like polypeptide-gold nanorod matrices. Fourier-transform infrared (Bruker Vacuum FT-IR IFS 66v/S) spectroscopy of CsELP-GNR and $C_{12}$ELP-GNR matrices indicating characteristic peaks at wave numbers of 3500-3000 $cm^1$, corresponding to the N—H stretching vibrations, 1660 $cm^1$, corresponding to the C=O stretches in the amide functionality (amide I peak), and a peak at 1550 $cm^1$, which is the combination band of N—H bending and C—N stretching vibrations (amide II peak). Cetyltrimethylammonium bromide(CTAB)-GNR shows peaks at 2850 and 2917 $cm^1$, which reflect the symmetric and asymmetric C—H stretching vibrations, respectively. No peaks were observed in the 2550-2600 $cm^1$ region, which indicates the absence of the S—H bond
Figure 13:
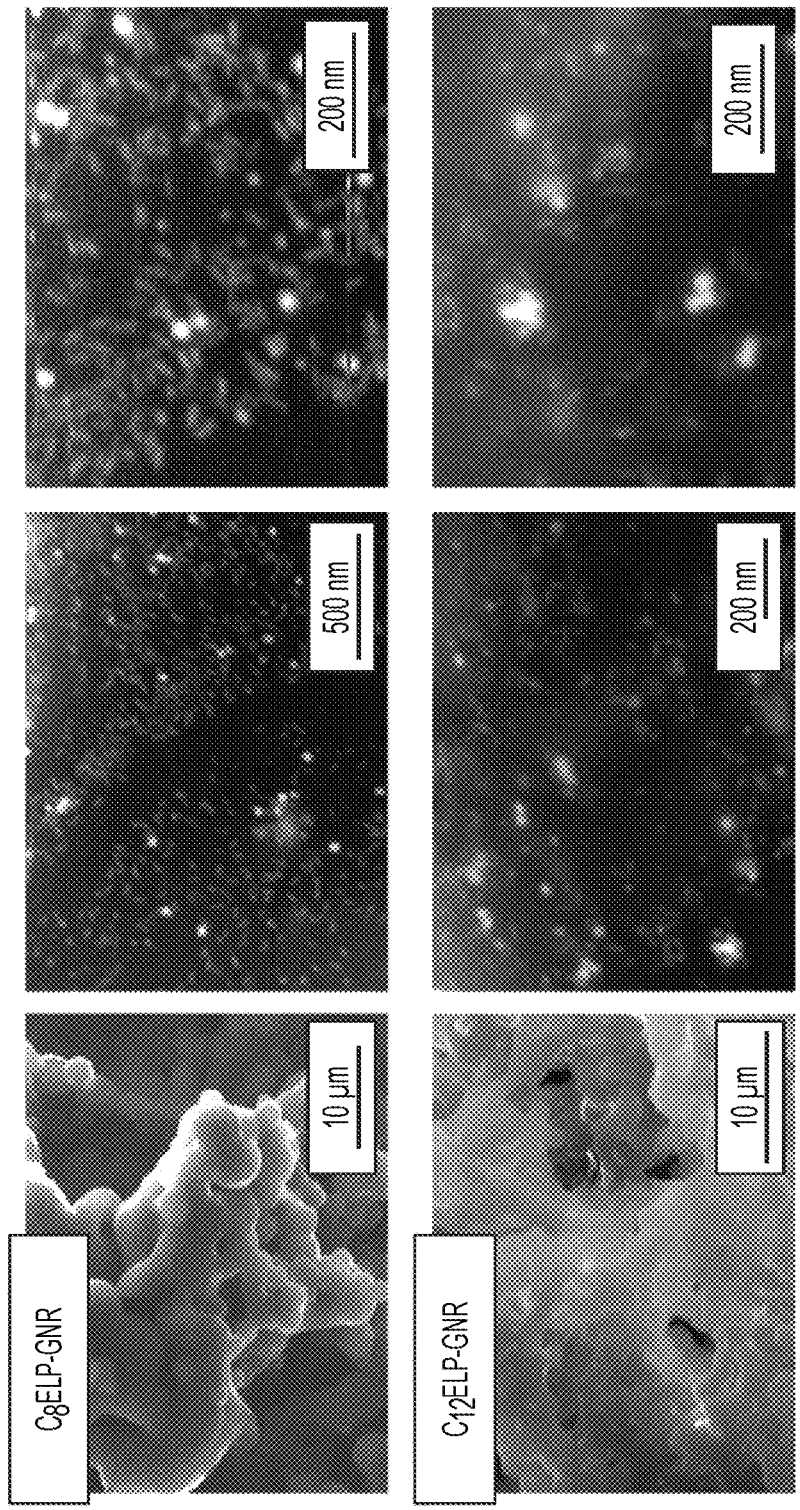
FIG. 13 shows scanning electron microscope images of $C_8$ elastin-like polypeptide-gold nanorod and $C_{12}$ elastin-like polypeptide-gold nanorod matrices. Environmental field-emission scanning electron microscopy (Philips FEI XL-30 scanning electron microscope operating an accelerating voltage of 25 kV) images indicate a fairly uniform distribution of GNRs throughout $C_8$ELP-GNR and $C_{12}$ELP-GNR matrices.

Fourier-transform infrared spectroscopy for $C_8$ELP-GNR and $C_{12}$ELP-GNR nanocomposites indicated a combination of N—H bending and C—N stretching vibrations (amide II peak) at wave number 1550 cm$^{-1}$, a peak corresponding to the C=O stretches in the amide functionality (amide I peak) at 1645 cm$^{-1}$, and a band corresponding to the N—H stretching vibrations, at 3200 and 3000 cm-1 (FIG. 12), which are characteristic of ELP spectra[29]. Field emission SEM images showed that GNRs (~50 nm in length) were well dispersed in the matrices (FIG. 13), indicating the possibility that the matrices were able to demonstrate stable plasmonic/photothermal properties. The absorbance spectrum of the $C_{12}$ELP-GNR matrix (FIG. 14) showed the transverse (520 nm) and red-shifted longitudinal peak (850 nm) characteristic of GNRs, indicating that the matrices indeed demonstrated plasmonic properties due to the uniform distribution of the GNRs. Photothermal properties of $C_n$ELP-GNR matrices were investigated by recording the temperature of PBS supernatant (500 μl) above the matrix in 24-well plates. Temperatures in each case reached their respective steady-state values (~46° C.) 5 min following laser irradiation, consistent with our previous observations with GNRs[23,30,31]; the steady-state temperatures did not change following the relatively minor change in power density from 20 to 25 W/cm$^2$.

Figure 15:
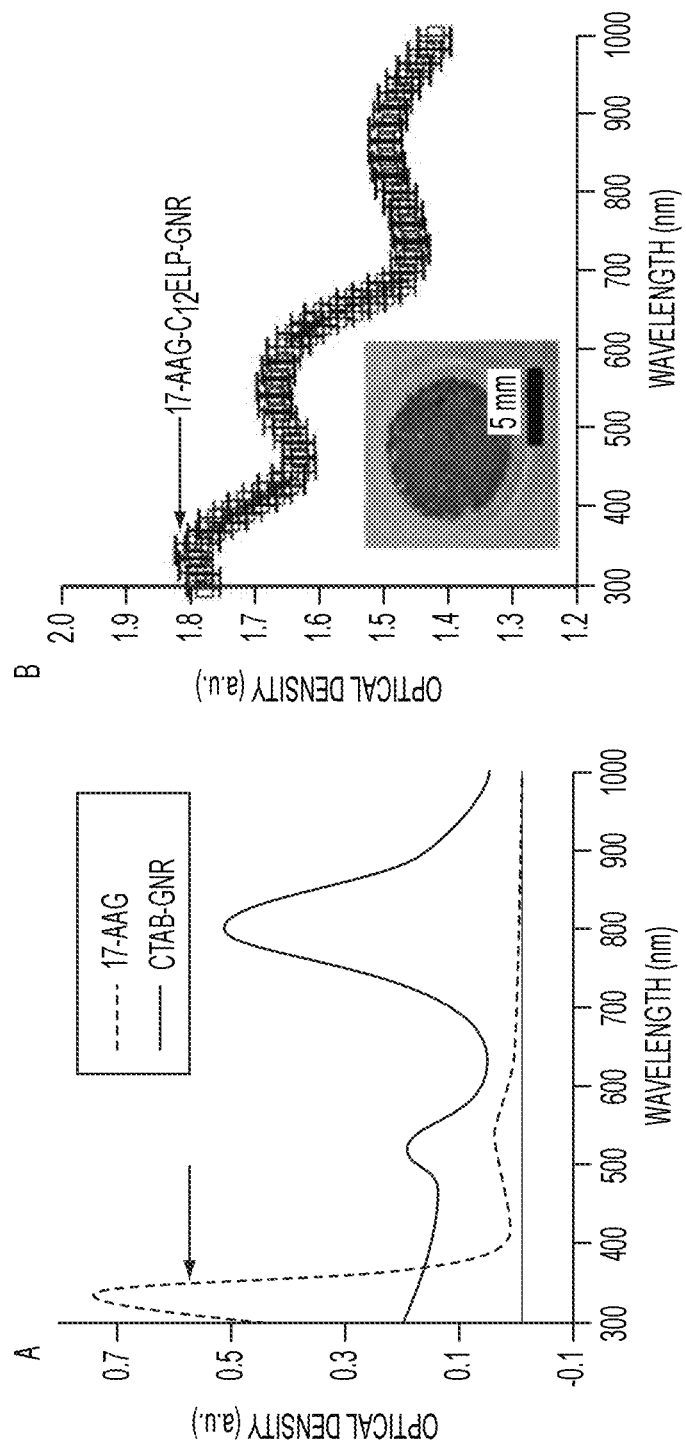
FIG. 15 shows spectrum of 17-AAG-loaded $C_{12}$ elastin-like polypeptide-gold nanorod matrices. $C_{12}$ELP-GNR matrices loaded with the heat-shock protein (HSP) 90 inhibitor drug, 17-AAG for ablation of cancer cells using a combination treatment of hyperthermia and HSP inhibition. (A) Absorbance spectrum 17-AAG shows a peak at approximately 330 nm, which is reflected in the 17-AAG-$C_{12}$ELP-GNR matrices. (B) The inset in (B) shows a digital snapshot of the 17-AAG-$C_{12}$ELP-GNR matrix loaded with 0.55 mg of the HSP90 inhibitor drug. Drug loading can also be seen from the change in color of the matrix.

Suboptimal administration of hyperthermia can result in the incomplete ablation of tumors and selection of clones that are resistant to treatment. While temperatures above 46° C. result in significant loss of cell viability, mild or moderate hyperthermic temperatures (40-46° C.) can have differential cytotoxic effects on cells, leading to variable efficacies. Constitutive and induced expression of HSPs, including HSP90, results in the refolding of proteins denatured by hyperthermia and, therefore, results in overcoming the apoptotic effects of the treatment. In particular, HSP90 is a stress-related protein, which interacts with several client proteins and regulates key processes inside cells, including protein degradation, and aids cancer cell survival following hyperthermia. Strategies that combine hyperthermic ablation with chemotherapeutic drugs that can overcome HSP-induced resistance can result in enhanced efficacy of hyperthermia as an adjuvant treatment. As a representative example of this approach, the chemotherapeutic HSP90 inhibitor was incorporated in 17-AAG in the matrix, for generating a multifunctional matrix capable of simultaneously administering both hyperthermia and chemotherapy, in order to enhance the ablation of cancer cells. The HSP90 inhibitor was incorporated within $C_{12}$ELP-GNR matrices during their formation leading to 17-AAG-C12ELP-GNR matrices (FIG. 15). The absorbance spectrum of 17-AAG-$C_{12}$ELP-GNR matrices demonstrated an additional peak at 335 nm (FIG. 15), which was indicative of the incorporation of 17-AAG within the polypeptide matrix; approximately 550 µg of the drug were incorporated within a single matrix.

Figure 14:
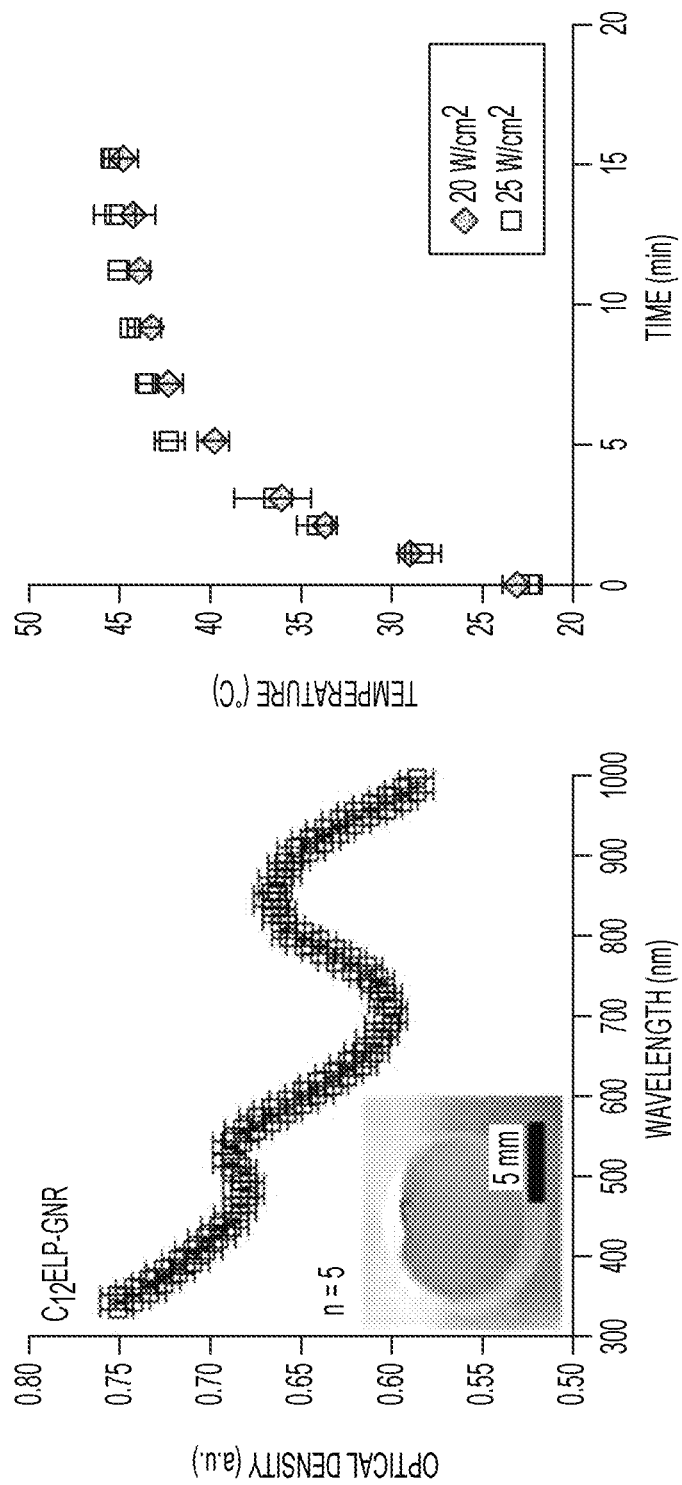
FIG. 14 shows optical and photothermal response of C12 elastin-like polypeptide-gold nanorod matrices. C12ELP-GNR matrices were formed on a glass cover slip (inset) and the absorbance (optical density) spectrum of the film was analyzed using a plate reader. Uniform distribution of GNRs in the matrix resulted in optical properties similar to that of GNR dispersions; characteristic peaks at 520 nm and in the near infrared (~850 nm) region in the spectrum can be seen. Retention of optical properties of GNRs in the matrix resulted in a reliable photothermal response as seen from the temperature kinetics of 500 ul phosphate-buffered saline on top of the matrix in a 24-well plate. The matrix was irradiated using an 850 nm laser at two different power densities and the temperature of phosphate-buffered saline was measured using a K-type thermocouple.
Figure 16:
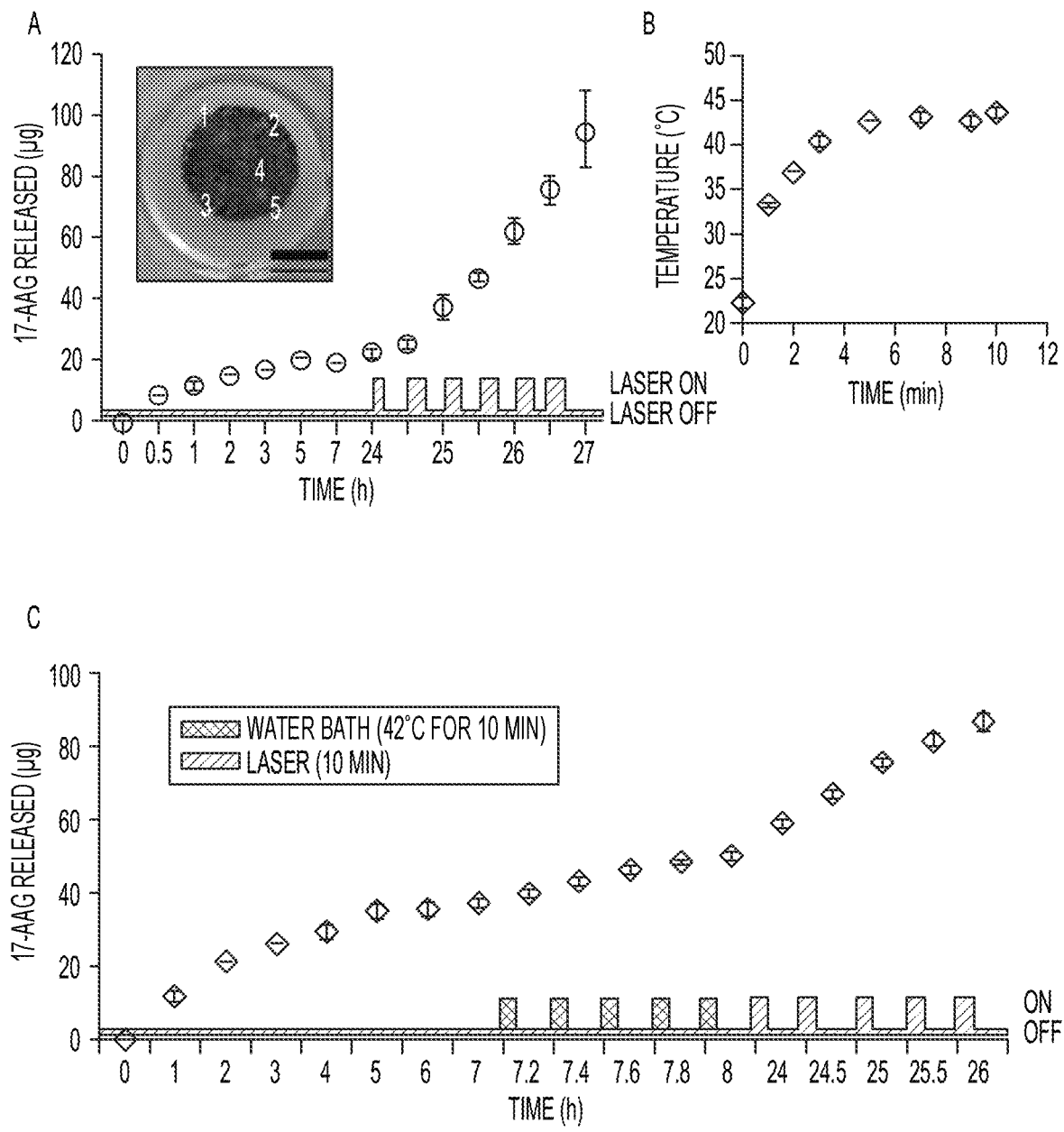
FIG. 16 shows photothermally activated release of the heat-shock protein 90 inhibitor drug, 17-AAG from 17-AAG-$C_{12}$ elastin-like polypeptide-gold nanorod matrices. (A) Diffusional release (leaching) of 17-AAG from the 17-AAG-$C_{12}$ELP-GNR matrix was monitored for 24 h to a supernatant of phosphate-buffered saline (volume 500 μl). Approximately 10 μg of the drug was released in the first hour, following which minimal drug release was observed for the rest of the duration as seen in the cumulative data plotted above. The matrix was then subjected to laser irradiation for releasing the drug. During laser pulse-triggered release, the first laser irradiation lasted for 5 min (850 nm, 25 W/cm$^2$), the second to sixth laser irradiations (850 nm, 25 W/cm$^2$) were for 10 min, with 20-min interval without laser in between each irradiation. Data shown are mean±standard deviation from four independent experiments (n=4). (B) The temperature profile during 10-min laser exposure was monitored with a K-type thermocouple. The temperature reached 43-44° C. (heat-shock conditions) following 5 min of laser irradiation, and remained invariant thereafter. Laser irradiation resulted in an additional 45-50 mg of 17-AAG released from the 17-AAG-$C_{12}$ELP-GNR matrices, indicating the potential for combined hyperthermia and heat-shock inhibition. (C) Role of laser irradiation on enhancing 17-AAG release from $C_{12}$ELP-GNR matrices. Matrices were first investigated for diffusional leaching of the drug, followed by incubation in a water bath at 42° C., and were finally irradiated with an near-infrared laser. Increased amounts of drug were released following laser treatment, presumably due to higher localized temperatures in the path of the laser. 17-AAG: 17-(allylamino)-17-demethoxygeldanamycin.

FIG. 16 shows a representative release profile of the 17-AAG from the matrix. The matrix was first placed in PBS to investigate diffusional leaching of the drug. Approximately 10 µg of the drug was released in the first hour, following which an additional 7 µg of the drug were released over the next 23 h, indicating that only a total of 3% of the encapsulated drug leached out due to diffusion. This demonstrates that the matrices are able to stably incorporate chemotherapeutic drugs with minimal loss owing to leaching. This is significant, since unintended drug loss from the matrix can result in undesired side effects. Subjecting the matrix to laser irradiation resulted in an increase in local temperature due to the photothermal effects of GNRs, which, in turn, led to enhanced release of 17-AAG from the matrix, presumably due to ELP structural changes and aggregation above the transition temperature, which in turn, can result in contraction of the matrix leading to drug efflux. The concomitant temperature increase is shown in FIG. 16 and is similar to that observed with the matrix in the absence of the drug (FIG. 14). A 5-min laser irradiation pulse (850 nm laser, 25 W/cm$^2$) resulted in the release of only 2.5 µg 17-AAG, indicating longer exposure times were necessary for increased release of the drug. Subsequent laser exposures were, therefore, carried out for 10 min each (850 nm, 25 W/cm2), which resulted in the release of 12.6 µg±2.4 µg for each round of laser irradiation. Discolored spots on the C12ELP-GNR matrix (FIG. 16) indicate regions of drug release following exposure to the laser. This is consistent with the temperature profiles in FIG. 16, which indicated that merely reaching hyperthermic temperatures may not be enough to trigger drug release and that sustained hyperthermic temperatures are required.

In order to further investigate the role of laser-induced drug release, the matrix for diffusional drug release was first investigated, followed by incubation at moderately hyperthermic temperatures (42° C.), and finally laser treatments. The total amount of drug originally encapsulated in this matrix was approximately 614 which was higher than the amount encapsulated in the matrix shown in FIG. 16. As seen in FIG. 16, higher 17-AAG quantities were released following laser irradiation compared with the water bath incubation treatment. It is possible that temperatures directly in the path of the laser are significantly higher than 42-44° C., and lead to greater drug release due to more significant changes in the matrix at these locations.

Taken together, these results indicate that the photothermal properties of the polypeptide matrix facilitate local increases in temperature following laser irradiation, which in turn triggers release of the encapsulated drug, presumably due to a combination of increased drug diffusivity and ELP aggregation and contraction at temperatures above the polypeptide transition temperature.

The efficacy of the simultaneous was then tested through administration of hyperthermia and HSP90 inhibitor for the ablation of prostate cancer cells. In order to account for the efficacy of this combination treatment, two 'single-agent' treatments were first carried out: hyperthermia alone, in which the matrix without the 17-AAG drug was employed for killing cancer cells only due to hyperthermic temperatures in the absence of the drug, and 17-AAG alone, in which loss of cancer cell viability due to constitutive 17-AAG diffusional release from the matrix was evaluated in the absence of laser-induced hyperthermia.

Figure 17:
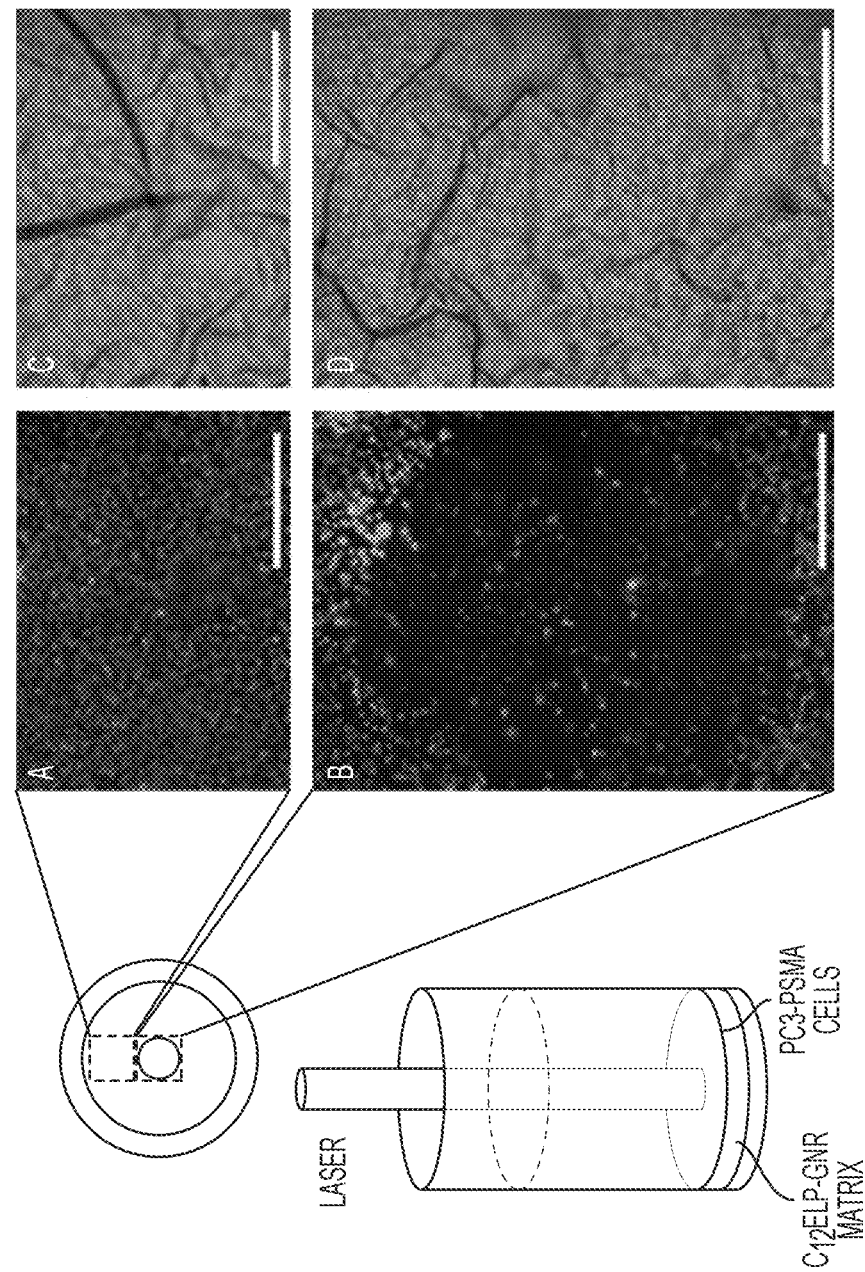
FIG. 17 shows C12 elastin-like polypeptide-gold nanorod matrices cell ablation set up with fluorescence (A & B) and phase (C & D) images. PC3-PSMA human prostate cancer cells were cultured on C12ELP-GNR matrices (without 17-AAG drug) for 24 h, and irradiated with an 850-nm laser (25 W/cm2) for 7 min. Viability of cells directly under the 1-mm laser irradiation spot (top; circled area) and outside the laser spot (bottom) was determined using the Live/Dead® assay in which living cells stained green while dead cells stained red. Cells directly under the laser were killed by the hyperthermic treatment while those outside the laser irradiation spot were alive. Approximate locations of the images on the matrix are shown. Representative images are from two independent experiments (n=2). Scale bar: 500 µm.

$C_{12}$ELP-GNR matrices (without 17-AAG) supported the growth of PC3-PSMA human prostate cancer cells, indicating that the plasmonic matrix was not toxic to cells. For the 'hyperthermia alone' treatment, cells were irradiated with an 850 nm laser (25 W/cm$^2$ laser for 7 min) and cell viability was determined using the Live/Dead assay 24 h after the laser treatment. Phase contrast and fluorescence microscopy images were recorded immediately after staining. As expected, laser irradiation resulted in significant death of PC3-PSMA cells directly in the path of the laser beam as seen from the red-stained cells in FIG. 17, consistent with previous observations in the literature[32,33]. However, cells outside the path of the laser beam did not undergo any loss of viability as seen from the green-stained living cells in FIG. 17. These results highlight spatial limitations associated with nanoparticle-mediated hyperthermic ablation of cancer cells; while nanoparticles and laser irradiation can be employed for localized treatments, effective treatment can be administered only over a limited region, leading to ineffective treatment. Importantly, the plasmonic matrix is biocompatible and can be used for the hyperthermic ablation of cancer cells, and in treatments where the spatial limitations of hyperthermia are not a concern.

Figure 18:
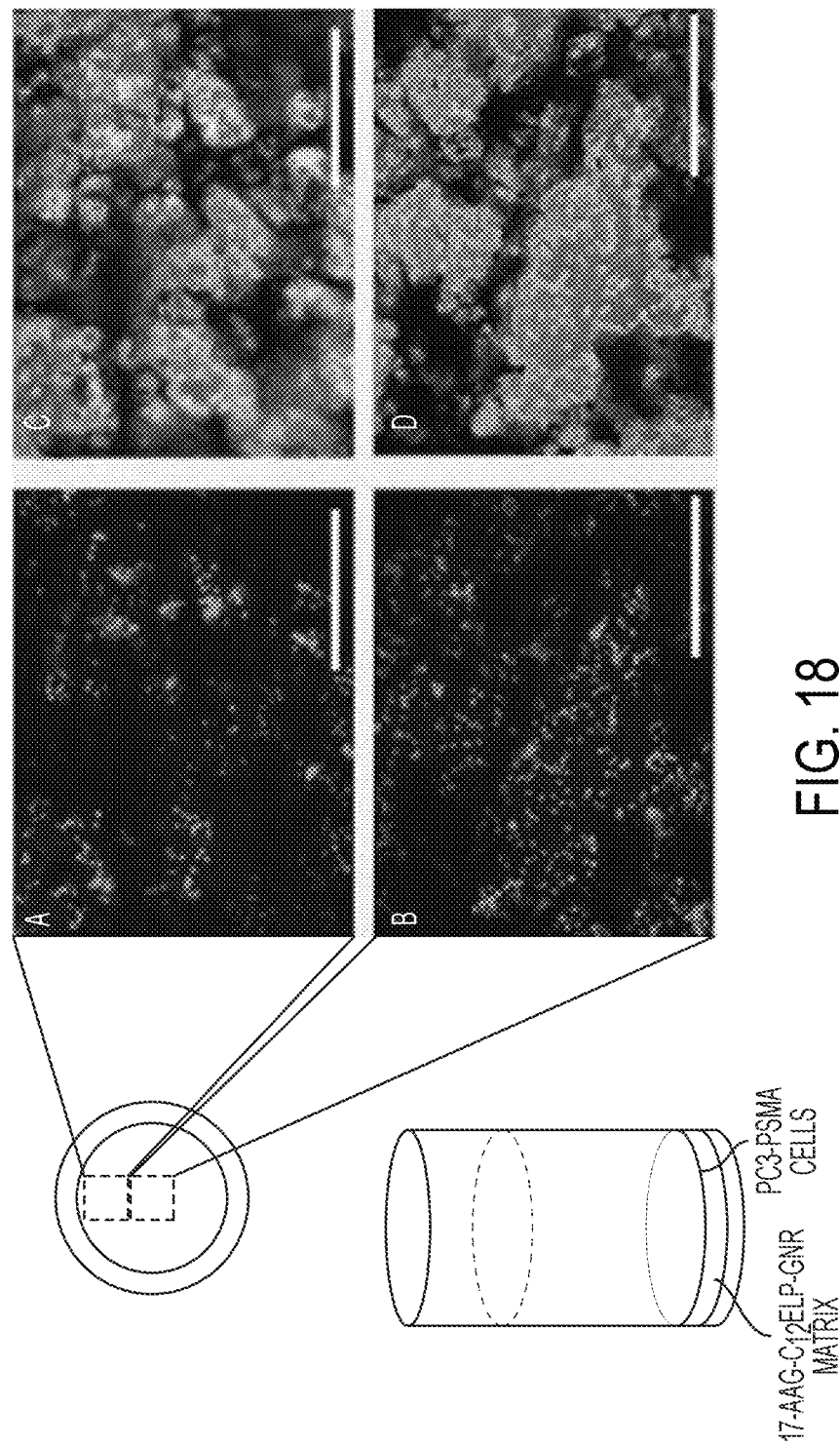
FIG. 18 shows 17-AAG-C12 elastin-like polypeptide-gold nanorod matrices cell culture set up with fluorescence (A & B) and phase (C & D) images. PC3-PSMA human prostate cancer cells were cultured on 17-AAG-$C_{12}$ELP-GNR matrices for 48 h (no laser treatment) and viability of cells was determined using the Live/Dead® assay. Diffusional release of 17-AAG from the matrix did not alter the viability of the cells. Approximate locations of the images on the matrix are shown. Representative images from three independent experiments (n=3). Scale bar: 500 µm.
Figure 19:
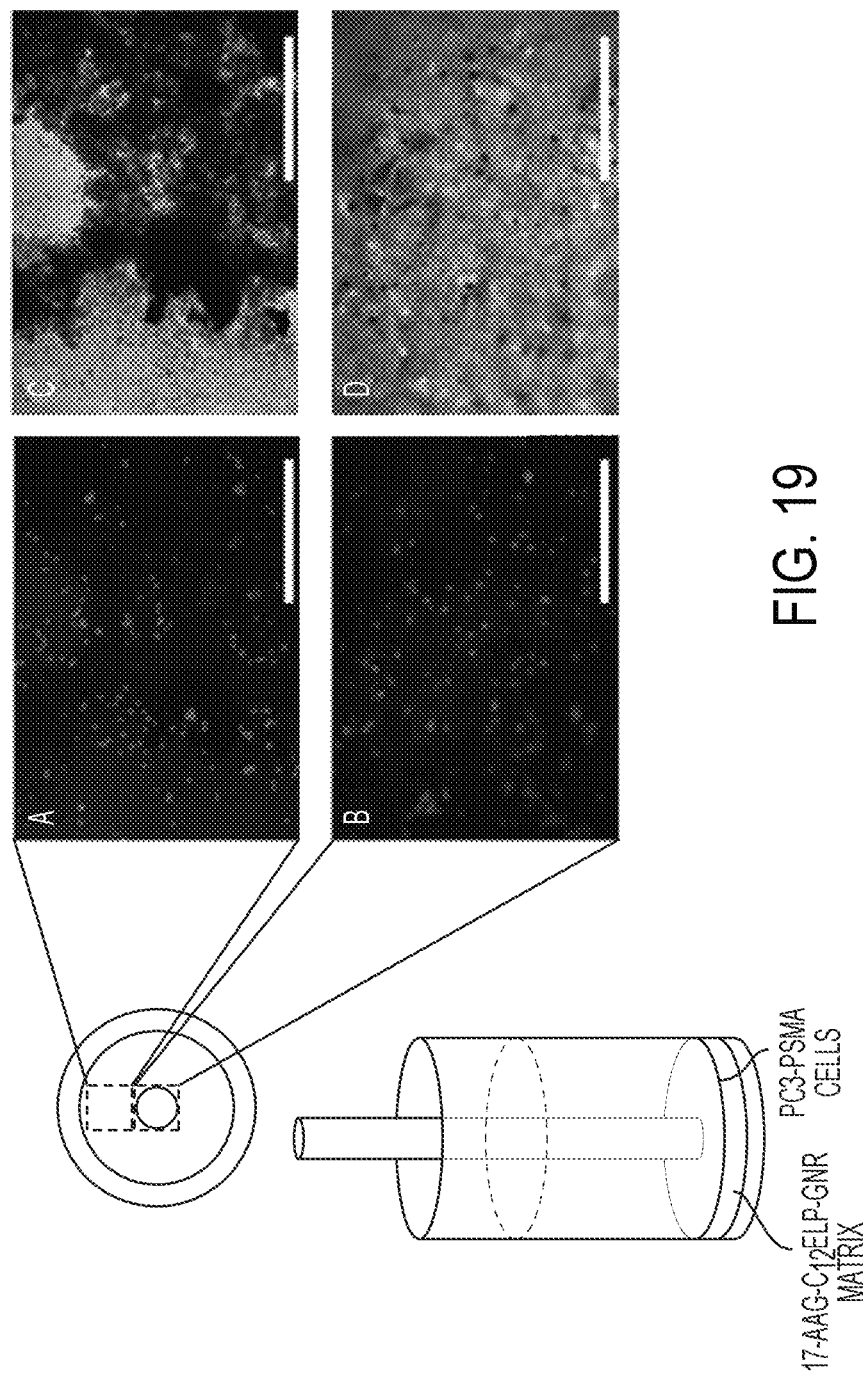
FIG. 19 shows 17-AAG-$C_{12}$ elastin-like polypeptide-gold nanorod matrices cell ablation set up with fluorescence (A & B) and phase (C & D) images. PC3-PSMA human prostate cancer cells were cultured on $C_{12}$ELP-GNR-17-AAG matrices for 24 h and irradiated with an 850-nm laser (25 W/cm$^2$) for 7 min. Cell viability was investigated after 24 h of the laser treatment using the Live/Dead® assay (total cell culture time=48 h). Representative images at two different locations away from the laser irradiation spot demonstrate approximately 90% cell death due to the combination of mild hyperthermia (43° C.
Figure 20:
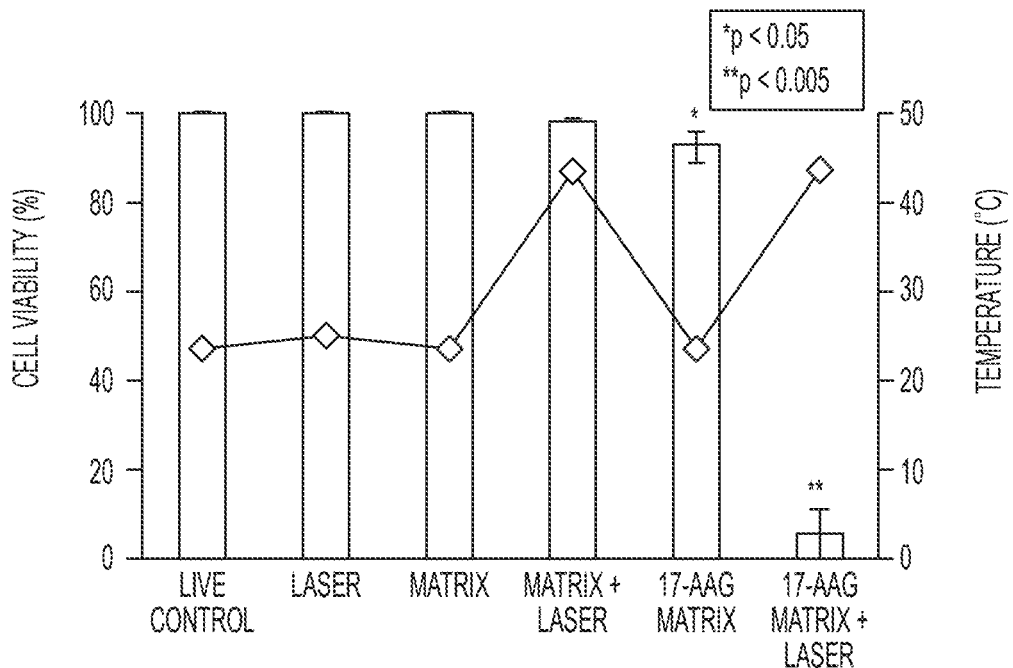
FIG. 20 shows the quantitative analysis of cell death demonstrates the efficacy of the laser-induced combination treatment of hyperthermia and heat-shock inhibitor 17-AAG using 17-AAG-C12 elastin-like polypeptide-gold nanorod matrices. Matrix indicates the $C_{12}$ELP-GNR matrix and 17-AAG matrix indicates 17-AAG-$C_{12}$ELP-GNR (i.e., drug-loaded) matrices (n=3 for all conditions).

$C_{12}$ELP-GNR plasmonic matrices, containing the anti-HSP90 drug 17-AAG (17-AAG-$C_{12}$ELP-GNR), were evaluated in the absence of laser-induced hyperthermia (drug-alone treatment). The matrices were able to support cell culture for 48 h, indicating that the constitutive diffusional release of 17-AAG from the matrix was not sufficient to induce cell death in cancer cells (FIG. 18). In order to investigate the efficacy of the combination treatment for killing cancer cells, PC3-PSMA cells were exposed to an 850-nm laser (25 W/cm$^2$ laser for 7 min) and as before, cell viability was evaluated 24 h following the laser treatment. While a single circular shape corresponding to the size of the laser beam could not be located in this case, dead cells could be seen throughout the matrix (FIG. 19), indicating that a combination of the hyperthermic temperatures and the triggered release of the anti-HSP90 drug 17-AAG was responsible for extensive cancer cell death. The synergistic action between these combination treatments is demonstrated by quantitative analysis of the cell death results (FIG. 20). Drug-alone and laser-alone treatments resulted in minimal loss of cell viability (<10% of the cell population). However, the combination treatment (laser-induced hyperthermia and release of the HSP90 inhibitor) resulted in over 90% loss in cell viability (FIG. 20). The results indicate that drugloaded nanoparticle-polypeptide matrices can simultaneously overcome cancer cell resistance to nanoparticle-induced hyperthermia, which is mediated by HSP overexpression, and spatial limitations of laser-induced hyperthermia using plasmonic nanoparticles (Table 1).

Table 1

TABLE 1

Summary of combination treatments.

| $C_n$ELP-GNR matrices | Laser power density (7-min irradiation) | Cell death Laser spot | Periphery |
|---|---|---|---|
| $C_{12}$ELP-GNR | 0 W/cm$^2$ | No | No |
| $C_{12}$ELP-GNR | 25 W/cm$^2$ | Yes | No |

TABLE 1-continued

Summary of combination treatments.

| $C_n$ELP-GNR matrices | Laser power density (7-min irradiation) | Cell death Laser spot | Periphery |
|---|---|---|---|
| 17-AAG-$C_{12}$ELP-GNR | 0 W/cm$^2$ | No | No |
| 17-AAG-$C_{12}$ELP-GNR | 25 W/cm$^2$ | Yes | Yes |

17-AAG: 17-(allylamino)-17-demethoxygeldanamycin; ELP: Elastin-like polypeptide; GNR Gold nanorod.

Example 3 demonstrates that engineered polypeptides can be interfaced with GNRs, resulting in the formation of stable, degradable and biocompatible plasmonic matrices.

E. Example 4

Nanocomposite preparation procedure: Gold nanorods (0.24 mM), in presence of CTAB concentrations less than 0.25 mM, were incubated with C12ELP overnight at 4° C., leading to formation of the nanoassemblies (dispersion) mediated by gold-thiol bonds. Briefly, prior to self-assembly, C12ELP was treated with Reductacryl® resin for 15 min at a 1:5 weight ratio, in order to reduce the cysteines in the polypeptide chain. Reduced C12ELP (2 mg/ml in 1× phosphate buffered-saline or PBS) was separated from the Reductacryl® resin by centrifugation at 8,000 rcf for 10 min and mixed with GNR dispersions at a volumetric ratio of 1:1. Solid-phase nanocomposites were prepared by incubating 1.5 ml C12ELP-GNR nanoassemblies (dispersion) in a 1 cm diameter home-made acrylic column device at 37° C. (or 60° C.) for 4 h. This led to temperature-triggered, entropy-dominated phase transition of C12ELP, which, in concert with GNR-thiol and intra- and inter-molecular cysteine-cysteine cross-linking, resulted in the formation of maroon-colored plasmonic nanocomposite film on a circular cover slip originally placed at the bottom of the device.

F. Example 5

Tissue preparation: Tissue samples were defrosted overnight at 4° C. following which they were kept moist with 1×PBS at 25° C. for laser tissue welding. A 5 mm full thickness incision was applied at the center of the intestine section (4×1 cm, ~0.1 cm thick). The incision edges were brought into contact with one another, nanocomposite (1 cm diameter) was applied on top of the serosa layer and across the incision with full contact. Laser irradiation (20 W/cm$^2$) was applied vertically at a speed of 1 mm/second across the nanocomposite for 1, 3, 5, and 7 minutes and samples were kept moist during welding to minimize charring.

Cell Culture on Nanocomposite Solders: NIH 3T3 murine fibroblast cells were cultured at 5% CO2 and 37° C. using DMEM medium containing 10% heat-inactivated fetal bovine serum and 1% antibiotics. The biocompatibility of nanocomposites containing various GNR (1.9-5.4 wt %) and PEG (0-19.7 wt %) weight percentages was evaluated in 96-well plates. Nanocomposites were formed at the bottom of the wells and treated with serum-containing cell culture medium. Fibroblasts (5,000 cells/well) were seeded on top of nanocomposites for 24, 48 and 72 hours. Cell viability analyses were carried out using the fluorescence-based LIVE/DEAD® assay (Invitrogen) and Zeiss AxioObserver D1 inverted microscope (Carl Zeiss MicroImaging Inc.). Quantitative analysis was carried out by counting cells using the ImageJ software.

Laser Tissue Welding: A titanium sapphire laser pumped by a solid-state laser (Spectra-Physics, Millennia) was employed for laser tissue welding. The excitation source (continuous wave, 2 mm beam diameter) was tuned to overlap with the $\lambda_{max}$ of the nanocomposites at 800 nm. Tissue samples were defrosted in Nanopure water and kept moist at 25° C. for laser tissue welding.

Tensile Strength Measurements: An 8 mm full thickness incision was applied at the center of the intestine section (4×1 cm, ~0.1 cm thick). The incision edges were brought into contact with one another, nanocomposite (1 cm diameter) was applied on top of the serosa layer and across the incision with full contact. Laser light (20 W/cm$^2$) was applied vertically at a speed of 1 mm/second across the nanocomposite for 60 seconds, and samples were kept moist during welding to minimize charring. After welding, tissue tensile strength was measured using TA XT plus Texture Analyser (Texture Technology Corp., NY) with a 5 kg load cell. Welded tissues were held with pneumatic grips to prevent slipping during testing. Testing was carried out in the tension mode at a rate of 0.5 mm/second until failure. The maximum force (N) achieved before the tissue breakage was recorded and reported in ultimate tensile strength (UTS, kPa). Intact porcine small intestine sections were subjected to mechanical testing to determine the UTS of uncut specimens. Data reported represent the mean±one standard deviation from at least three and up to twelve individual samples.

Bursting and leaking pressure tests were conducted on tubular porcine intestines. A home-made pressure detection system was designed and built. The tubular porcine intestines were cut into approximately 10 cm sections, leaving both ends opened. A full thickness incision (~5 mm) was applied to the center of the tubular intestine. The nanocomposite was applied to the incision. The CW laser (20 W/cm$^2$) was then applied to the nanocomposite (GNR 5.4 wt %) and tissue for various durations (1, 3, 5, and 7 min). After LTW was complete, the intestines were tightly clamped at both ends. A 21G Precision Glide needle was inserted into the tissue and dyed water was fed into the intestine sections. The pressure was monitored and recorded at the leaking and bursting points. The leaking pressure was defined as when the first drop of colored water was seen coming out of the weld site[1]. The bursting pressure was defined as when a stream of water was seen coming out of the weld site. Control bursting and leaking pressure tests were conducted on intact and cut tissues. The bursting pressure site was always along the length of the intestine. Dye leakage from the needle puncture site was considered negligible.

Bacteria Leakage Study: The leakage of Escherichia coli DH5-α bacterial cells from intestines was evaluated. A 5 mm incision was applied to the center of each 10 cm tubular intestine and subjected to different treatments. Immediately after treatment, the tubular intestines were hung vertically in Erlenmeyer flasks (each filled with 190 mL of fresh LB broth) leaving two open ends pointing up. The U-shape hanging method ensures the incision (or welded) sites were submerged into to the fresh LB broth. A 10 mL culture of bacterial cells at an optical density (OD$_{600}$) of 0.5 were placed inside the intestine and allowed incubation (37° C., 100 rpm). The optical densities of the fresh LB broth were monitored as a function of time as an indication for leakage.

Thermal Imaging: Following tissue preparation, tissue were images with an IR camera (FLIR s60) immediately before laser welding. A 5 cm piece of plastic kept on ice was placed next to the tissue for reference. During laser welding, IR images of the sample were taken at 30 second intervals and immediately after welding were completed. Following welding, the ELP-GNR matrix solder was removed from the tissue, and bare tissue was also imaged.

Histology. Immediately following welding, ELP-GNR matrix solders were either removed from tissue or left in place. Tissue samples were washed once in 1×PBS and fixed by immersion in Zamboni's fixative. Zamboni fixative is neutral buffered formalin made 0.18% with picric acid. The specimens were dehydrated through an increasing ethanol gradient, cleared with toluene, and embedded in Paraplast+ at 60° C. Ten micrometer thick sections were cut on an AO rotary microtome, collected on glass slides, and stored overnight at 40° C. The wax sections were deparaffinized with toluene and brought from ethanol to Nanopure™ water gradually. The sections were stained with hematoxylin and eosin (H&E) according to the manufacturer's instructions, dehydrated once more, and mounted in Permount. Micrographs were collected with an inverted Nikon microscope equipped with an Olympus DP25 color camera.

Collagen-$C_{12}$ELP-GNR Nanocomposites. 5.4% GNR-wt % Collagen-$C_{12}$ELP-GNR Nanocomposites were synthesized similarly as explained above. Nanocomposites were synthesized at ratios of 75%-25% ELP-Collagen. For example, at a 75%-25% $C_{12}$ELP-collagen, $C_{12}$ELP (1.5 mg) was co-incubated with GNRs (115 μg) at 4° C. overnight. Following formation of $C_{12}$ELP-GNRs, the nanoassemblies were centrifuged at 6000 rcf and re-dispersed in 100 of Rat Tail Type 1 Collagen Solution (5 mg/ml). Collagen—GNR-$C_{12}$ELP nanoassemblies mixtures were placed in a device and incubated at 37° C. overnight, leading to the formation of Collagen-$C_{12}$ELP-GNR nanocomposites on top of a glass coverslip.

(1) Results

Tensile strength. Cellularized as well as non-cellularized nanocomposites were investigated as solders for laser-based welding of porcine small intestines ex vivo. The injury model employed in this study is representative of bowel tissue after conventional anastamoses with leakage. Following an injury to the intestine, the plasmonic nanocomposite (1 mm diameter and ~2 mg) was applied to the incision, followed by laser treatment. The tensile strength of the rectangular tissue section was employed to evaluate the mechanical integrity of different treatments, see FIG. 6A. As expected, ruptured and intact small intestine sections possess the lowest (0.11±0.01 MPa) and highest (0.45±0.02 MPa) ultimate tensile strengths, respectively, see FIG. 6B. In the absence of the plasmonic nanocomposites, laser irradiation alone (20 W/cm$^2$, 1 mm/sec and 3 min) across the incision did not enhance the tensile strength of the ruptured intestine. In absence of laser irradiation, nanocomposites alone demonstrated negligible adhesion, and enhanced the tensile strength of the ruptured tissue by a modest ~0.03 MPa (p=0.052, n=11).

NIR laser irradiation (20 W/cm$^2$; constant speed of 1 mm/sec) of nanocomposites containing 1.9, 5.4 and 8.7 wt % GNRs resulted in bulk temperatures of 46±1.1, 61±1.5 and 64±0.9° C. respectively (n=9), due to the photothermal properties of these plasmonic biomaterials. It is likely that the temperature at the site of the weld may be much higher than the bulk temperature. Irradiating ruptured nanocomposites containing 1.9 wt % and 5.4 wt % GNR with NIR laser for only one minute resulted in an increase in the ultimate tensile strength up to 0.17±0.01 MPa and 0.22±0.01 MPa, respectively. The higher recovery in case of GNR concentration of 5.4 wt % may be due to the higher welding temperature 61±1.5° C. attained in this case. It is typically necessary to heat tissues above 60° C. in order to induce coagulation of proteins for obtaining robust welds[2, 3].

Increasing the laser irradiation time from 1 minute to 7 minutes, and increasing the GNR content in nanocomposites from 5.4 to 8.7 wt % did not enhance the tensile strength of the welded tissue further. Standard suturing techniques allow for up to 60% recovery of the mechanical strength of ruptured bowel intestinal tissue by 3 to 4 days[4, 5]. It was demonstrated that laser treatment in combination with nanocomposites can enhance the tensile strength of ruptured intestinal sections up to approximately 47% of the original intact form.

Figure 6C:
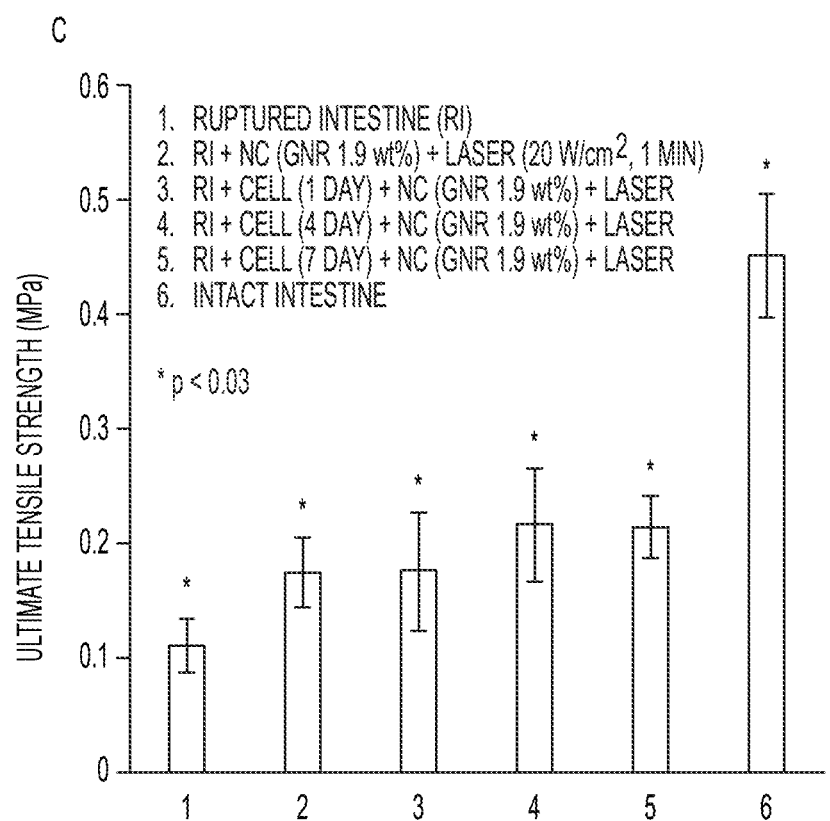

Fibroblast-cultured nanocomposites were also used for welding the ruptured intestine, see FIG. 6C; fibroblasts were cultured on top of the nanocomposites (GNR 1.9 wt %) for 1, 4, and 7 days before laser tissue welding. In all cases, welding strengths were similar to those observed with a cellular nanocomposites, indicating that materials cellularized with judicious choice of cells can further participate in repair and regeneration of welded tissues.

A critical aspect of sealing intestinal and colorectal tissues involves prevention of leakage of luminal fluid after anastomosis. Exposure of surrounding tissues to this bacteria-rich fluid can result in sustained inflammation, shock, and mortality[6-8]. To ensure that nanocomposite-assisted laser tissue welding results in fluid-tight sealing, the following were investigated: (i) the leakage and bursting pressure (defined in the experimental section) and (ii) bacterial leakage following welding.

Figure 21:
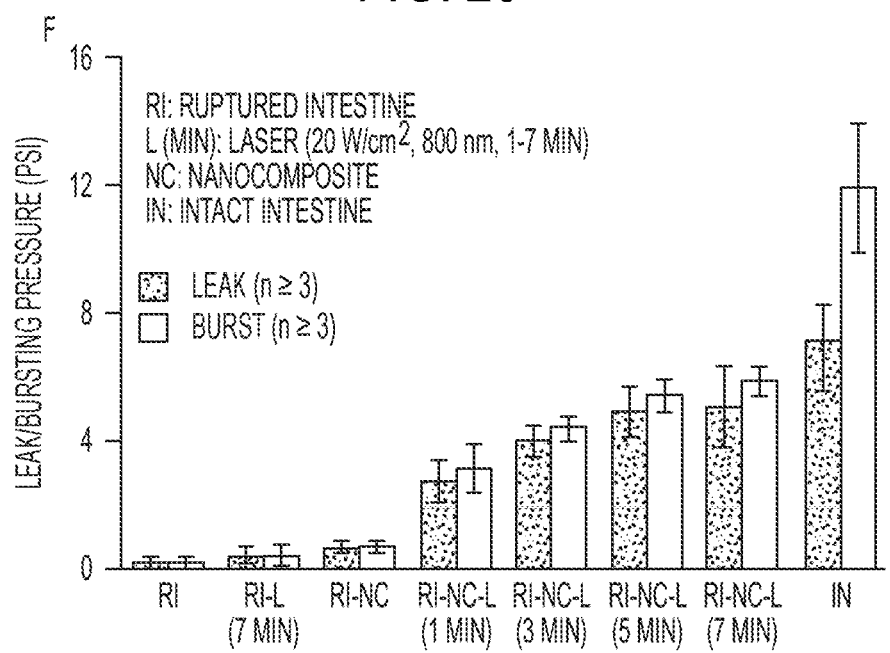
FIG. 21 shows the bursting and leakage pressures of tissues before and after laser tissue welding using nanocomposite solders.

Bursting and Leaking Pressure. Nanocomposites (~2 mg), at a fixed GNR concentration of 5.4 wt %, were first applied to the 5 mm cut, followed by laser irradiation leading to temperature increase up to 61±1.5° C. The leakage and bursting pressures were measured immediately after anastomosis using a device and reported in pounds per square inch (psi), see FIG. 21. As expected, the ruptured and intact intestine demonstrated the lowest and highest leakage/bursting pressures, respectively. In case of ruptured intestines, bursting was observed immediately and was followed by leakage. Both, the leakage and bursting pressures were approximately 0.2 psi. In case of intact intestines, the first evidence of leakage was observed at the needle piercing site at a pressure of 7.2 psi, while bursting was observed along the tissue when the pressure reached 12 psi. Ruptured intestines treated with laser alone (without nanocomposite) and nanocomposite alone (without laser treatment) demonstrated negligible leakage/bursting pressures (<1 psi), indicating that these treatments had minimal effect on repair. Laser irradiation of the nanocomposite at the incision site increased both the tissue leakage and bursting pressures. Increasing laser irradiation time from 1 to 7 minutes resulted in an increase in both, leakage and bursting pressures to up to 2.8 and 5.8 psi, respectively. In these cases, bursting immediately followed leakage, as reflected by similar values for leakage and bursting pressures.

Exposure of the tissue to the NIR laser for 5 and 7 minutes resulted in similar tissue leaking/bursting pressures; however, tissue charring and shrinkage were observed after irradiation for 7 minutes. Overall, laser irradiation of nanocomposites (GNR 5.4 wt %) for 5 minutes provided optimal tissue welding, and resulted in tissue leaking and bursting pressure recovery from 3% up to 71% and 45% of the their original intact forms, respectively.

Bacteria leakage. Leakage of bacteria from intestinal tissue was investigated following incision closure using nanocomposite-assisted laser welding. Based on previous optimization, nanocomposites (~2 mg) were employed at a fixed GNR concentration of 5.4 wt %, to weld a 5 mm incision located at the center of tubular porcine small intestine (~10 cm in length) using NIR laser irradiation (20 W/cm$^2$, 5 min). DH5-α E. coli cells were employed as model bacteria to mimic the inner condition of the intestine. Note that the bacterial concentration in intestine sections is 10$^5$-10$^9$ bacteria/gram of intestinal contents[9, 10]; E. coli cell cultures with an OD600 of 0.5 is approximately 4*10$^8$ bacteria/mL. Leakage of DH5-α cells from inside the intestine to the surrounding fresh LB culture broth was followed as an indication of resistance to infection.

Rupture of the small intestine resulted in leakage of DH5-α cells into fresh LB broth leading to increase in turbidity of the surrounding medium as measured using optical density at 600 nm or OD600. No leakage was observed in case of the intact intestine and the ruptured intestine treated with the nanocomposite and NIR laser irradiation two hours after introducing DH5-α cells (10 mL, OD$_{600}$=0.5) into the tubular small intestines. In these cases, the fresh LB broth remained clear or non-turbid. Conversely, the untreated ruptured intestine and ruptured intestine treated with laser alone (without nanocomposite) did not prevent leakage of bacteria; a significant increase in LB broth optical density was observed.

Figure 22A:
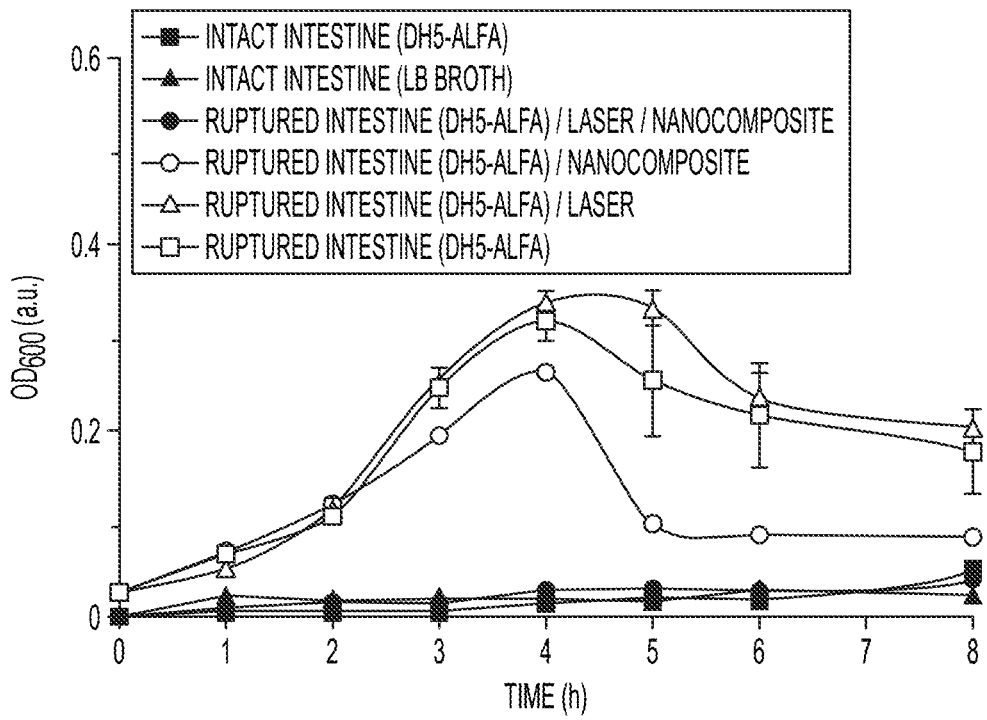
FIGS. 22A-22B show (A) and (B) the change in $OD_{600}$ of fresh LB broth monitored as a function of time (A: 0-8 h, B: 0-24 h) and at different treatment conditions for quantitative comparison.
Figure 22B:
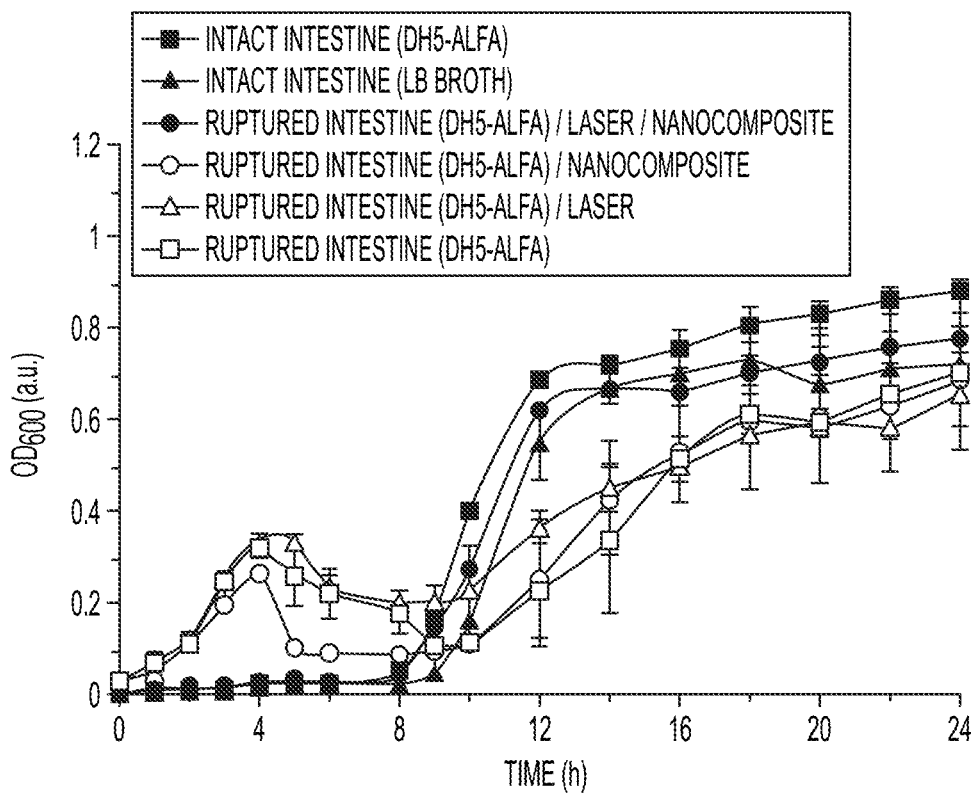

FIGS. 22A and 22B show a quantitative analysis of the bacterial leakage, based on OD$_{600}$. Bacterial leakage was immediately observed upon introduction of DH5-α cells into the tubular intestines in case of untreated ruptured intestine, ruptured intestine treated with the NIR laser alone (no nanocomposite), and ruptured intestine treated with nanocomposite alone (no laser) conditions (FIG. 22A, unfilled markers). In all these cases, OD$_{600}$ of the fresh LB broth increased from 0 at 0 h to 0.22±0.03 at 4 h, indicating growth of leaked bacterial in the fresh LB broth medium. These initial increases in optical density of fresh LB broth were followed by a gradual decrease in OD$_{600}$ from 0.22±0.03 to 0.09±0.03 between 4 and 8 hours, which is likely due to the stationary and autolytic phases of DH5-α cells[11, 12]. Finally, a steady increase in OD$_{600}$ from 0.09±0.03 up 0.66±0.16 was observed between 8 and 24 hours (FIG. 22B, unfilled markers). This reflects the growth of pre-existing bacteria in the intestinal tissues.

For the condition where ruptured intestine was welded with both nanocomposite and NIR laser (FIG. 22A, circle filled markers), the optical density (OD$_{600}$) of the fresh LB broth remained low at 0.04±0.007 up to 8 hours after introduction of DH5-αcells into the tubular intestine, indicating no DH5-α leakage. An increase in optical density (up to 0.72±0.25) at 600 nm was observed after 8 h (FIG. 22B, circle filled markers). Both controls, intact intestine filled with either DH5-α cells or fresh LB broth without bacteria (FIG. 22B, square and triangle filled markers), showed a growth in turbidity similar to the nanocomposite-assisted, laser-welded ruptured intestine samples (FIG. 22B, circle filled markers), confirming that bacterial growth between 8 and 24 hours is due to pre-existing bacteria in the tissue, and not from the leakage of DH5-α cells into fresh LB broth medium. In addition, the overall growth of bacteria in conditions associated with DH5-α leakage (FIG. 22B, unfilled markers) is less pronounced that those without DH5-α leakage (FIG. 22B, filled markers). This is presumably due to the depletion of nutrients and the growth competition between DH5-α and intestinal bacteria associated with the tissues. Overall, ruptured intestines that underwent laser tissue welding using nanocomposites can provide a fluid-tight sealing and prevent bacterial leakage. The leakage prevention was successful and it was observed that the laser-activated nanocomposite continued to provide a liquid-tight sealing for at least up to one week, which was the duration of these studies (not shown).

Pulsed vs. Continuous Laser. Incised tissue samples were irradiated for 1, 3, 5, and 7 min using a continuous wave laser adjusted to 800 nm following application of ELP-GNR matrices (5.4 GNR wt %). Additionally, a tissue sample without an ELP-GNR matrix was irradiated with continuous wave laser adjusted to 800 nm for 7 min. Following irradiation, the all ELP-GNR solder was removed and tissue samples were examined. In all cases where the ELP-GNR matrix was present, the wound appeared to have closed and there was visible charring around the wound site. Before removal of the ELP-GNR matrices, IR images showed that the temperature increased when the samples were irradiated, the greatest temperature immediately after irradiation was 107° F. after 5 min of ELP-GNR laser welding.

Similarly, incised tissue samples were irradiated for 1, 3, 5, and 7 min using a pulsed laser adjusted to 800 nm following application of ELP-GNR matrices (5.4 GNR wt %). Following irradiation, it was found that for 5 min irradiation, most of the ELP-GNR solder was able to be removed, however some remained welded to the tissue. Charring was visible around the solder-wound site. For the 7 min irradiated sample, it was not possible to remove any of the solder from the tissue and extent of charring was not visible. Before removal of ELP-GNR matrices, IR images showed that immediately after 5 min irradiation, the maximum temperature reached was temperature ~148° F. and immediately following 7 min irradiation the temperature was ~171° F.

Histology. H and E histology was performed on porcine intestine samples. Control samples were prepared where a tissue sample was incised similar to the previous described incision model with the absence of application of the nanocomposites, and laser irradiation, a tissue sample was placed directly over a flame for 30 seconds, and a tissue sample was "branded" with the heated portion of a metal spatula. Histology images of the control burn samples show that despite excessive heat exposure, there does not appear to be major depth of thermal damage. There is a thin layer of charred tissue at the edge of the tissue and there does appear to be a darkening of the tissue closer to the edges.

Two porcine intestine tissues were cut and placed end-to-end and a 5.4%-GNR-C$_{12}$ELP nanocomposites was placed over the incised portion. One sample was irradiated with continuous wave laser for 3 minutes and the other was irradiated with pulsed laser for 3 minutes. H&E staining was performed on the samples.

Both the continuous wave and the pulsed samples are characterized by three distinct region. The tissue region is observed at a pinkish color, the nanocomposite region is observed as a purple color, and an adhesion line region, there the patch and the tissue are joined is observed as a lighter purple in between the first to regions. Similar to the control burn samples, in the pulsed samples there seems to be a darkening of tissue nearest to the nanocomposites patch.

C$_{12}$ELP-GNR-Collagen Nanocomposites. In order to tune the nanocomposites mechanical properties, the inclusion of collagen into the nanocomposites system was investigated. A 75%-25% C$_{12}$ELP-Collagen nanocomposite (1.5 mg C$_{12}$ELP, 0.5 mg Collagen, and 115 µg GNRs) was synthesized.

REFERENCES

1. Huang, H C, Yang, Y, Nanda, A, Koria, P, Rege, K. Synergistic administration of photothermal therapy and 1. chemotherapy to cancer cells using polypeptide-based degradable plasmonic matrices. Nanomedicine (Lond) 2011; 6(3): 459-73.
2. Huang, H C, Koria, P, Parker, S M, Selby, L, Megeed, Z, Rege, K. Optically responsive gold nanorod-polypeptide assemblies. Langmuir 2008; 24(24): 14139-44.
3. Karanjia, N D, Corder, A P, Beam, P, Heald, R J. Leakage from Stapled Low Anastomosis after Total Mesorectal Excision for Carcinoma of the Rectum. British Journal of Surgery 1994; 81(8): 1224-1226.
4. Isbister, W H. Anastomotic leak in colorectal surgery: A single surgeon's experience. Anz Journal of Surgery 2001; 71(9): 516-520.
5. Park, U. Influence of anastomotic leakage on oncological outcome in patients with rectal cancer. J Gastrointest Surg 2010; 14(7): 1190-6.
6. Thomson, G A. An investigation of leakage tracts along stressed suture lines in phantom tissue. Medical Engineering & Physics 2007; 29(9): 1030-1034.
7. Zuger, B J, Ott, B, Mainil-Varlet, P, Schaffner, T, Clemence, J F, Weber, H P, Frenz, M. Laser solder welding of articular cartilage: Tensile strength and chondrocyte viability. Lasers in Surgery and Medicine 2001; 28(5): 427-434.
8. Wolf-de Jonge, I C D, Beek, J F, Balm, R. 25 years of laser assisted vascular anastomosis (LAVA): What have we learned? European Journal of Vascular and Endovascular Surgery 2004; 27(5): 466-476.
9. Spector, D, Rabi, Y, Vasserman, I, Hardy, A, Klausner, J, Rabau, M, Katzir, A. In Vitro Large Diameter Bowel Anastomosis Using a Temperature Controlled Laser Tissue Soldering System and Albumin Stent. Lasers in Surgery and Medicine 2009; 41(7): 504-508.
10. Asencioarana, F, Garciafons, V, Torresgil, V, Molinaandreu, E, Vidalmartinez, J, Perersarrio, R, Martinersoriano, F. Effects of a Low-Power He—Ne-Laser on the Healing of Experimental Colon Anastomoses—Our Experience. Optical Engineering 1992; 31(7): 1452-1457.
11. Matteini, P, Rossi, F, Menabuoni, L, Pini, R. Microscopic characterization of collagen modifications induced by low-temperature diode-laser welding of corneal tissue. Lasers in Surgery and Medicine 2007; 39(7): 597-604.
12. Wadia, Y, Xie, H, Kajitani, M. Liver repair and hemorrhage control by using laser soldering of liquid albumin in a porcine model. Lasers in Surgery and Medicine 2000; 27(4): 319-328.
13. Kirsch, A J, Miller, M I, Hensle, T W, Chang, D T, Shabsigh, R, Olsson, C A, Connor, J P. Laser-Tissue Soldering in Urinary-Tract Reconstruction—First Human-Experience. Urology 1995; 46(2): 261-266.
14. Schober, R, Ulrich, F, Sander, T, Durselen, H, Hessel, S. Laser-Induced Alteration of Collagen Substructure Allows Microsurgical Tissue Welding. Science 1986; 232(4756): 1421-1422.
15. Gobin, A M, O'Neal, D P, Watkins, D M, Halas, N J, Drezek, R A, West, J L. Near infrared laser-tissue welding using nanoshells as an exogenous absorber. Lasers in Surgery and Medicine 2005; 37(2): 123-129.
16. Matteini, P, Ratto, F, Rossi, F, Cicchi, R, Stringari, C, Kapsokalyvas, D, Pavone, F S, Pini, R. Photothermally-induced disordered patterns of corneal collagen revealed by SHG imaging. Optics Express 2009; 17(6): 4868-4878.
17. Bass, L S, Moazami, N, Pocsidio, J, Oz, MC, Logerfo, P, Treat, M R. Changes in Type-I Collagen Following Laser-Welding. Lasers in Surgery and Medicine 1992; 12(5): 500-505.
18. Murray, L W, Su, L, Kopchok, G E, White, R A. Crosslinking of Extracellular-Matrix Proteins—a Preliminary-Report on a Possible Mechanism of Argon-Laser Welding. Lasers in Surgery and Medicine 1989; 9(5): 490-496.
19. Guillou, P J, Quirke, P, Thorpe, H, Walker, J, Jayne, D G, Smith, A M H, Heath, R M, Brown, J M. Short-term endpoints of conventional versus laparoscopic-assisted surgery in patients with colorectal cancer (MRC CLASICC trial): multicentre, randomised controlled trial. Lancet 2005; 365(9472): 1718-1726.
20. Smith, R L, Bohl, J K, McElearney, S T, Friel, C M, Barclay, M M, Sawyer, R G, Foley, E F. Wound infection after elective colorectal resection. Annals of Surgery 2004; 239(5): 599-605.
21. Nelson, H, Sargent, D, Wieand, H S, Fleshman, J, Anvari, M, Stryker, S J, Beart, R W, Hellinger, M, Flanagan, R, Peters, W, Ota, D, Hellinger, M. A comparison of laparoscopically assisted and open colectomy for colon cancer. New England Journal of Medicine 2004; 350(20): 2050-2059.
22. MacRae, H M, McLeod, R S. Handsewn vs. stapled anastomoses in colon and rectal surgery—A meta-analysis. Diseases of the Colon & Rectum 1998; 41(2): 180-189.
23. Beuran, M, Chiotoroiu, A L, Chilie, A, Morteanu, S, Vartic, M, Avram, M, Rosu, O, Lica, I. Stapled vs. hand-sewn colorectal anastomosis in complicated colorectal cancer—a retrospective study. Chirurgia 2010; 105(5): 645-651.
24. Park, I J. Influence of Anastomotic Leakage on Oncological Outcome in Patients with Rectal Cancer. Journal of Gastrointestinal Surgery; 14(7): 1190-1196.
25. Anderson, R H. Endoscopic laser surgery handbook (Science and practice of surgery series, vol. 10). International journal of cardiology 1988; 20(1): 157.
26. Cilesiz, I, Springer, T, Thomsen, S, Welch, A J. Controlled temperature tissue fusion: Argon laser welding of canine intestine in vitro. Lasers in Surgery and Medicine 1996; 18(4): 325-334.
27. Chikamatsu, E, Sakurai, T, Nishikimi, N, Yano, T, Nimura, Y. Comparison of Laser Vascular Welding, Interrupted Sutures, and Continuous Sutures in Growing Vascular Anastomoses. Lasers in Surgery and Medicine 1995; 16(1): 34-40.
28. Gennaro, M, Ascer, E, Mohan, C, Wang, S. A Comparison of Co-2 Laser-Assisted Venous Anastomoses and Conventional Suture Techniques—Patency, Aneurysm Formation, and Histologic Differences. Journal of Vascular Surgery 1991; 14(5): 605-613.
29. Grubbs, P E, Wang, S, Marini, C, Basu, S, Rose, D M, Cunningham, J N. Enhancement of Co2-Laser Microvascular Anastomoses by Fibrin Glue. Journal of Surgical Research 1988; 45(1): 112-119.
30. Capon, A, Iarmarcovai, G, Gonnelli, D, Degardin, N, Magalon, G, Mordon, S. Scar Prevention Using Laser-Assisted Skin Healing (LASH) in Plastic Surgery. Aesthetic Plastic Surgery 2010; 34(4): 438-446.
31. Matteini, P, Ratto, F, Rossi, F, Rossi, G, Esposito, G, Puca, A, Albanese, A, Maira, G, Pini, R. In vivo carotid artery closure by laser activation of hyaluronan-embedded gold nanorods. Journal of Biomedical Optics 2010; 15(4): 0415081-0415086.
32. Matteini, P, Ratto, F, Rossi, F, Centi, S, Dei, L, Pini, R. Chitosan Films Doped with Gold Nanorods as Laser-Activatable Hybrid Bioadhesives. Advanced Materials 2010; 22(38): 4313-4316.

33. LaJoie, E N, Barofsky, A D, Gregory, K W, Prahl, S A. Patch welding with a pulsed diode laser and indocyanine green. Lasers in Medical Science 1997; 12(1): 49-54.
34. Poppas, D, Sutaria, P, Sosa, R E, Mininberg, D, Schlossberg, S. Chromophore Enhanced Laser-Welding of Canine Ureters in-Vitro Using a Human Protein Solder—a Preliminary Step for Laparoscopic Tissue Welding. Journal of Urology 1993; 150(3): 1052-1055.
35. Lauto, A, Foster, L J R, Ferris, L, Avolio, A, Zwaneveld, N, Poole-Warren, L A. Albumin-genipin solder for laser tissue repair. Lasers in Surgery and Medicine 2004; 35(2): 140-145.
36. Cilesiz, I, Thomsen, S, Welch, A J, Chan, E K. Controlled temperature tissue fusion: Ho:YAG laser welding of rat intestine in vivo .2. Lasers in Surgery and Medicine 1997; 21(3): 278-286.
37. Cilesiz, I, Thomsen, S, Welch, A J. Controlled temperature tissue fusion: Argon laser welding of rat intestine in vivo .1. Lasers in Surgery and Medicine 1997; 21(3): 269-277.
38. Poppas, D P, Massicotte, J M, Stewart, R B, Roberts, A B, Atala, A, Retik, A B, Freeman, M R. Human albumin solder supplemented with TGF-beta(1) accelerates healing following laser welded wound closure. Lasers in Surgery and Medicine 1996; 19(3): 360-368.
39. Poppas, D P, Stewart, R B, Massicotte, M, Wolga, A E, Kung, R T V, Retik, A B, Freeman, M R. Temperature-controlled laser photocoagulation of soft tissue: In vivo evaluation using a tissue welding model. Lasers in Surgery and Medicine 1996; 18(4): 335-344.
40. Cilesiz, I. Controlled temperature phototheramal issue welding. Journal of Biomedical Optics 1999; 4(3): 327-336.
41. Klioze, S D, Poppas, D P, Rooke, C T, Choma, T J, Schlossberg, S M. Development and Initial Application of a Real-Time Thermal Control-System for Laser-Tissue Welding. Journal of Urology 1994; 152(2): 744-748.
42. Pasternak, B, Rehn, M, Andersen, L, Agren, M, Heegaard, A-M, Tengvall, P, Aspenberg, P. Doxycycline-coated sutures improve mechanical strength of intestinal anastomoses. International Journal of Colorectal Disease 2008; 23(3): 271-276.
43. Agren, M, Andersen, T, Andersen, L, Schidt, C, Surve, V, Andreassen, T, Risteli, J, Franzen, L, Delaissé, J-M, Heegaard, A-M, Jorgensen, L. Nonselective matrix metalloproteinase but not tumor necrosis factor-a inhibition effectively preserves the early critical colon anastomotic integrity. International Journal of Colorectal Disease 2011; 26(3): 329-337.
44. Dallas, P, Sharma, V K, Zboril, R. Silver polymeric nanocomposites as advanced antimicrobial agents: Classification, synthetic paths, applications, and perspectives. Advances in Colloid and Interface Science; 166(1,Äi2): 119-135.
45. Huang, X H, Jain, P K, El-Sayed, I H, El-Sayed, M A. Plasmonic photothermal therapy (PPTT) using gold nanoparticles. Lasers in Medical Science 2008; 23(3): 217-228.
46. Hu, M, Chen, J Y, Li, Z Y, Au, L, Hartland, G V, Li, X D, Marquez, M, Xia, Y N. Gold nanostructures: engineering their plasmonic properties for biomedical applications. Chemical Society Reviews 2006; 35(11): 1084-1094.
47. Weissleder, R. A clearer vision for in vivo imaging. Nature Biotechnology 2001; 19(4): 316-317.
48. Shao, X, Zheng, W, Huang, Z. Near-infrared autofluorescence spectroscopy for in vivo identification of hyperplastic and adenomatous polyps in the colon. Biosensors and Bioelectronics 2011; 30(1): 118-122.
49. Alencar, H, Funovics, M A, Figueiredo, J, Sawaya, H, Weissleder, R, Mahmood, U. Colonic Adenocarcinomas: Near-Infrared Microcatheter Imaging of Smart Probes for Early Detection, AIStudy in Micel. Radiology 2007; 244(1): 232-238.
50. Mackay, J A, Chilkoti, A. Temperature sensitive peptides: Engineering hyperthermia-directed therapeutics. International Journal of Hyperthermia 2008; 24(6): 483-495.
51. Nettles, D L, Chilkoti, A, Setton, L A. Applications of elastin-like polypeptides in tissue engineering. Advanced Drug Delivery Reviews 2010; 62(15): 1479-1485.
52. Kim, W, Chaikof, E L. Recombinant elastin-mimetic biomaterials: Emerging applications in medicine. Advanced Drug Delivery Reviews 2010; 62(15): 1468-1478.
53. McDaniel, J R, Callahan, D J, Chilkoti, A. Drug delivery to solid tumors by elastin-like polypeptides. Advanced Drug Delivery Reviews 2010; 62(15): 1456-1467.
54. Koria, P, Yagi, H, Kitagawa, Y, Megeed, Z, Nahmias, Y, Sheridan, R, Yarmush, M L. Self-assembling elastin-like peptides growth factor chimeric nanoparticles for the treatment of chronic wounds. Proc Natl Acad Sci USA 2011; 108(3): 1034-9.
55. McHale, M K, Setton, L A, Chilkoti, A. Synthesis and in vitro evaluation of enzymatically cross-linked elastin-like polypeptide gels for cartilaginous tissue repair. Tissue Engineering 2005; 11(11-12): 1768-1779.
56. Pasternak, B, Matthiessen, P, Jansson, K, Andersson, M, Aspenberg, P. Elevated intraperitoneal matrix metalloproteinases-8 and -9 in patients who develop anastomotic leakage after rectal cancer surgery: a pilot study. Colorectal Disease 2010; 12(7Online): e93-e98.
57. Kim, J C, Lee, Y K, Lim, B S, Rhee, S H, Yang, H C. Comparison of tensile and knot security properties of surgical sutures. Journal of Materials Science-Materials in Medicine 2007; 18(12): 2363-2369.
58. Watters, D A K, Smith, A N, Eastwood, M A, Anderson, K C, Elton, R A, Mugerwa, J W. Mechanical-Properties of the Colon—Comparison of the Features of the African and European Colon Invitro. Gut 1985; 26(4): 384-392.
59. Teng, W, Cappello, J, Wu, X. Recombinant Silk-Elastin-like Protein Polymer Displays Elasticity Comparable to Elastin. Biomacromolecules 2009; 10(11): 3028-3036.
60. Rnjak-Kovacina, J, Wise, S G, Li, Z, Maitz, P K M, Young, C J, Wang, Y, Weiss, A S. Tailoring the porosity and pore size of electrospun synthetic human elastin scaffolds for dermal tissue engineering. Biomaterials 2011; 32(28): 6729-6736.
61. McKenna, K A, Hinds, M T, Sarao, R C, Wu, P-C, Maslen, C L, Glanville, R W, Babcock, D, Gregory, K W. Mechanical property characterization of electrospun recombinant human tropoelastin for vascular graft biomaterials. Acta Biomaterialia 2012; 8(1): 225-233.
62. Thomsen, S, Morris, J R, Neblett, C R, Mueller, J. Tissue Welding Using a Low-Energy Microsurgical Co2-Laser. Medical Instrumentation 1987; 21(4): 231-237.
63. Chen, C C, Lin, Y P, Wang, C W, Tzeng, H C, Wu, C H, Chen, Y C, Chen, C P, Chen, L C, Wu, Y C. DNA-gold nanorod conjugates for remote control of localized gene expression by near infrared irradiation. Journal of the American Chemical Society 2006; 128(11): 3709-3715.
64. Ratto, F, Matteini, P, Cini, A, Centi, S, Rossi, F, Fusi, F, Pini, R. CW laser-induced photothermal conversion and shape transformation of gold nanodogbones in hydrated chitosan films. Journal of Nanoparticle Research 2011; 13(9): 4337-4348.
65. Garcia, P, Mines, M J, Bower, K S, Hill, J, Menon, J, Tremblay, E, Smith, B. Robotic Laser Tissue Welding of Sclera Using Chitosan Films. Lasers in Surgery and Medicine 2009; 41(1): 60-67.
66. Huang, H C, Rege, K, Heys, J J. Spatiotemporal temperature distribution and cancer cell death in response to extracellular hyperthermia induced by gold nanorods. ACS Nano 2010; 4(5): 2892-900.
67. Galya, T, Sedlarik, V, Kuritka, I, Novotny, R, Sedlarikova, J, Saha, P. Antibacterial Poly(vinyl Alcohol) Film Containing Silver Nanoparticles: Preparation and Characterization. Journal of Applied Polymer Science 2008; 110(5): 3178-3185.
68. Wei, D W, Sun, W Y, Qian, W P, Ye, Y Z, Ma, X Y. The synthesis of chitosan-based silver nanoparticles and their antibacterial activity. Carbohydrate Research 2009; 344 (17): 2375-2382.
69. Vimala, K, Mohan, Y M, Sivudu, K S, Varaprasad, K, Ravindra, S, Reddy, N N, Padma, Y, Sreedhar, B, MohanaRaju, K. Fabrication of porous chitosan films impregnated with silver nanoparticles: A facile approach for superior antibacterial application. Colloids and Surfaces B-Biointerfaces 2010; 76(1): 248-258.
70. Rai, M, Yadav, A, Gade, A. Silver nanoparticles as a new generation of antimicrobials. Biotechnology Advances 2009; 27(1): 76-83.
71. Lippert, E, Klebl, F, Schweller, F, Ott, C, Gelbmann, C, Scholmerich, J, Endlicher, E, Kullmann, F. Fibrin glue in the endoscopic treatment of fistulae and anastomotic leakages of the gastrointestinal tract. International Journal of Colorectal Disease 2011; 26(3): 303-311.
72. Skardal, A, Zhang, J, McCoard, L, Oottamasathien, S, Prestwich, G D. Dynamically Crosslinked Gold Nanoparticle—Hyaluronan Hydrogels. Advanced Materials 2010; 22(42): 4736-4740.
73. Raub, C B, Putnam, A J, Tromberg, B J, George, S C. Predicting bulk mechanical properties of cellularized collagen gels using multiphoton microscopy. Acta Biomaterialia 2010; 6(12): 4657-4665.
74. Moyer, M P, Manzano, L A, Merriman, R L, Stauffer, J S, Tanzer, L R. NCM460, a normal human colon mucosal epithelial cell line. In Vitro Cellular & Developmental Biology-Animal 1996; 32(6): 315-317.
75. Huang, H C, Barua, S, Kay, D B, Rege, K. Simultaneous Enhancement of Photothermal Stability and Gene Delivery Efficacy of Gold Nanorods Using Polyelectrolytes. Acs Nano 2009; 3(10): 2941-2952.
76. Barua, S, Joshi, A, Banerjee, A, Matthews, D, Sharfstein, S T, Cramer, S M, Kane, R S, Rege, K. Parallel Synthesis and Screening of Polymers for Nonviral Gene Delivery. Molecular Pharmaceutics 2009; 6(1): 86-97.
77. Liang, C C, Park, A Y, Guan, J L. In vitro scratch assay: a convenient and inexpensive method for analysis of cell migration in vitro. Nature Protocols 2007; 2(2): 329-333.
78. Jung, H C, Eckmann, L, Yang, S K, Panja, A, Fierer, J, Morzyckawroblewska, E, Kagnoff, M F. A Distinct Array of Proinflammatory Cytokines Is Expressed in Human Colon Epithelial-Cells in Response to Bacterial Invasion. Journal of Clinical Investigation 1995; 95(1): 55-65.
79. Eckmann, L, Jung, H C, Schurermaly, C, Panja, A, Morzyckawroblewska, E, Kagnoff, M F. Differential Cytokine Expression by Human Intestinal Epithelial-Cell Lines—Regulated Expression of Interleukin-8. Gastroenterology 1993; 105(6): 1689-1697.
80. Werner, S, Grose, R. Regulation of wound healing by growth factors and cytokines. Physiological Reviews 2003; 83(3): 835-870.
81. Wu, Y, MacKay, J A, McDaniel, J R, Chilkoti, A, Clark, R L. Fabrication of Elastin-Like polypeptide Nanoparticles for Drug Delivery by Electrospraying. Biomacromolecules 2009; 10(1): 19-24.
82. Huang, L, McMillan, R A, Apkarian, R P, Pourdeyhimi, B, Conticello, V P, Chaikof, E L. Generation of synthetic elastin-mimetic small diameter fibers and fiber networks. Macromolecules 2000; 33(8): 2989-2997.
83. Qiu, W G, Teng, WB, Cappello, J Y, Wu, X. Wet-Spinning of Recombinant Silk-Elastin-Like Protein Polymer Fibers with High Tensile Strength and High Deformability. Biomacromolecules 2009; 10(3): 602-608.
84. Anumolu, R, Gustafson, J A, Magda, J J, Cappello, J, Ghandehari, H, Pease, L F. Fabrication of Highly Uniform Nanoparticles from Recombinant Silk-Elastin-like Protein Polymers for Therapeutic Agent Delivery. ACS Nano 2011; 5(7): 5374-5382.
85. MacEwan, S R, Chilkoti, A. Elastin-like polypeptides: Biomedical applications of tunable biopolymers. Peptide Science 2010; 94(1): 60-77.
86. Rubert Perez, C M, Panitch, A, Chmielewski, J. A Collagen Peptide-Based Physical Hydrogel for Cell Encapsulation. Macromolecular Bioscience 2011; 11(10): 1426-1431.

REFERENCES FOR EXAMPLE 3

[1] Overgaard J: The current and potential role of hyperthermia in radiotherapy. *Int. J. Radiat. Oncol. Biol. Phys.* 16(3), 535-549 (1989).
[2] Huang X H, Jain P K, El-Sayed I H, El-Sayed M A: Determination of the minimum temperature required for selective photothermal destruction of cancer cells with the use of immunotargeted gold nanoparticles. *Photochem. Photobiol.* 82(2), 412-417 (2006).
[3] He X M, Wolkers W F, Crowe J H, Swanlund D J, Bischof J C: In situ thermal denaturation of proteins in dunning at-1 prostate cancer cells: implication for hyperthermic cell injury. *Ann. Biomed. Engin.* 32(10), 1384-1398 (2004).
[4] Lepock J R: Cellular effects of hyperthermia: relevance to the minimum dose for thermal damage. *Int. J. Hypertherm.* 19(3), 252-266 (2003).
[5] Seki T, Wakabayashi M, Nakagawa T et al.: Percutaneous microwave coagulation therapy for solitary metastatic liver tumors from colorectal cancer: a pilot clinical study. *Am. J. Gastroenterol.* 94(2), 322-327 (1999).
6 Gazelle G S, Goldberg S N, Solbiati L, Livraghi T: Tumor ablation with radiofrequency energy. *Radiology* 217(3), 633-646 (2000).
7 Hilger I, Andra W, Bahring R, Daum A, Hergt R, Kaiser W A: Evaluation of temperature increase with different amounts of magnetite in liver tissue samples. *Investig. Radiol.* 32(11), 705-712 (1997).
[8] Jolesz F A, Hynynen K: Magnetic resonance image-guided focused ultrasound surgery. *Cancer J.* 8, S100-S112 (2002).
[9] Dickerson E B, Dreaden E C, Huang X et al.: Gold nanorod assisted near-infrared plasmonic photothermal therapy (PPTT) of squamous cell carcinoma in mice. *Cancer Lett.* 269(1), 57-66 (2008).
[10] Gobin A M, Lee M R, Halas N J, James W D, Drezek R A, West J L: Near-infrared resonant nanoshells for combined optical imaging and photothermal cancer therapy. *Nano Lett.* 7(7), 1929-1934 (2007).

[11] Skrabalak S E, Chen J, Sun Y et al.: Gold nanocages: synthesis, properties, and applications. *Accounts Chem. Res.* 41(12), 1587-1595 (2008).

[12] Huang X, Jain P K, El-Sayed I H, El-Sayed M A: Plasmonic photothermal therapy (PPTT) using gold nanoparticles. *Lasers Med. Sci.* 23(3), 217-228 (2008).

[13] Huang X, El-Sayed I H, Qian W, El-Sayed M A: Cancer cell imaging and photothermal therapy in the near-infrared region by using gold nanorods. *J. Am. Chem. Soc.* 128(6), 2115-2120 (2006).

[14] Von Maltzahn G, Park J H, Agrawal A et al.: Computationally guided photothermal tumor therapy using long-circulating gold nanorod antennas. *Cancer Res.* 69(9), 3892-3900 (2009).

[15] Ma L L, Feldman M D, Tam J M et al.: Small multifunctional nanoclusters (nanoroses) for targeted cellular imaging and therapy. *ACS Nano* 3(9), 2686-2696 (2009).

[16] Tong L, Wei Q, Wei A, Cheng J-X: Gold nanorods as contrast agents for biological imaging: optical properties, surface conjugation and photothermal effects. *Photochem. Photobiol.* 85(1), 21-32 (2009).

[17] Lepock J R: Cellular effects of hyperthermia: Relevance to the minimum dose for thermal damage. *Int. J. Hypertherm.* 19(3), 252-266 (2003).

[18] Gibbons N B, Watson R W, Coffey R N, Brady H P, Fitzpatrick J M: Heat-shock proteins inhibit induction of prostate cancer cell apoptosis. *Prostate* 45(1), 58-65 (2000).

[19] Rylander M N, Feng Y, Bass J, Diller K R: Thermally induced injury and heat-shock protein expression in cells and tissues. *Ann. NY Acad. Sci.* 1066, 222-242 (2005).

[20] Heath E I, Hillman D W, Vaishampayan U et al.: A Phase II trial of 17-allylamino-17-demethoxygeldanamycin in patients with hormone-refractory metastatic prostate cancer. *Clin. Cancer Res.* 14(23), 7940-7946 (2008).

[21] Solit D B, Osman I, Polsky D et al.: Phase II trial of 17-allylamino-17-demethoxygeldanamycin in patients with metastatic melanoma. *Clin. Cancer Res.* 14(24), 8302-8307 (2008).

[22] Nikoobakht B, El-Sayed M A: Preparation and growth mechanism of gold nanorods (NRs) using seed-mediated growth method. *Chem. Mater.* 15(10), 1957-1962 (2003).

[23] Huang H-C, Koria P, Parker S M, Selby L, Megeed Z, Rege K: Optically responsive gold nanorod—polypeptide assemblies. *Langmuir* 24(24), 14139-14144 (2008).

[24] Rege K, Patel S J, Megeed Z, Yarmush M L: Amphipathic peptide-based fusion peptides and immunoconjugates for the targeted ablation of prostate cancer cells. *Cancer Res.* 67(13), 6368-6375 (2007).

[25] Barua S, Joshi A, Banerjee A et al.: Parallel synthesis and screening of polymers for nonviral gene delivery. *Mol. Pharm.* 6(1), 86-97 (2009).

[26] Gong M C, Latouche J B, Krause A, Heston W D, Bander N H, Sadelain M: Cancer patient T cells genetically targeted to prostate-specific membrane antigen specifically lyse prostate cancer cells and release cytokines in response to prostate-specific membrane antigen. *Neoplasia* 1(2), 123-127 (1999).

[27] Urry D W: Physical chemistry of biological free energy transduction as demonstrated by elastic protein-based polymers. *J. Phys. Chem. B* 101(51), 11007-11028 (1997).

[28] Meyer D E, Chilkoti A: Genetically encoded synthesis of protein-based polymers with precisely specified molecular weight and sequence by recursive directional ligation: examples from the elastin-like polypeptide system. *Biomacromolecules* 3(2), 357-367 (2002).

[29] Janorkar A V, Rajagopalan P, Yarmush M L, Megeed Z: The use of elastin-like polypeptide-polyelectrolyte complexes to control hepatocyte morphology and function in vitro. *Biomaterials* 29(6), 625-632 (2008).

[30] Huang H-C, Barua S, Kay D B, Rege K: Simultaneous enhancement of photothermal stability and gene delivery efficacy of gold nanorods using polyelectrolytes. *ACS Nano* 3(10), 2941-2952 (2009).

[31] Huang Hc, Rege K, Heys J J: Spatiotemporal temperature distribution and cancer cell death in response to extracellular hyperthermia induced by gold nanorods. *ACS Nano* 4(5), 2892-2900 (2009).

[32] Huang X, El-Sayed I H, Qian W, El-Sayed M A: Cancer cell imaging and photothermal therapy in the near-infrared region by using gold nanorods. *J. Am. Chem. Soc.* 128(6), 2115-2120 (2006).

33. Lowery A R, Gobin A M, Day E S, Halas N J, West J L: Immunonanoshells for targeted photothermal ablation of tumor cells. *Int. J. Nanomed.* 1(2), 149-154 (2006).

REFERENCES FOR EXAMPLE 5

1. Park, H., et al., *Effect of Swelling Ratio of Injectable Hydrogel Composites on Chondrogenic Differentiation of Encapsulated Rabbit Marrow Mesenchymal Stem Cells In Vitro.* Biomacromolecules, 2009. 10(3): p. 541-546.

2. Cilesiz, I., et al., *Controlled temperature tissue fusion: Argon laser welding of canine intestine in vitro.* Lasers in Surgery and Medicine, 1996. 18(4): p. 325-334.

3. Poppas, D. P., et al., *Temperature-controlled laser photocoagulation of soft tissue: In vivo evaluation using a tissue welding model.* Lasers in Surgery and Medicine, 1996. 18(4): p. 335-344.

4. Wise, L., W. McAlister, and T. Stein, *Studies on the healing of anastomoses of small and large intestines.* Surg Gynecol Obstet, 1975. 141(190).

5. Pasternak, B., et al., *Doxycycline-coated sutures improve mechanical strength of intestinal anastomoses.* International Journal of Colorectal Disease, 2008. 23(3): p. 271-276.

6. Lipska, M. A., et al., *Anastomotic leakage after lower gastrointestinal anastomosis: Men are at a higher risk.* Anz Journal of Surgery, 2006. 76(7): p. 579-585.

7. Post, S., et al., *Risks of Intestinal Anastomoses in Crohns-Disease.* Annals of Surgery, 1991. 213(1): p. 37-42.

8. Pickleman, J., et al., *The failed gastrointestinal anastomosis: An inevitable catastrophe?* Journal of the American College of Surgeons, 1999. 188(5): p. 473-482.

9. Hooper, L. V., et al., *Molecular analysis of commensal host-microbial relations hips in the intestine.* Science, 2001. 291(5505): p. 881-884.

10. Husebye, E., et al., *Influence of microbial species on small intestinal myoelectric activity and transit in germ-free rats.* American Journal of Physiology-Gastrointestinal and Liver Physiology, 2001. 280(3): p. G368-G380.

11. Leduc, M., R. Kasra, and J. Vanheijenoort, *Induction and Control of the Autolytic System of Escherichia-Coli.* Journal of Bacteriology, 1982. 152(1): p. 26-34.

12. Leduc, M. and J. Vanheijenoort, *Autolysis of Escherichia-Coli.* Journal of Bacteriology, 1980. 142(1): p. 52-59.

What is claimed is:

1. A bioadhesive composition comprising:
a photothermally responsive composition comprising a network of elastin-like polypeptide (ELP) and a light absorbing chromophore,
wherein the light absorbing chromophore comprises one or more metallic nanoparticles physically entrapped within the network of ELP.

2. The bioadhesive composition of claim 1, wherein the one or more metallic nanoparticles comprise silver nanoparticles, gold nanorods, or gold nanoparticles, or mixtures thereof.

3. The bioadhesive composition of claim 1, further comprising an active agent, cells, or a combination thereof physically entrapped within the network of ELP.

4. The bioadhesive composition of claim 3, wherein the active agent comprises an antibacterial agent.

5. The bioadhesive composition of claim 3, wherein the active agent comprises an MMP inhibitor, a soluble factor, a cytokine, or a growth factor.

6. The bioadhesive composition of claim 5, wherein the soluble factor comprises FGF (fibroblast growth factor), TGF-beta, EGF, or a combination thereof.

7. A bioadhesive composition comprising:
a photothermally responsive composition comprising a network of elastin-like polypeptide (ELP) and a light absorbing chromophore,
wherein the light absorbing chromophore comprises one or more metallic nanoparticles physically entrapped within the network of ELP, and
wherein the light absorbing chromophore is configured to convert light to heat upon the application of a directed light beam to the photothermally responsive composition, to a surrounding tissue, or to both, thereby cross-linking the network of ELP in response to the heat.

8. The bioadhesive composition of claim 7, wherein one or more metallic nanoparticles comprise silver nanoparticles, gold nanorods, or gold nanoparticles, or mixtures thereof.

9. The bioadhesive composition of claim 7, wherein the directed light beam is a laser.

10. The bioadhesive composition of claim 7, wherein the light is near infrared.

11. The bioadhesive composition of claim 7, wherein the directed light beam generates a bulk temperature of at least a portion of the photothermally responsive bioadhesive composition above 60° C.

12. The bioadhesive composition of claim 7, wherein the directed light beam generates a bulk temperature of at least a portion of the photothermally responsive bioadhesive composition above 80° C.

13. The bioadhesive composition of claim 7, further comprising an active agent, cells, or a combination thereof physically entrapped within the fibrous network of ELP,
wherein the photothermally responsive composition is configured to release the active agent from the fibrous network of ELP upon the application of the directed light beam.

14. A suture comprising:
at least two fibers, wherein each fiber comprises the bioadhesive composition of claim 1.

15. The suture of claim 14, wherein the one or more metallic nanoparticles comprise silver nanoparticles, gold nanorods, or gold nanoparticles, or mixtures thereof.

16. The suture of claim 14, wherein the directed light beam is a laser.

17. The suture of claim 14, wherein the light is near infrared.

18. The suture of claim 14, wherein the directed light beam generates a bulk temperature of at least a portion of the photothermally responsive bioadhesive composition above 60° C.

19. The suture of claim 14, wherein the directed light beam generates a bulk temperature of at least a portion of the photothermally responsive bioadhesive composition above 80° C.

20. The suture of claim 14, wherein the light absorbing chromophore in the at least two fibers has a weight percentage between 0.5% and 8%.

* * * * *

SEQUENCE LISTING

<160> NUMBER OF SEQ ID NOS: 2

<210> SEQ ID NO 1
<211> LENGTH: 411
<212> TYPE: PRT
<213> ORGANISM: Artificial Sequence
<220> FEATURE:
<223> OTHER INFORMATION: synthetic construct; elastin-like polypeptide

<400> SEQUENCE: 1

```
Met Val Ser Ala Cys Arg Gly Pro Gly Val Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
    130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
        195                 200                 205

Gly Val Gly Val Pro Gly Val Gly Val Pro Gly Val Gly Val Pro Gly
    210                 215                 220

Cys Gly Val Pro Gly Val Gly Val Pro Gly Val Gly Val Pro Gly Val
225                 230                 235                 240

Gly Val Pro Gly Val Gly Val Pro Gly Cys Gly Val Pro Gly Val Gly
                245                 250                 255

Val Pro Gly Val Gly Val Pro Gly Val Gly Val Pro Gly Val Gly Val
            260                 265                 270

Pro Gly Cys Gly Val Pro Gly Val Gly Val Pro Gly Val Gly Val Pro
        275                 280                 285

Gly Val Gly Val Pro Gly Val Gly Val Pro Gly Cys Gly Val Pro Gly
    290                 295                 300

Val Gly Val Pro Gly Val Gly Val Pro Gly Val Gly Val Pro Gly Val
305                 310                 315                 320

Gly Val Pro Gly Cys Gly Val Pro Gly Val Gly Val Pro Gly Val Gly
                325                 330                 335

Val Pro Gly Val Gly Val Pro Gly Val Gly Val Pro Gly Cys Gly Val
            340                 345                 350

Pro Gly Val Gly Val Pro Gly Val Gly Val Pro Gly Val Gly Val Pro
```

```
                355                 360                 365
Gly Val Gly Val Pro Gly Cys Gly Val Pro Val Gly Val Pro Gly
    370                 375                 380

Val Gly Val Pro Gly Val Gly Val Pro Gly Val Gly Val Pro Gly Cys
385                 390                 395                 400

Gly Val Pro Gly Val Gly Val Pro Gly Trp Pro
                405                 410

<210> SEQ ID NO 2
<211> LENGTH: 209
<212> TYPE: PRT
<213> ORGANISM: Artificial Sequence
<220> FEATURE:
<223> OTHER INFORMATION: synthetic construct; elastin-like polypeptide

<400> SEQUENCE: 2

Met Val Ser Ala Cys Arg Gly Pro Gly Val Gly Val Pro Gly Val Gly
1               5                   10                  15

Val Pro Gly Val Gly Val Pro Gly Val Gly Val Pro Gly Val Gly Val
                20                  25                  30

Pro Gly Val Gly Val Pro Gly Val Gly Val Pro Gly Val Gly Val Pro
            35                  40                  45

Gly Val Gly Val Pro Gly Val Gly Val Pro Gly Val Gly Val Pro Gly
        50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
                100                 105                 110

Pro Gly Val Gly Val Pro Gly Val Gly Val Pro Gly Val Gly Val Pro
            115                 120                 125

Gly Val Gly Val Pro Gly Val Gly Val Pro Gly Val Gly Val Pro Gly
        130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
                180                 185                 190

Pro Gly Val Gly Val Pro Gly Val Gly Val Pro Gly Val Gly Val Pro
            195                 200                 205

Gly
```